US011173175B2

(12) United States Patent
Lee

(10) Patent No.: US 11,173,175 B2
(45) Date of Patent: Nov. 16, 2021

(54) URIDINE DIPHOSPHATE COMPOUNDS AS MOBILIZERS OF HEMATOPOIETIC PROGENITOR CELLS

(71) Applicant: University of Pittsburgh—Of the Commonwealth System of Higher Education, Pittsburgh, PA (US)

(72) Inventor: Byeong-Chel Lee, Pittsburgh, PA (US)

(73) Assignee: UNIVERSITY OF PITTSBURGH—OF THE COMMONWEALTH SYSTEM OF HIGHER EDUCATION, Pittsburgh, PA (US)

(*) Notice: Subject to any disclaimer, the term of this patent is extended or adjusted under 35 U.S.C. 154(b) by 192 days.

(21) Appl. No.: 15/239,614

(22) Filed: Aug. 17, 2016

(65) Prior Publication Data
US 2016/0354401 A1 Dec. 8, 2016

Related U.S. Application Data

(60) Division of application No. 14/495,663, filed on Sep. 24, 2014, now Pat. No. 9,439,919, which is a continuation of application No. PCT/US2013/034452, filed on Mar. 28, 2013.

(60) Provisional application No. 61/618,173, filed on Mar. 30, 2012.

(51) Int. Cl.
*A61K 31/7072* (2006.01)
*A61K 38/19* (2006.01)
*A61K 31/395* (2006.01)
*A61K 31/664* (2006.01)
*A61K 31/737* (2006.01)
*A61K 45/06* (2006.01)
*A61K 35/12* (2015.01)
*A61K 35/28* (2015.01)
*A61K 35/00* (2006.01)

(52) U.S. Cl.
CPC ........ *A61K 31/7072* (2013.01); *A61K 31/395* (2013.01); *A61K 31/664* (2013.01); *A61K 31/737* (2013.01); *A61K 35/12* (2013.01); *A61K 35/28* (2013.01); *A61K 38/193* (2013.01); *A61K 45/06* (2013.01); *A61K 35/00* (2013.01)

(58) Field of Classification Search
None
See application file for complete search history.

(56) References Cited

U.S. PATENT DOCUMENTS

| 7,785,601 | B2 * | 8/2010 | Schaebitz | A61K 38/193 424/198.1 |
| 2005/0250678 | A1 * | 11/2005 | DeFrees | A61K 38/193 514/11.4 |
| 2006/0263332 | A1 * | 11/2006 | Li | A61K 35/28 424/85.1 |
| 2011/0257109 | A1 * | 10/2011 | Wurtman | A61K 31/14 514/25 |

FOREIGN PATENT DOCUMENTS

WO WO 2008/086426 7/2008
WO WO 2011/138512 11/2011

OTHER PUBLICATIONS

U.S. Appl. No. 14/495,663, filed Sep. 24, 2014, U.S. Pat. No. 9,439,919, Sep. 13, 2016.
U.S. Appl. No. 15/228,878, filed Aug. 4, 2016, US 2016/0339048, Nov. 24, 2016.
U.S. Appl. No. 14/495,663, Jul. 28, 2016 Issue Fee Payment.
U.S. Appl. No. 14/495,663, May 6, 2016 Notice of Allowance.
U.S. Appl. No. 14/495,663, Feb. 22, 2016 Response to Restriction Requirement.
U.S. Appl. No. 14/495,663, Dec. 21, 2015 Restriction Requirement Filed.
Abbracchio et al., "Purinergic signalling: pathophysiological roles," J. Pharmacol. 78:113-145 (1998).
Alcino et al., "Activity of P536, an Analog of UDP-Glucose, Against *Trypanosoma cruzi*. Antimicrob," Agents and Chemother., 32(9):1412-1415 (1988).
Arase et al., "The UDP-glucose receptor P2RY14 triggers innate mucosal immunity in the female reproductive tract by inducing IL-8," J. Immunol., 182:7074-7084 (2009).
Bai et al., "Reactive oxygen species stimulates receptor activator of NF-κB ligand expression in osteoblast," J. Biol. Chern., 280:17497-17506 (2005).
Barsony et al., "Osteoclast response to low extracellular sodium and the mechanism of hyponatremia-induced bone loss," J. Biol. Chern. 286:10864-10875 (2011).
Brautigam et al., "The inflammatory effects of UDP-glucose in N9 microglia are not mediated by P2Y14 receptor activation," Purinergic Signal, 4:73-78 (2008).
Broxmeyer et al., "Rapid mobilization of murine and human hematopoietic stem and progenitor cells with AMD3100, a CXCR4 antagonist," J. Exp. Med., 201:1307-1318 (2005).

(Continued)

Primary Examiner — Emily A Cordas
(74) Attorney, Agent, or Firm — Baker Botts L.L.P.

(57) ABSTRACT

The present invention provides for compositions and methods for administering one or more UDP compound, alone or in combination with another hematopoietic progenitor cell mobilizing compound (for example, but not limited to G-CSF), to mobilize hematopoietic progenitor cells for transplant or other purposes. The methods of the invention may be particularly advantageous as applied to improve the stem cell yield in so-called "poor mobilizing" patients.

7 Claims, 46 Drawing Sheets

(56) References Cited

OTHER PUBLICATIONS

Figure 1A:
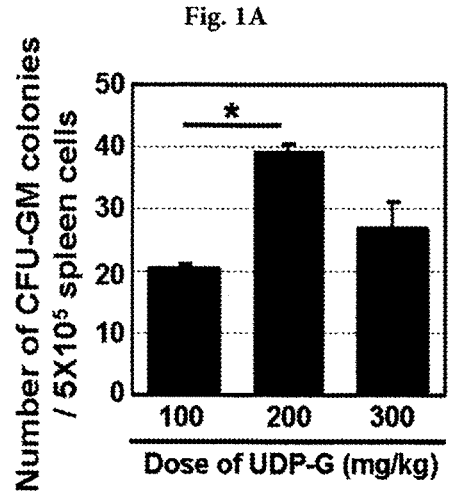
Figure 1B:
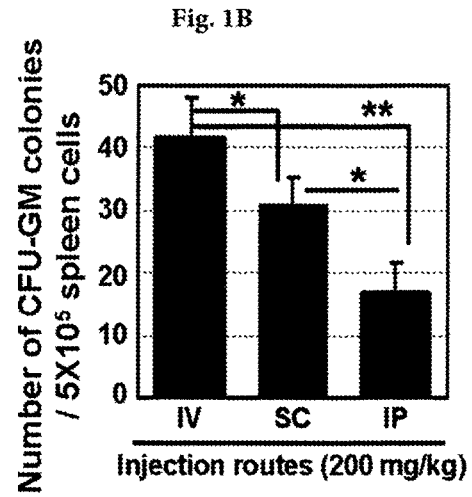

Calvi, et al., "Osteoblastic cells regulate the hematopoietic stem cell niche," Nature, 425:841-846 (2003).
Campbell et al., "UDP-Glucose Analogues as Inhibitors and Mechanistic Probes of UDP-Glucose Dehydrogenase," J. Org. Chem., 64(26):9487-9492 (1999).
Carter et al., "Quantification of Gi-mediated inhibition of adenylyl cyclase activity reveals that UDP is a potent agonist of the human P2Y14 receptor," Mol Pharmacol., 76(6):1341-1348 (2009).
Cashen, et al., "AMD3100: CXCR4 antagonist and rapid stem cell-mobilizing agent," Future Oncol., 3(1):19-27 (2007).
Chen, et al., "ATP release guides neutrophil chemotaxis via P2Y2 and A3 receptors," Science, 314:1792-1795 (2006).
Chitteti, et al., "Genomic and proteomic analysis of the impact of mitotic quiescence on the engraftment of human CD34+ cells," PLoS One, 6:e17498 (2011).
Cho, et al., "Ewing sarcoma gene Ews regulates hematopoietic stem cell senescence," Blood, 117:1156-1166 (2011).
Cottler-Fox, et al., "Stem cell mobilization," Hematology Am Soc Hematol Educ Program, pp. 419-437 (2003).
Cramer, et al., "Mobilization of Hematopoietic Progenitor Cells by Yeast-Derived □-Glucan Requires Activation of Matrix Metalloproteinase-9," Stem Cells, 26:1231-1240 (2008).
D'Addio, et al., "The addition of plerixafor is safe and allows adequate PBSC collection in multiple myeloma and lymphoma patients poor mobilizers after chemotherapy and G-CSF," Bone Marrow Transplant, 46:356-363 (2011).
Dar, et al., "Rapid mobilization of hematopoietic progenitors by AMD3100 and catecholamines is mediated by CXCR4-dependent SDF-1 release from bone marrow stromal cells," Leukemia, 25(8):1286-1296 (2011).
De Clerq et al., "Recent advances on the use of the CXCR4 antagonist plerixafor (AMD3100, Mozobil™) and potential of other CXCR4 antagonists as stem cell mobilizers," Pharmacology & Therapeutics, 128:509-518 (2010).
Di Virgilio, et al., "Nucleotide receptors: an emerging family of regulatory molecules in blood cells," Blood, 97:587-600 (2001).
Eigenbrodt, et al., "Double role for pyruvate kinase type M2 in the expansion of phosphometabolite pools found in tumor cells," Crit Rev Oncog 3:91-115 (1992).
Fricks, et al., "UDP Is a Competitive Antagonist at the Human P2Y14 Receptor," J. Pharmacol Exp Ther., 325(2):588-594 (2008).
Greenbaum, et al., "Mechanisms of G-CSF-mediated hematopoietic stem and progenitor mobilization," Leukemia, 25:211-217 (2011).
Hamel et al., "Discovery of novel P2Y14 agonist and antagonist using conventional and nonconventional methods," J Biomol Screen 16(9):1098-1105 (2011).
Hartmann, et al., "Peripheral blood stem cell and bone marrow transplantation for solid tumors and lymphomas: hematologic recovery and costs. A randomized, controlled trial," Ann Intern Med, 126:600-607 (1997).
He, et al., "Sox17 expression confers self-renewal potential and fetal stem cell characteristics upon adult hematopoietic progenitors," Genes Dev, 25:1613-1627 (2011).
Hill, et al., "Stem cell mobilization with G-CSF induces type 17 differentiation and promotes scleroderma," Blood, 116:819-828 (2010).
Hornung, et al., "Hematopoietic stem cell depletion by restorative growth factor regimens during repeated high-dose cyclophosphamide therapy," Blood, 80:77-83 (1992).
International Search Report and Written Opinion for PCT/US2013/034452, dated Jul. 25, 2013.
Ke, et al., "Deletion of the P2X7 nucleotide receptor reveals its regulatory roles in bone formation and resorption," Mol Endocrinol, 17:1356-1367 (2003).
Kollet, et al., "Osteoclasts degrade endosteal components and promote mobilization of hematopoietic progenitor cells," Nat Med., 12:657-664 (2006).

Kook et al., "The nucleotide sugar UDP-glucose mobilizes long-term repopulating primitive hematopoietic cells," The Journal of Clinical Investigation, 123(8):3420-3435 (Aug. 2013).
Lapid, et al., "Egress and mobilization of hematopoietic stem and progenitor cells: A Dynamic multi-facet process," StemBook, Harvard Stem Cell Institute, (37 pages) (2008).
Lazarowski, et al., "Release of cellular UDP-glucose as a potential extracellular signaling molecule," Mol Pharmacol, 63:1190-1197 (2003).
Lee, et al., "P2Y-like receptor, GPR105 (P2Y14), identifies and mediates chemotaxis of bone-marrow hematopoietic stem cells," Genes Dev, 17:1592-1604 (2003).
Lekli, et al., "Redox regulation of stem cell mobilization," Can J Physiol Pharmacol, 87:989-995 (2009).
Lemoli et al., "Extracellular nucleotides are potent stimulators of human hematopoietic stem cells in vitro and in vivo," Blood, 104(6): 1662-1670 (2004).
Levesque, et al., "Mobilization by either cyclophosphamide or granulocyte colony-stimulating factor transforms the bone marrow into a highly proteolytic environment," Exp Hematol, 30:440-449 (2002).
Li, et al., "Separating graft-versus-leukemia from graft-versus-host disease in allogeneic hematopoietic stem cell transplantation," Immunotherapy, 1:599-621 (2009).
Linden, J. "Cell biology. Purinergic chemotaxis," Science, 314:1689-1690 (2006).
Liu, et al., "Expression of the G-CSF receptor on hematopoietic progenitor cells is not required for their mobilization by G-CSF," Blood, 95:3025-3031 (2000).
Liu, et al., "Impaired production and increased apoptosis of neutrophils in granulocyte colony-stimulating factor receptor-deficient mice," Immunity, 5:491-501 (1996).
Majolino, et al., "Allogeneic transplants of rhG-CSF-mobilized peripheral blood stem cells (PBSC) from normal donors," GITMO. Gruppo Italiano Trapianto di Midollo Osseo. Haematologica, 80:40-43 (1995).
Micklem, et al., "Limited potential of circulating hematopoietic stem cells," Nature, 256:41-43 (1975).
Miyamoto, et al., "Osteoclasts are dispensable for hematopoietic stem cell maintenance and mobilization," J Exp Med, 208:2175-2181 (2011).
Mollee, et al., "Cyclophosphamide, etoposide and G-CSF to mobilize peripheral blood stem cells for autologous stem cell transplantation in patients with lymphoma," Bone Marrow Transplant, 30:273-278 (2002).
Neben, et al., "Mobilization of hematopoietic stem and progenitor cell subpopulations from the marrow to the blood of mice following cyclophosphamide and/or granulocyte colony-stimulating factor," Blood, 81:1960-1967 (1993).
Park, et al., "In vivo evaluation of human hematopoiesis through xenotransplantation of purified hematopoietic stem cells from umbilical cord blood", Nat Protoc., 3:1932-1940 (2008).
Passegue, et al., "Global analysis of proliferation and cell cycle gene expression in the regulation of hematopoietic stem and progenitor cell fates," J Exp Med, 202:1599-1611 (2005).
Peled, et al., "Dependence of human stem cell engraftment and repopulation of NOD/SCID mice on CXCR4," Science, 283:845-848 (1999).
Platzbecker, et al., "Spleen enlargement in healthy donors during G-CSF mobilization of PBPCs," Transfusion, 41:184-189 (2001).
Ploemacher, et al., "An in vitro limiting-dilution assay of long-term repopulating hematopoietic stem cells in the mouse," Blood, 74:2755-2763 (1989).
Pruijt, et al., "Neutrophils are indispensable for hematopoietic stem cell mobilization induced by interleukin-8 in mice," PNAS, 99:6228-6233 (2002).
Pulliam, et al., "AMD3100 synergizes with G-CSF to mobilize repopulating stem cells in Fanconi anemia knockout mice," Exp Hematol, 36:1084-1090 (2008).
Purton, et al., "Osteoclasts eat stem cells out of house and home," Nat Med., 12:610-611 (2006).

(56) References Cited

OTHER PUBLICATIONS

Roberts, et al., "Genetic influences determining progenitor cell mobilization and leukocytosis induced by granulocyte colony-stimulating factor," Blood, 89:2736-2744 (1997).
Rossi et al., "The extracellular nucleotide UTP is a potent inducer of hematopoietic stem cell migration," Blood, 109(2):533-542 (2007).
Sak, et al., "Involvement of P2Y receptors in the differentiation of hematopoietic cells," J Leukoc Biol, 73:442-447 (2003).
Schmitz, et al., "Randomized trial of filgrastim-mobilized peripheral blood progenitor cell transplantation versus autologous bone-marrow transplantation in lymphoma patients," Lancet, 347:353-357 (1996).
Schwarzenberger, et al., "IL-17 mobilizes peripheral blood stem cells with short- and long-term repopulating ability in mice," J Immunol, 167:2081-2086 (2001).
Scrivens, et al., "Pharmacological effects mediated by UDP-glucose that are independent of P2Y14 receptor expression," Pharmacol Res, 51:533-538. (2005).
Steinman, R.A. "Cell cycle regulators and hematopoiesis," Oncogene, 21:3403-3413 (2002).
Takamatsu, et al., "Osteoclast-mediated bone resorption is stimulated during short-term administration of granulocyte colony-stimulating factor but is not responsible for hematopoietic progenitor cell mobilization," Blood, 92:3465-3473 (1998).
Tesio, et al., "Enhanced c-Met activity promotes G-CSF-induced mobilization of hematopoietic progenitor cells via ROS signaling," Blood, 117:419-428 (2011).
Tricot, et al., "Peripheral blood stem cell transplants for multiple myeloma: identification of favorable variables for rapid engraftment in 225 patients," Blood, 85:588-596 (1995).
Urbaniak et al., "Galactose starvation in a bloodstream form trypanosome brucei UDP-glucose 4-epimerase conditional null mutant," Eukaryotic Cell, 5(11):1906-1913 (2006).
Wihlborg, et al., "Positive inotropic effects by uridine triphosphate (UTP) and uridine diphosphate (UDP) via P2Y2 and P2Y6 receptors on cardiomyocytes and release of UTP in man during myocardial infarction," Circ Res., 98(7):970-976 (2006).
Wright, et al., "Cyclophosphamide/granulocyte colony-stimulating factor causes selective mobilization of bone marrow hematopoietic stem cells into the blood after M phase of the cell cycle," Blood, 97:2278-2285 (2001).
Yeoh, et al., "Mobilized peripheral blood stem cells provide rapid reconstitution but impaired long-term engraftment in a mouse model," Bone Marrow Transplant, 39:401-409 (2007).
Yoshida, et al., "The murine mutation osteopetrosis is in the coding region of the macrophage colony stimulating factor gene," Nature, 345:442-444 (1990).

* cited by examiner

Peripheral blood

Spleen

Fig. 12A
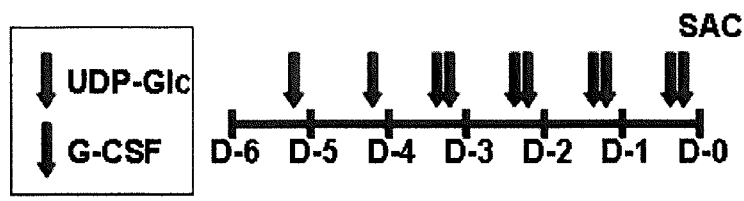
Fig. 12B
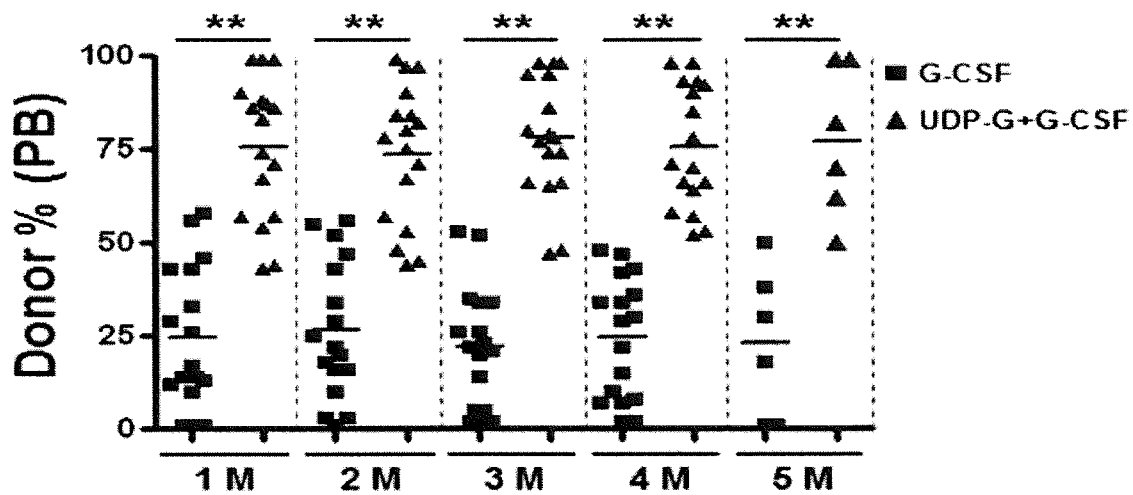
Fig. 12C
Fig. 12D
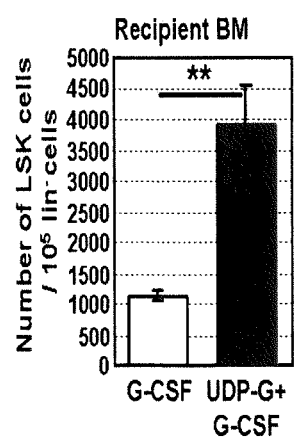
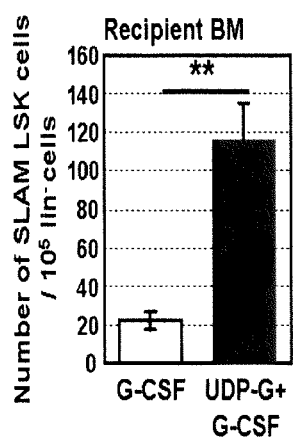

URIDINE DIPHOSPHATE COMPOUNDS AS MOBILIZERS OF HEMATOPOIETIC PROGENITOR CELLS

PRIORITY CLAIM

This application is a divisional of U.S. patent application Ser. No. 14/495,663, filed Sep. 24, 2014, which is a continuation of PCT/US13/034452, filed Mar. 28, 2013, and claims priority to U.S. Provisional Application No. 61/618,173 filed Mar. 30, 2012, the contents of each of which are incorporated by reference in their entirety herein, and priority to each of which is claimed.

GRANT INFORMATION

This invention was made with government support under grant number W81XWH-09-1-0364 awarded by the Department of Defense. The government has certain rights in the invention.

1. INTRODUCTION

The present invention relates to the use of uridine diphosphate compounds and particularly uridine diphosphate glucose in methods for mobilizing hematopoietic progenitor cells from the bone marrow, alone or together with another mobilizing agent such as granulocyte colony stimulating factor, AMD-3100, cyclophosphamide or fucoidan.

2. BACKGROUND OF THE INVENTION

Hematopoietic stem progenitor cells (HSPCs) are normally present in very small numbers in the circulating blood. However, in response to stress or injury, HSPCs are primed to migrate out of their niche into the peripheral blood. HSPCs have been developed as an alternative to bone marrow harvest for transplant. Because they exhibit faster engraftment and reduced risk of posttransplant infection, mobilized HSPCs are now more commonly used as stem cell sources.

Uridine diphosphate-glucose ("UDP-glucose") is a nucleotide sugar which is released into extracellular fluids in response to various stressors (Lazarowski et al., "Release of cellular UDP-glucose as a potential extracellular signaling molecule," Mol Pharmacol 63, 1190-1197, 2003). UDP is a potent agonist of the human P2Y14 receptor (Carter et al., "Quantification of Gi-mediated inhibition of adenylyl cyclase activity reveals that UDP is a potent agonist of the human P2Y14 receptor," Mol. Pharmacol. 76(6):1341-8, 2009) and has been reported to be associated with a number of physiologic effects, including inotropic effects in cardiac myocytes mediated by P2Y6 receptors via an IP3-dependent pathway (Wihlborg et al., "Positive inotropic effects by uridine triphosphate (UTP) and uridine diphosphate (UDP) via P2Y2 and P2Y6 receptors on cardiomyocytes and release of UTP in man during myocardial infarction," Circ. Res. 98(7):970-6, 2006).

3. SUMMARY OF THE INVENTION

The present invention relates to the use of UDP compounds (including UDP itself, UDP-sugars such as UDP-glucose, and others) to mobilize hematopoietic progenitor cells such as HSPCs from the bone marrow into the peripheral circulation of a subject.

It is based, at least in part, on the discovery that UDP-glucose is a mediator of HSPC mobilization. Specifically, it was discovered that UDP-glucose-mobilized HSPCs differentiated into multi-lineage blood cells and achieved long-term repopulation in lethally irradiated animals. The lymphoid-biased differentiation and ability to preferentially support long term repopulation of UDP-glucose mobilized HSPCs is superior to that of G-CSF mobilized HSPCs. It was further discovered that co-administration of UDP-Glucose and G-CSF led to a synergistic enhancement of HSPC mobilization.

Accordingly, the present invention provides for compositions and methods for administering one or more UDP compound, alone or in combination with another hematopoietic progenitor cell mobilizing compound (for example, but not limited to, G-CSF), to mobilize hematopoietic progenitor cells for transplant or other purposes. The methods of the invention may be particularly advantageous as applied to improve the stem cell yield in so-called "poor mobilizing" patients.

4. BRIEF DESCRIPTION OF THE FIGURES

FIG. 1A-1F. Hematopoietic stem progenitor cell mobilization with UDP-glucose. The effects of doses (A) and injection routes (B) were determined. IV: Intravenous; SC: subcutaneous; IP: intra-peritoneal. The data shown are the mean±SD. *p<0.05 and ** p<0.01. (C-D) Four to six weeks old C57BL/6 (C) and BALB/C (D) mice were injected daily with a single dose of UDP-Glc (UDP-G, 200 mg/kg). Control mice were similarly injected s.c. with vehicle (PBS). Peripheral blood was drawn at the indicated time points after the initial UDP-Glc administration and LSK cells derived from mobilized blood were quantified by flow cytometry. The data shown are the mean±SD. *p<0.05 and ** p<0.01. (E-F) Four to six weeks old C57BL/6 (E) and BALB/C (F) mice were treated once daily for 6 days with s.c injections of vehicle (CTL) or UDP-Glc (UDP-G). Peripheral blood cells were harvested and assayed for colony forming cells. The number of BFU-E, CFU-GM and CFU-GEMM colonies was counted using standard criteria. The data shown are the mean±SD. *p<0.05 and ** p<0.01.

FIG. 2A-2G. UDP-Glucose mobilizes hematopoietic stem progenitor cell with long-term engraftment potential. (A-B) Mice were injected s.c. once daily with UDP-Glc (200 mg/kg, 6 days) or G-CSF (300 µg/kg, 4 days) or PBS (CTL). Peripheral blood (A) and spleen (B) cells were harvested and assayed for colony forming cells as described in FIG. 1E. The data shown are the mean±SD. *p and #p<0.05 and ** p and ##p<0.01. (C) Mice were treated as described above. Peripheral blood cells were harvested and overlaid on irradiated stromal layers in 96 well plates. At least 20 individual wells were scored for the presence or absence of cobblestone areas. After 5 weeks, wells containing cobblestone areas were counted as positive wells. The assays were repeated twice with similar results. (D) Mice were treated as described above. Mobilization efficiency was assessed by the numbers of circulating LSK cells in peripheral blood. The data shown are the mean±SD. *p<0.05. (E) Schema showing the experimental design used to compare short- and long-term repopulating ability between UDP-Glc-, G-CSF-, and G-CSF+UDP-Glc-mobilized peripheral blood cells. (F) Peripheral blood cells (1.5-2×10$^6$) were collected from PBS- and UDP-Glc-injected mice and transplanted in equal numbers into lethally irradiated recipient animals. The contribution of donor cells was measured by quantifying the percentage of CD45.1 (vehicle injected) and CD45.2 (UDP-Glc injected) cells in the peripheral blood of the recipient animals at the indicated times after transplantation. (G) Sixteen weeks after transplantation, bone marrow cells were pooled from at least five recipient animals and analyzed by flow cytometry for LSK and SLAM LSK cells after gating on CD45.1+(PBS injected) and CD45.2+(UDP-Glc injected) cells. Numbers indicate the percentage of gated cells.

FIG. 3A-3G. Hematopoietic stem progenitor cell mobilized by UDP-Glc are functionally different from counterpart cells mobilized by G-CSF. (A) Mice were injected s.c. once daily with UDP-Glc (200 mg/kg, 6 days) or G-CSF (300 µg/kg, 4 days). The competitive repopulation assay was performed as described in FIG. 2F UDP-Glc-mobilized blood cells ($2\times10^6$) were mixed with an equal number of G-CSF-mobilized blood cells, and then transplanted into conditioned (10 Gy TBI) recipient animals. (B-C) Eighteen weeks after transplantation, bone marrow cells were pooled from at least six recipient animals and analyzed by flow cytometry for LSK (3B) and SLAM LSK (3C) cells after gating on CD45.1+(G-CSF injected) and CD45.2+(UDP-Glc injected) cells. (D) Mice were injected s.c. once daily with UDP-Glc (200 mg/kg, 6 days) or G-CSF (300 µg/kg, 4 days). Peripheral blood cells were pooled from at least four animals and analyzed by flow cytometry for LSK (left panel) and SLAM LSK (right panel) cells. Numbers indicate the percentage of gated cells within the total number. (E) Primary recipients were transplanted as described in FIG. 3A. Recipient animals showing an approximately equal contribution of UDP-Glc- and G-CSF mobilized cells in their blood were used for the serial transplantation experiments. Bone marrow cells from primary recipients were sorted based on their expression of CD45. A mixture of equal numbers of bone marrow cells-derived from UDP-Glc-(CD45.2) and G-CSF (CD45.1)-mobilization were transplanted into secondary recipients (n>3). Donor cell chimerism in the recipient mice was analyzed. (F) The effect of UDP-Glc on cell cycle status of HSPCs was evaluated using LSK cells from control (vehicle-injected) or UDP-Glc-injected mice. Mice (n=5) were injected once daily with UDP-Glc or PBS for 6 days as described above. The bone marrow (upper panel) and blood (lower panel) samples were pooled from each group (n=5) and stained for Ki67 and DAPI. LSK cells were pre-gated and further analyzed for their cell cycle status. The fraction of cells in the respective cell cycle phases is indicated in percent. (G) Recipient animals were transplanted as described in FIG. 3A. Peripheral blood cells from recipient animals (n=3) were pooled and analyzed at 4 months post transplant. The differentiation potential of UDP-Glc- and G-CSF-mobilized cells was determined using CD11b and B220 as markers of myeloid and lymphoid lineages, respectively.

FIGS. 4A-4F. A combination of UDP-Glc and G-CSF has an improved mobilization efficacy over the use of either agent alone. (A) Schema of combinatorial administration schedule: G-CSF was injected daily for 4 consecutive days. UDP-Glc was injected daily for 6 consecutive days. Mice were sacrificed (day 0. SAC) and blood cells were further analyzed for hematopoietic stem progenitor cell activity. (B-C) Mice were injected with G-CSF alone (white bars) or in combination with UDP-Glc (black bars) as described in (A). Peripheral blood (B) and spleen (C) cells were harvested and assayed for colony forming cells as described in FIG. 1E. The colony number produced by G-CSF mobilization was arbitrarily set as 1. The Y-axis represents the average fold change. The data shown are the mean±SD. $*p<0.05$ and $**p<0.01$. (D) Mice were injected with G-CSF alone (white bars) or in combination with UDP-Glc (black bars) as described in (A). Peripheral blood cells were harvested and assayed for CAFC as described in FIG. 2C. The CAFC produced by G-CSF mobilization was arbitrarily set as 1. The Y-axis represents the average fold change. The data shown are the mean±SD. $*p<0.05$. (E) Mice were treated as described in (A). Peripheral blood cells were pooled from at least four animals and analyzed for LSK cells by flow cytometry. The LSK cell numbers mobilized by G-CSF was arbitrarily set as 1. The Y-axis represents the average fold change. The data shown are the mean±SD. $*p<0.05$. (F) Mice were treated as described in (A). Peripheral blood cells were collected from G-CSF- and UDP-Glc/G-CSF-injected mice and transplanted in equal numbers into lethally irradiated recipient animals. The contribution of donor cells in the peripheral blood of the recipient animals was assessed at the indicated times as described in FIG. 2F.

FIG. 5A-5D. UDP-Glucose increases mitochondrial ROS levels and promotes a transient osteoclast differentiation. (A) Mice were injected with UDP-Glc or UDP-Glc/G-CSF as described in FIG. 4A. Bone marrow cells were stained to identify LSK cells. The cellular levels of mitochondrial superoxide were determined using MitoSOX-red within LSK cells. Numbers indicate the percentage of gated cells. Shown are representative histograms from at least four mice per group. (B) Mice were injected with UDP-Glc as described above. Bone marrow cell lysates were analyzed by Western blotting for RANKL expression. Values above each band represent fold difference in RANKL expression relative to control sample (CTL, vehicle injected) after normalization to β-actin loading control, as determined by densitometry.

(C-D) Mice were treated as above. The femurs were sectioned longitudinally and immunostained with an antibody to RANKL (C). Tissue sections were also stained for tartrate-resistant acid phosphatase (TRAP) activity (D). Arrowheads (black color) indicate TRAP-positive cells. A representative TRAP staining is shown. Scale bar, 50 µm.

FIG. 6A-6D. ROS scavengers prevent UDP-Glc-induced hematopoietic stem progenitor cell mobilization. (A) Mice (n>4 per each group) were treated with NAC as described in Material and Methods. Note that UDP-Glc-mediated HSPC mobilization was significantly suppressed by NAC treatment. The data shown are the mean±SD. $\#p<0.05$ and $**p<0.01$
(B-C) Mice were treated as described in FIG. 6A. RANKL expression was determined by Western blotting (B) and immunohistochemistry (C). In Western blot analysis, the numerical values represent the fold change in densitometry data (calculated as above). Scale bar, 50 µM.
(D) Mice were treated as indicated. Arrowheads (black color) indicate TRAP-positive cells. A representative TRAP staining is shown. Scale bar, 50 µM.

Figure 7:
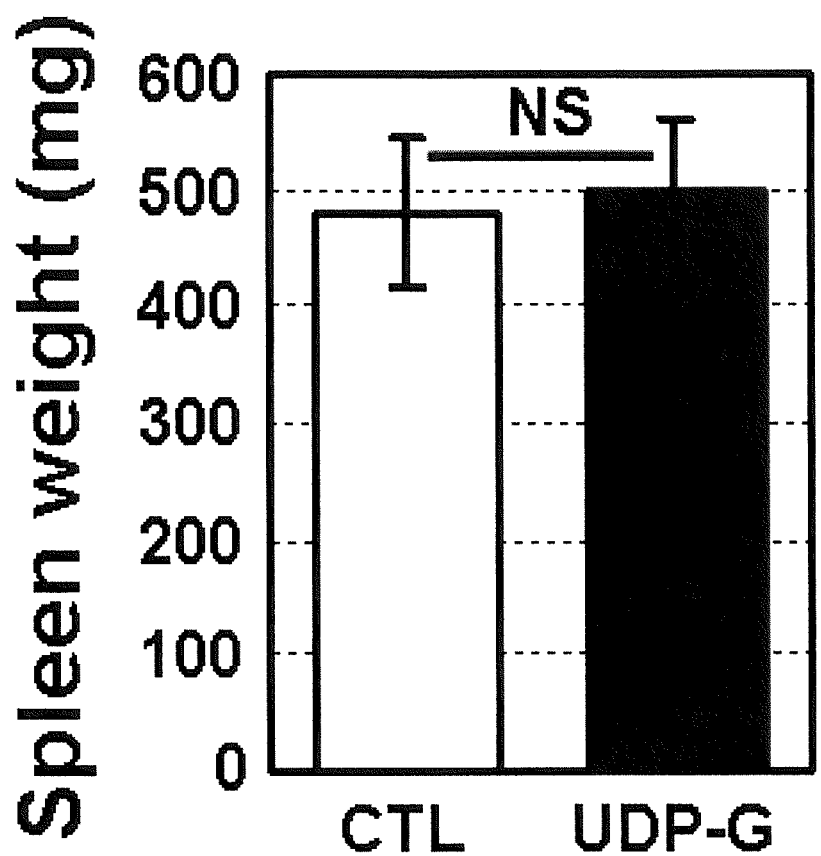

FIG. 7. Mice were injected with UDP-Glc (UDP-G, n=11) or PBS (CTL, n=3) as described in Materials and Methods. The spleens were removed and weighed. The data shown are the mean±SEM. NS=not significant.

Figure 8:
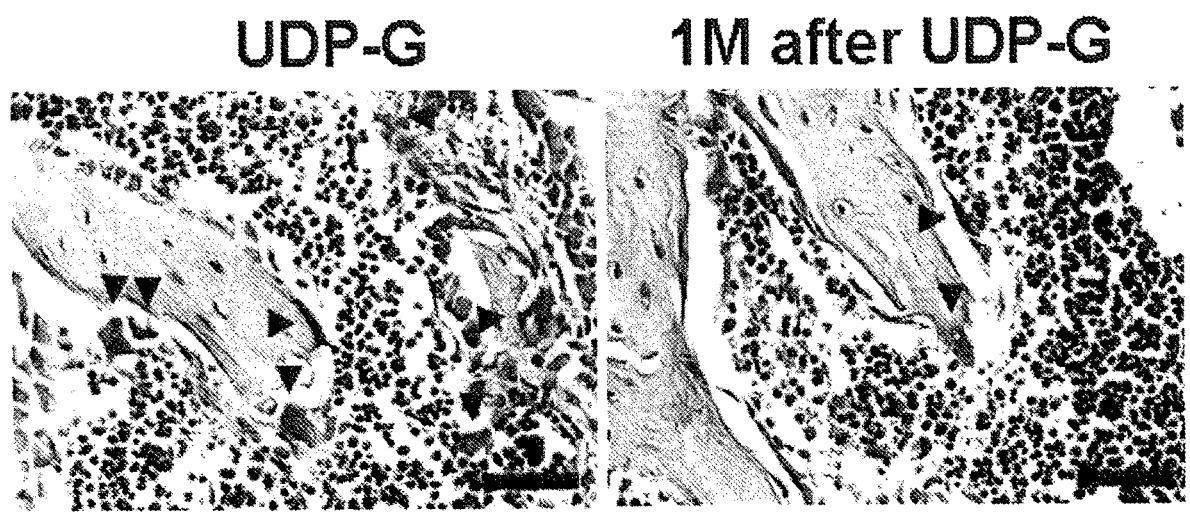

FIG. 8. Mice were injected daily for 6 days with UDP-Glc as described and then left untreated for 3-4 weeks. TRAP staining was done as described in Materials and Methods. Arrowheads indicate TRAP-positive cells. A representative TRAP staining is shown. Scale bar, 50 µM.

FIG. 9A-9E. Hematopoietic progenitor cell mobilization with UDP-glucose. (A) The effects of doses (left panel) and injection routes (middle panel) were determined. IV: Intravenous; SC: subcutaneous; IP: intra-peritoneal. The mobilizing effect of UDP-Glc peaked 2-4 hours after UDP-Glc injection (right panel). Hence, peripheral blood cells were collected 2-4 hours after the last injection in all experiments unless otherwise stated. The results were based on three independent experiments and expressed as mean values±SD. *p<0.05 and ** p<0.01. (B) B6 mice were injected once daily for 6 days with a single dose of UDP-Glc (UDP-G, 200 mg/kg). Control mice were similarly injected s.c. with vehicle (PBS). Single-cell suspensions from spleens of vehicle—(CTL, n=7) or UDP-Glc-injected (UDP-G, n=8) mice were stained for the stem cell markers (Ling Sca-1+ Kit+(LSK)) and SLAM markers (CD150+CD48-LSK)) and analyzed by flow cytometry to determine the number of splenic HSPCs. Mice were individually analyzed for each group, and the mean±SD is shown. *p<0.05. (C) B6 (left panel) and BALB/C (right panel) mice were injected daily with a single dose of UDP-Glc (UDP-G, 200 mg/kg). Control mice were similarly injected s.c. with vehicle (PBS). Peripheral blood was drawn at the indicated time points after the initial UDP-Glc administration and LSK cells derived from mobilized blood were quantified by flow cytometry. Since bone marrow cells from BALB/C mice express low or no level of Sca-1, Lin-, c-Kit+(LK) subsets were quantified in BALB/C mice. The results were based on three independent experiments and expressed as mean values±SD. *p<0.05 and ** p<0.01. (D) B6 (left panel) and BALB/C (right panel) mice were treated once daily for 6 days with s.c. injections of vehicle (CTL) or UDP-Glc (UDP-G). Peripheral blood cells were harvested and assayed for colony forming cells. The number of BFU-E, CFU-GM and CFU-GEMM colonies was counted using standard criteria. Results are shown as mean±SD of three independent experiments, each with duplicate wells per treatment group. *p<0.05 and  p<0.01. (E) Chemotaxis assays were performed in duplicate using 5-μm pore filters. Lineage-depleted (Lin-) bone marrow cells from B6 mice were placed in the upper well (106/well). CXCL12 (120 ng/ml), UDP-Glc (UDP-G, 10 μM), or UTP (10 μM) was placed to the lower wells. After 6 hours of incubation, all cells that migrated to the lower wells were collected and stained for Sca-1 and c-Kit. Absolute number of c-Kit+, Sca-1+ cells was quantified by flow cytometry. Results are a summary of two independent experiments, each with duplicate wells per treatment condition. Concentrations of UTP and CXCL12 used in this chemotaxis assay were based on those used in previous study (18). Of note, the chemotactic migration of LSK cells in response to UDP-Glc was not significantly different at all tested concentrations (e.g., 1 μM, 10 μM and 50 μM).  p<0.01

FIG. 10A-10J. UDP-Glucose mobilizes hematopoietic stem progenitor cell with long-term engraftment potential. (A-B) Mice (B6) were injected s.c. once daily with UDP-Glc (200 mg/kg, 6 days) or G-CSF (300 μg/kg, 4 days) or PBS (CTL) or a combination of G-CSF and UDP-Glc (as shown in the schema in FIG. 17). Peripheral blood (A) and spleen (B) cells were harvested and assayed for colony forming cells as described in FIG. 9D. Results are shown as mean±SD of three independent experiments, each with duplicate wells per treatment group. *p and #p<0.05 and ** p and ##p<0.01. (C) Primary stromal cells were prepared from mouse bone marrow-nucleated cells as described (59). Once confluent, stromal layers were irradiated and subcultured in 96 well plates. Mice (B6) were treated as described above. Peripheral blood cells were harvested and overlaid on irradiated stromal layers in 96 well plates. At least 20 individual wells were scored for the presence or absence of cobblestone areas. After 5 weeks, wells containing cobblestone areas were counted as positive wells. The assays were repeated three times with similar results. *p<0.05 and #p<0.05 and ** p<0.01. (D) Mice were treated as described above. Mobilization efficiency was assessed by the numbers of circulating LSK cells in peripheral blood. Mice were individually analyzed for each group (n>5 mice per group), and the mean±SD is shown. *p<0.05 and #p<0.05 and ** p<0.01. (E) Peripheral blood cells (1.5-2×10$^6$) were collected from PBS- and UDP-Glc-injected mice and transplanted in equal numbers into lethally irradiated recipient animals (see schema in FIG. 17). The contribution of donor cells was measured by quantifying the percentage of CD45.1 (vehicle-injected) and CD45.2 (UDP-Glc-injected) cells in the peripheral blood of the recipient animals at the indicated times after transplantation. (F) Sixteen weeks after transplantation, bone marrow cells were analyzed by flow cytometry for LSK and SLAM LSK cells after gating on CD45.1+ (PBS-injected) and CD45.2+(UDP-Glc-injected) cells. Left: Representative flow cytometry plots showing the frequency of LSK and SLAM LSK cells in recipient bone marrow. Right: Data are expressed as number of LSK (upper panel) and SLAM LSK (lower panel) cells per 10$^5$ lineage-negative cells. Mice were individually analyzed for each group (n=6 mice per group), and the mean±SD is shown. *p<0.05 and ** p<0.01. (G) SLAM LSK cells were sorted from the bone marrow of primary recipients and transplanted into irradiated secondary and tertiary recipients. Donor-derived SLAM LSK cells (CD45.2+) were transplantable to secondary and tertiary recipient mice. Tertiary recipient animals were examined at 5-6 weeks posttransplant. Peripheral blood of recipient animals (n=5) was analyzed to evaluate multilineage reconstitution (left panel (graph)); Right: Representative flow cytometric dot plots showing gating for HSPCs. Bone marrow of recipient animals (n=5) were analyzed for donor-derived HSPC engraftment. Percentages of positive cells within each gate are shown (center and right panels). (H) B6 mice were injected as described in FIG. 10A. Peripheral blood mononuclear cells were collected from each treatment group and stained with indicated antibodies followed by flow cytometry analysis. UDP-Glc treatment did not cause a significant change in WBC and the lineage-marker expressing cells (CD3, CD11b, and Gr-1). No gross or histologic changes were seen in the bone marrow of the UDP-Glc-treated animals. Data are depicted as the mean number of white blood cell (WBC) per milliliter of blood. For lineage-marker expressing cells, a mean value of the cell number±SD obtained from three independent is shown. *p<0.05 and ** p<0.01. (I) Csf3r-/- (KO) and wild-type mice were treated with UDP-Glc (UDP-G) or PBS (CTL) as described in the legend to FIG. 10H. Each treatment group contained more than five mice. Left: Flow cytometry plots show the gating strategy for identification of LSK cells. Peripheral blood cells are first gated on a forward scatter/side scatter (FS/SS) dot plot (top panels). Lineage negative (Lin-) cells were then gated (not shown) with subsequent gating on c-Kit+, Sca-1+ cells (bottom panels). Right: Mice (n>5 per each group) were individually analyzed for each group, and the mean±SD is shown. *p<0.05 and ** p and ##p<0.01. (J) Csf3r-/- (KO) and wild-type mice (n=5 per each treatment group) were treated exactly as described above. Peripheral blood was collected and analyzed as described in the legend to FIG. 10H. The data are shown as mean values of three independent experiments with standard deviation.

FIG. 11A-11J. Hematopoietic stem progenitor cell mobilized by UDP-Glc are functionally different from counterpart cells mobilized by G-CSF. (A) Mice (B6) were injected s.c. once daily with UDP-Glc (200 mg/kg, 6 days) or G-CSF (300 µg/kg, 4 days). The competitive repopulation assay was performed as described (see FIG. 17). UDP-Glc-mobilized blood cells (2×106) were mixed with an equal number of G-CSF-mobilized blood cells, and then transplanted into conditioned (10 Gy TBI) recipient animals. The contribution of donor cells was measured at the indicated times after transplantation. (B-C) Eighteen weeks after transplantation, bone marrow cells were obtained from recipient animals (n>3) and analyzed by flow cytometry for LSK (3B) and SLAM LSK (3C) cells after gating on CD45.1+(G-CSF injected) and CD45.2+(UDP-Glc injected) cells. Data are expressed as number of LSK and SLAM LSK cells per $10^5$ lineage-negative cells. The data shown are the mean±SD. *p<0.05 and ** p<0.01. (D) Primary recipients (CD45.1.2) were transplanted as described in FIG. 3A. Two to three months after transplantation, bone marrow cells from primary recipients were sorted based on their expression of CD45. A mixture of equal numbers of bone marrow cells-derived from UDP-Glc-(CD45.2) and G-CSF (CD45.1)-mobilization were transplanted into secondary recipients (CD45.1.2). Donor cell chimerism in the recipient mice was analyzed at the indicated times post-transplant. (E) FACS-sorted SLAM LSK cells from the bone marrow of primary recipients were used for serial transplantation. A 1:1 mixture of SLAM LSK bone marrow cells derived from UDP-Glc-(CD45.2) and G-CSF (CD45.1)-mobilization were transplanted into secondary and tertiary recipients. Two months later the peripheral blood (left) and bone marrow (right) of the tertiary recipients (n=5) were analyzed for donor cell engraftment. (F) Mice (B6) were injected s.c. once daily with UDP-Glc (200 mg/kg, 6 days) or G-CSF (300 µg/kg, 4 days). Peripheral blood cells were analyzed by flow cytometry for LSK and SLAM LSK cells. Left: Representative flow cytometry plots showing the frequency of LSK and SLAM LSK cells in mobilized peripheral blood. Numbers indicate the percentage of gated cells within the total number. Right: Data are expressed as number of LSK and SLAM LSK cells per $10^6$ peripheral blood mononuclear cells. Data shown are pooled data from two independent experiments with four to five mice per group. The data shown are the mean±SD. *p<0.05. (G) Mice (B6) were injected s.c. once daily with UDP-Glc (200 mg/kg, 6 days) or G-CSF (300 µg/kg, 4 days). Mononuclear cells obtained from the peripheral blood of UDP-Glc injected mice (n>15) or G-CSF injected mice (n>12) were stained for CD150+CD48− (SLAM) LSK cells. Equal numbers of sorted peripheral CD45.1+ SLAM LSK (derived from G-CSF-mobilized PB) and CD45.2+ SLAM LSK (derived from UDP-Glc-mobilized PB) cells were transplanted into lethally irradiated recipient animals. After 6-8 weeks, their bone marrow cells were transplanted into lethally irradiated secondary and tertiary recipients. Two months later the peripheral blood (lower left panel) and bone marrow (lower right panels) of the tertiary recipients (n=5) were analyzed for donor cell engraftment as described in E. The schema (top panel) shows the experimental flow. (H) The effect of UDP-Glc on cell cycle status of HSPCs was evaluated using LSK cells from control (vehicle-injected) or UDP-Glc-injected mice. Mice were injected once daily with UDP-Glc or PBS for 6 days as described above. The bone marrow (upper panel) and blood (lower panel) samples were pooled from each group (n>4) and stained for Ki67 and DAPI. LSK cells were pregated and further analyzed for their cell cycle status. Left: The fraction of cells in the respective cell cycle phases is indicated in percent. Right: The data shown are the mean±s.d. of three independent experiments with four to five mice per group. (I) Recipient animals were transplanted as described in FIG. 11A. Peripheral blood cells from recipients (n>3) were analyzed at 3-4 months post transplant. The differentiation potential of UDP-Glc- and G-CSF-mobilized cells was determined using CD11b and B220 as markers of myeloid and lymphoid lineages, respectively. (J) Lineage analysis of donor cells in the blood of recipients. At 5 months post-transplantation, peripheral blood mononuclear cells of the recipient mice were stained with the indicated lineage markers. Data are presented as the percentage of gated cells positive for each lineage marker. The data shown are the mean±SD of two independent experiments with three mice per group.

FIGS. 12A-12D. A combination of UDP-Glc and G-CSF has an improved mobilization efficacy over the use of each agent alone. (A) Schema of combinatorial administration schedule: G-CSF was injected daily for 4 consecutive days. UDP-Glc was injected daily for 6 consecutive days. Mice were sacrificed (day 0. SAC) and blood cells were further analyzed for hematopoietic stem progenitor cell activity. (B) Mice were treated as described in (A). Peripheral blood cells were collected from G-CSF- and UDP-Glc/G-CSF-injected mice and transplanted in equal numbers into lethally irradiated recipient animals. The contribution of donor cells in the peripheral blood of the recipient animals was assessed at the indicated times as described.  p<0.01. (C-D) Eighteen weeks after transplantation, bone marrow cells were obtained from recipient animals (n=5) and analyzed by flow cytometry for LSK (4C) and SLAM LSK (4D) cells. Data are expressed as number of LSK and SLAM LSK cells per $10^5$ lineage-negative cells. The data shown are the mean±SD.  p<0.01.

FIG. 13A-13J. UDP-Glucose increases mitochondrial ROS levels and promotes a transient osteoclast differentiation. (A) Mice were injected with UDP-Glc or UDP-Glc/G-CSF as described in FIG. 12A. Lineage negative bone marrow cells (first row) were further gated (second row) to identify LSK cells. The cellular levels of mitochondrial superoxide were determined using MitoSOX-red within LSK cells (third row). Numbers indicate the percentage of gated cells. Data are representative of at least four mice analyzed individually per treatment group. (B) Mice were injected with UDP-Glc as described above. Bone marrow cell lysates were analyzed by Western blotting for RANKL expression. Values above each band represent fold difference in RANKL expression relative to control sample (CTL, vehicle injected) after normalization to β-actin loading control, as determined by densitometry. (C-D) Mice were treated as above. The femurs were sectioned longitudinally and immunostained with an antibody to RANKL (C). Tissue sections were also stained for tartrate-resistant acid phosphatase (TRAP) activity (D). Arrowheads (black color) indicate TRAP-positive cells. A representative TRAP staining is shown. Scale bar, 50 µM. (E) Bone marrow cells were pretreated with M-CSF and then further incubated with the indicated concentration of UDP-Glc. TRAP-positive cells were counted from at least three wells per treatment group. (F-G) Mice (n>4 per each group) were treated with NAC as described in Material and Methods. Note that UDP-Glc-mediated LSK and SLAM LSK cell mobilization was significantly suppressed by NAC treatment. The data shown are the mean±SD. #p<0.05 and ##p<0.01 and ** p<0.01. (H-I) Mice were treated as described in FIG. 13F. RANKL expression was determined by Western blotting (H) and immunohistochemistry (I). In Western blot analysis, the numerical values represent the fold change in densitometry data (calculated as above). Scale bar, 50 µM. (J) Mice were treated as indicated. Arrowheads (black color) indicate TRAP-positive cells. A representative TRAP staining is shown. Scale bar, 50 µM.

FIG. 14A-14F. Role of osteoclasts in UDP-Glc-mediated HSPC mobilization. (A) Osteopetrotic (op/op) mutant mice (n=6 per treatment group) and their littermate wild-type controls (n=10 per treatment group) were treated with either vehicle (CTL) or UDP-Glc. Mice were treated with UDP-Glc in the same dosage and schedule as described above. HSPC mobilization was assessed by measuring the numbers of LSK (upper left panel) and SLAM LSK (upper right panel) cells in peripheral blood. Mice were individually analyzed for each group, and the mean±SD is shown. $*p<0.05$ and $** p<0.01$ Representative images of TRAP staining from each group are shown (bottom panels). (B) P2X7 (P2rx7−/−) KO and their littermate wild-type (P2rx7+/+) controls were treated with either vehicle (CTL) or UDP-Glc as described above. HSPC mobilization was assessed as described in A. Mice were individually analyzed for each group (n=10/treatment group), and the mean±SD is shown. $*p<0.05$ and $ p<0.01$. Representative images of TRAP staining from each group are shown (bottom panels). Osteoclasts are already present at high numbers at about six weeks of age P2rx7−/− KO mouse. Shown are obtained from 6-8 weeks old animals. (C) Mice (B6) were injected as described in the legend to FIG. 11A. Bone marrow cells were collected from each treatment group and stained with indicated antibodies followed by flow cytometry analysis. The data are shown as mean values of three independent experiments with standard deviation. $ p<0.01$. (D) Bone marrow mononuclear cells were isolated from B6 mice treated as above. To determine the protease activity, bone marrow supernatants harvested from indicated treatment groups were analyzed by zymogram analysis as described in the Methods section. The intensity of the zymogram bands (left panels) was analyzed utilizing densitometry and expressed as arbitrary units (right panels). Densitometric analyses are represented as the ratios to vehicle-treated group (CTL) set to 1. Similar results were observed in three independent experiments. $*p<0.05$ and $** p<0.01$. (E) Mice were treated as described in the legend to FIG. 13F. Expression levels of CXCR4 were determined in bone marrow (upper panel) and peripheral blood (lower panel) cells after gating on LSK or SLAM LSK subsets. Data are expressed as mean±SD from at least two independent experiments with four mice per group. (F) Mice (n=7/group) were treated with UDP-Glc or UDP-Glc/NAC as described in E. Peripheral blood cells (CD45.2) were collected and injected i.v. into recipient mice (CD45. 1.2) ($6\times10^6$/mouse). Recipient mice were conditioned (11 Gy) 24 hours before injection of cells. Animals were sacrificed 12-14 hours after injection of cells. Mononuclear cells obtained from recipient bone marrow were analyzed for expression of donor cell marker (CD45.2). CD45.2+ cells were gated and analyzed for the presence of LSK cells. The data shown are the mean±SD. $*p<0.05$ FIG. 15A-15B. The relationship between UDP and UDP-Glucose in regulating HSPC migration. (A) Mice (B6) were given a subcutaneous injection with UDP (200 mg/kg), UDP-Glc (200 mg/kg) and the combination of these two factors. LSK cell mobilization was assessed as described above. Mice were individually analyzed for each group (n=5 per treatment group), and the mean±SD is shown. $*p<0.05$ and $** p<0.01$. (B) Chemotaxis assays were performed essentially as described in the FIG. 9E legend. Lineage depleted (Lin-) bone marrow cells from B6 mice were placed in the upper well ($10^6$/well). UDP (10 µM), UDP-Glc (10 µM), or the combination of UDP and UDP-Glc (10 µM/each) was placed to the lower wells. All cells that migrated to the lower wells were collected and stained for Sca-1 and c-Kit. Results are a summary of two independent experiments, each with duplicate wells per treatment condition. $*p<0.05$ and $** p<0.01$.

Figure 16:
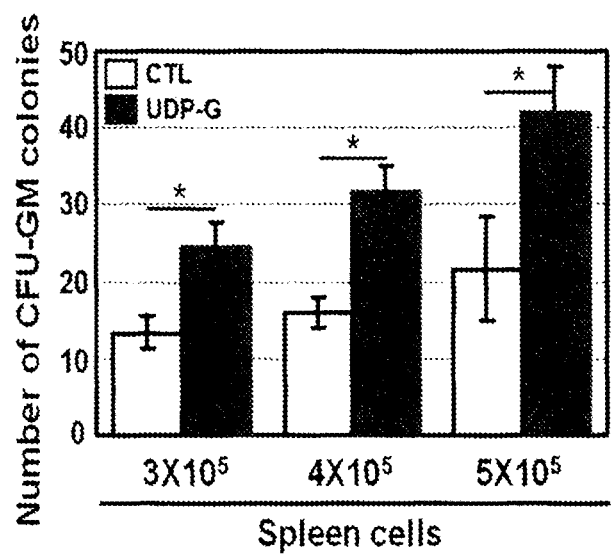
Figure 16:
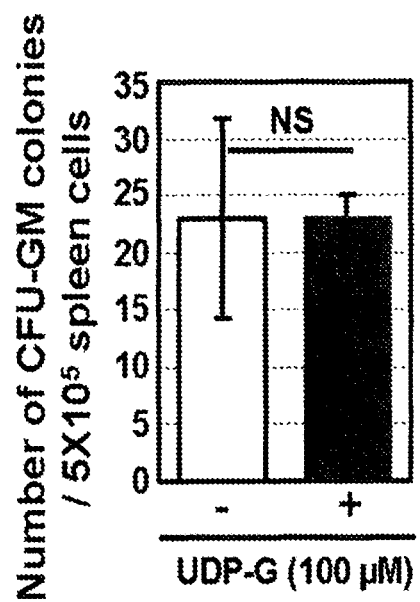

FIG. 16. (Left panel) number of CFU-GM colonies detected after administration of UDP-glucose versus control (CTL) where different numbers of spleen cells were used in different assays. (Right panel) Number of CFU-GM colonies per $5\times10^5$ spleen cells, where 100 µM UDP-G was added to the assay.

Figure 17:
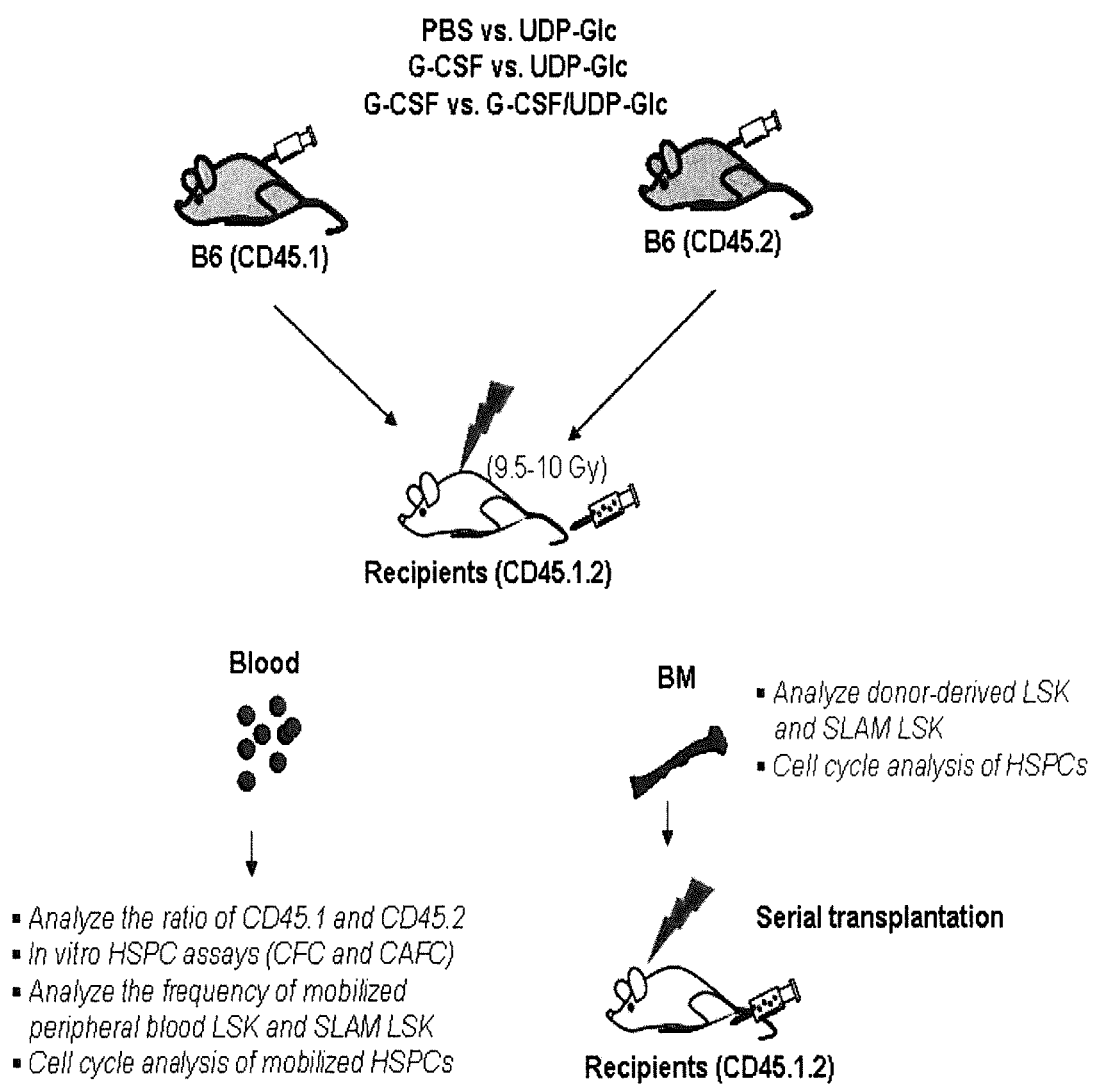

FIG. 17. Schematic showing protocol for competitive repopulation assays, where blood cells from either control or treated mice were transplanted into conditioned recipient mice.

Figure 18:
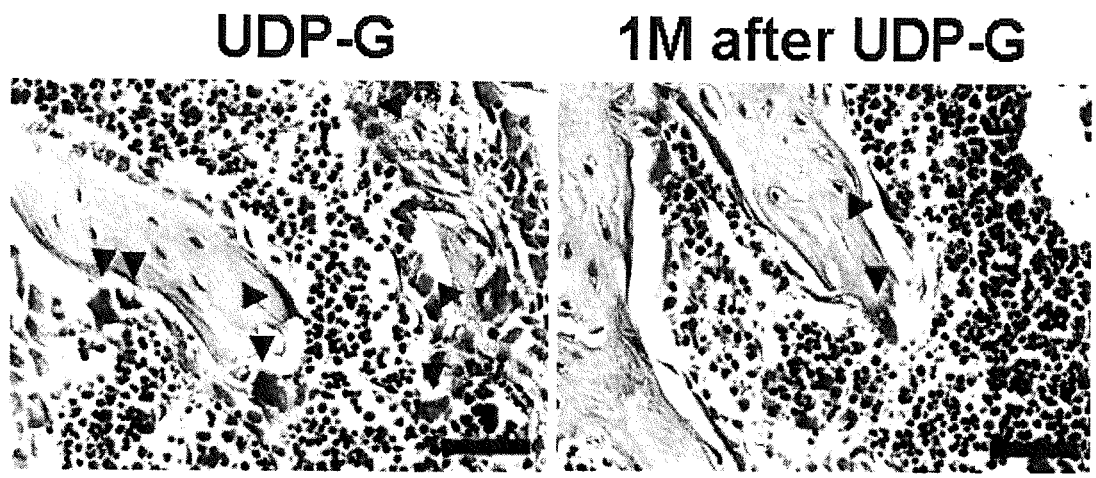

FIG. 18. Effect of UDP-G on cellularity of bone marrow, during treatment (left panel) and one month after treatment (right panel FIG. 19. Effect of UDP-G on spleen weight, relative to normal control.

5. DETAILED DESCRIPTION OF THE INVENTION

For clarity and not by way of limitation, this detailed description is divided into the following subsections:
(i) UDP compounds;
(ii) non-UDP HPC mobilizing compounds;
(iii) pharmaceutical compositions; and
(iv) methods of use.

5.1 UDP Compounds

UDP compounds include UDP-glucose (UDP-Glc), UDP-galactose (UDP-Gal), UDP-N-acetylglucosamine (UDP-GlcNAc), UDP-glucuronic acid, UDP, P536 (Alcino et al., "Activity of P536, an Analog of UDP-Glucose, Against *Trypanosoma cruzi*," Antimicrob. Agents and Chemother. 32(9), 1412-1415, 1988), UDP-6S-6C-methylglucose and UDP-6R-6C-methylglucose (Campbell and Tanner, "UDP-Glucose Analogues as Inhibitors and Mechanistic Probes of UDP-Glucose Dehydrogenase," J. Org. Chem., 64(26), 9487-9492, 1999), MRS 2690 (a P2Y14 receptor agonist available from Tocris. Co.), competitive antagonists of UDP-glucose set forth in Fricks et al., "UDP Is a Competitive Antagonist at the Human P2Y14 Receptor," J. Pharmacol. Exp. Ther. 325(2), 588-594 (2008), and UDP-containing compounds that inhibit UDP-Glc-mediated calcium signaling in the fluorometric imaging plate reader assay set forth in Hamel et al., J. Biomol. Screen. 16 (9), 1098-1105 (2011) (including compound A, described therein). A mixture of any two or more of the above may also be administered and is within the scope of "UDP compound".

The present invention provides for a pharmaceutical composition comprising a UDP compound, together with a suitable pharmaceutical carrier. In one non-limiting embodiment, the pharmaceutical composition is formulated for subcutaneous administration, for example having a pH of between about 5 and 8 and optionally containing a suitable pharmaceutical buffer.

5.2 Non-UDP HSPC Mobilizing Compounds

An HSPC mobilizing compound is a compound that promotes a mobilization or relocation of hematopoietic stem progenitor cells such as HSPCs from the bone marrow to the peripheral circulation in a subject. Non-limiting examples of HSPC mobilizing compounds that are not UDP compounds include G-CSF, poly-(1,6)-β-D-glucopyranosyl-(1,3)-β-D glucopyranose (PGG) β-glucan (Cramer et al., "Mobilization of Hematopoietic Progenitor Cells by Yeast-Derived β-Glucan Requires Activation of Matrix Metalloproteinase-9," Stem Cells 26, 1231-1240, 2008), AMD3100 (Cashen et al., "AMD3100: CXCR4 antagonist and rapid stem cell-mobilizing agent," Future Oncol. 3 (1):19-27, 2007), cyclophosphamide, fucoidan, and mixtures thereof.

5.3 Pharmaceutical Compositions

In non-limiting embodiments, the present invention provides for pharmaceutical compositions for use in a method of mobilizing or relocating hematopoietic progenitor cells such as HSPCs from the bone marrow into the peripheral circulation of a subject in need of such treatment, comprising administering to the subject a UDP compound, a non-UDP HSPC mobilizing compound, and a combination thereof. UDP compounds and non-UDP HSPC mobilizing compounds are set forth in the preceding sections.

In certain non-limiting embodiments, the pharmaceutical composition may comprise one or more UDP compounds selected from the group consisting of UDP, UDP-glucose, UDP-galactose, UDP-N-acetylglucosamine, UDP-glucuronic acid, P536, UDP-6S-6C-methylglucose, UDP-6R-6C-methylglucose, MRS 2690, and mixtures thereof.

In a further non-limiting embodiment, the pharmaceutical composition may comprise one or more UDP compounds, as described above, and one or more non-UDP HSPC mobilizing compounds, selected from the group consisting of G-CSF, poly-(1,6)- -D-glucopyranosyl-(1,3)- -Dglucopyranose (PGG)-glucan, AMD3100, cyclophosphamide, fucoidan, and mixtures thereof.

In certain non-limiting embodiments, the pharmaceutical composition may also contain one or more pharmaceutically acceptable carriers and excipients which can be in solid or liquid form.

5.4 Methods of Use

The present invention provides for a method of mobilizing or relocating (or promoting mobilization or relocation of) hematopoietic progenitor cells such as HSPCs (including HSPCs of lymphoid lineage) from the bone marrow into the peripheral circulation of a subject in need of such treatment, comprising administering, to the subject, an effective amount of a UDP compound, as described above.

The subject may be a human or non-human subject. The subject may be in need of such treatment in view of an anticipated, contemporaneous or past bone marrow toxic event such as radiation or chemotherapy or other toxic exposure (or to rescue people from radiation accidents or terrorist attack (dirty bomb)). The subject may be in need of such treatment in view of a desire to collect HSPCs from the peripheral circulation of the subject for the purpose of transplantation, where the transplantation may be autologous or allogeneic. In one non-limiting embodiment, the subject is being prepared to donate hematopoietic stem progenitor cells. In one non-limiting embodiment, the subject is a chemotherapy patient. In one non-limiting embodiment, the subject suffers from lymphopenia. In non-limiting embodiments, the subject may suffer from long term bone marrow failure (BMF) or Fanconi's anemia (FA).

The UDP compound may be administered by any suitable route, including but not limited to subcutaneous, intramuscular, intravenous, intraperitoneal, oral, rectal, or any other route known in the art.

In certain non-limiting embodiments, the UDP compound may be administered once a day, once every other day, once every third day, or once a week, or twice a day, twice every other day, or twice a week, during the treatment period.

In certain non-limiting embodiments, the treatment period may be 1 day, 2 days, 3 days, 4 days, 5 days, 6 days, one week, 8 days, 9 days, 10 days, 11 days, 12 days, 13 days, two weeks, 15 days, 16 days, 17 days, 18 days, 19 days, 20 days, three weeks, or one month, or between 3 and 14 days, or between 3 and 10 days, until a target level of HSPCs in the peripheral circulation has been reached. The treatment period may optionally be repeated after an interval of non-treatment, said interval of non-treatment being, in certain non-limiting embodiments, be 1 day, 2 days, 3 days, 4 days, 5 days, 6 days, one week, 8 days, 9 days, 10 days, 11 days, 12 days, 13 days, two weeks, 15 days, 16 days, 17 days, 18 days, 19 days, 20 days, three weeks, one month, 5 weeks, 6 weeks, or until a triggering event, such as the administration of chemotherapy, occurs.

In certain non-limiting embodiments, the UDP compound may be administered as part of a regimen with one or more other non-UDP compound HSPC mobilizing compounds. The UDP compound and the other HSPC mobilizing compound may be administered concurrently or at different times over a period when they each can have an effect on the bone marrow (for example, function complementarily).

In non-limiting embodiments, the UDP compound is administered at a dosage of 0.1-500 mg/kg or at a dosage of 1-100 mg/kg or at a dosage of 0.1-20 mg/kg or at a dosage of 0.01-1 mg/kg. In one non-limiting embodiment, the UDP compound is UDP-glucose, administered to a human at a dosage of 1-100 mg/kg or at a dosage of 0.1-20 mg/kg. In one non-limiting embodiment, the UDP compound is UDP-glucose, administered to a human at a dosage of 0.01-300 mg/kg or at a dosage of 1-100 mg/kg or at a dosage of 0.1-20 mg/kg or at a dosage of 0.01-1 mg/kg.

In one non-limiting embodiment, UDP-glucose or UDP is administered to a subject daily over a treatment period between 3 and 10 days. In one non-limiting embodiment, UDP-glucose or UDP is administered to a human subject daily over a treatment period between 3 and 10 days. In one non-limiting embodiment, UDP-glucose or UDP is administered to a human subject, subcutaneously, daily over a treatment period between 3 and 10 days.

In one non-limiting embodiment, UDP-glucose or UDP is administered as part of a treatment regimen with G-CSF, where the two agents are administered simultaneously or not simultaneously, but where they are both administered over the treatment period. In non-limiting embodiments, G-CSF may be administered subcutaneously either as a bolus or by continuous infusion or by any other route used in the art for administering G-CSF. In non-limiting embodiments, G-CSF may be administered at a daily dose of between 1 and 15 micrograms/kg per day or between 1 and 10 micrograms/kg per day or 5 or 10 micrograms/kg per day, for example but not by way of limitation, once a day, once every other day, once every third day, or once a week, or twice a day, twice every other day, or twice a week, during the treatment period. Preferably G-CSF is given in at least four consecutive daily injections (Broxmeyer et al., "Rapid mobilization of murine and human hematopoietic stem and progenitor cells with AMD3100, a CXCR4 antagonist," J. Exp. Med. 201, 1307-1318, 2005) although other regimens may be used. For example, but not by limitation, the treatment period may be daily treatment for 5 consecutive days, 6 consecutive days or 7 consecutive days. In one non-limiting embodiment, G-CSF treatment is started 1, 2 or 3 days after the first administration of UDP compound. In other non-limiting embodiments where UDP-glucose and UDP are administered in a treatment regimen with G-CSF, G-CSF may be administered at a daily dose of between 0.01 and 120 micrograms/kg/day, or between 5 and 20 micrograms/kg per day, for example but not by way of limitation, once a day, once every other day, once every third day, or once a week, or twice a day, twice every other day, or twice a week, during the treatment period.

6. EXAMPLE 1

6.1 Materials and Methods

Animals and Treatment.

We used 4-6 weeks old C57BL6 and BALB/C in all the experiments. Mice received subcutaneous injections of UDP-glucose (200 mg/kg, Sigma) dissolved in sterile endotoxin-free PBS. G-CSF (Neupogen, Amgen) was administered daily at a dose of 300 µg/kg subcutaneously for 4 consecutive days as previously described (Broxmeyer et al., 2005). For the combination group, mice were injected UDP-Glc at 200 mg/kg subcutaneously for 6 consecutive days (from day 0 to day 5), accompanied by 300 µg/kg subcutaneous injections of G-CSF (from day 2 to day 5). Antioxidant, N-acetyl-L-cysteine (Sigma-Aldrich), was administered subcutaneously at 100 mg/kg/day. Bone marrow cells were obtained from both femur and tibia and used for flow cytometry and Western blot analysis. All animal studies were conducted after review by the University of Pittsburgh's Institutional Animal Care and Use Committee and in accordance with the University of Pittsburgh's Policy on the Care, Welfare and Treatment of Laboratory Animals.

Colony Forming Cell (CFC) Assay and Cobblestone Area Forming Cell (CAFC) Assay.

Mobilized mononuclear peripheral blood cells ($1\times10^6$) and spleen cells ($0.5\times10^6$) were seeded for CFC assay. The number of BFU-E, CFU-GM and CFU-GEMM colonies was counted using standard criteria. CAFC assay was performed in duplicate using MyeloCult M5300 (StemCell Technologies) as described previously (Ploemacher et al., 1989). After 5 weeks, wells containing cobblestone areas were counted as positive wells.

Transplantation.

For competitive repopulation assays, an equal number of peripheral blood cells mobilized by each agent (PBS vs. UDP-Glc; UDP-Glc vs. G-CSF; G-CSF vs. UDP-Glc/G-CSF) were transplanted into conditioned recipient mice (CD45.1.2., 9.5-10Gy). Although we used CD45 congenic animals (B6) in competitive repopulation assay, in order to confirm that our results are not due to potential variability resulting from the disparity between the CD45.1 and CD45.2, the results were further confirmed by injecting mobilizers the other way around (ex; inject G-CSF into CD45.1 and UDP-Glc to CD45.2 mice, and vice versa). The ratio of CD45.1/CD45.2 cells in recipient's peripheral blood was determined at various times after transplantation.

Flow Cytometry Analysis.

The relative contributions of UDP-Glc, G-CSF, and UDP-Glc/G-CSF-mobilized peripheral blood cells to recipient blood and bone marrow were assessed by flow cytometry analysis using anti-CD45.1 and anti-CD45.2 antibodies (eBioscience). Peripheral blood Lin-/Sca-1+/c-Kit+(LSK) and CD150+CD48-(SLAM) LSK cells were phenotyped using the following antibodies: lineage markers PE-Cy7-conjugated anti-CD3, anti-CD4, anti-CD8, anti-CD45R, anti-CD11b, anti-Gr-1, and anti-TER-119 (eBioscience); PE-conjugated anti-Sca-1 (eBioscience); APC-conjugated anti-c-Kit (eBioscience); perCP/Cy5.5-conjugated anti-CD150 (BioLegend); pacific Blue™-conjugated anti-CD48 (BioLegend). The percentage of bone marrow LSK and SLAM LSK cells derived from UDP-Glc- and G-CSF-mobilized cells was analyzed among gated either the CD45.1 or CD45.2 compartment. Mitochondrial superoxide level was measured using MitoSox™ (Invitrogen) within LSK cells, according to manufacturer's instructions.

Western Blot Analysis.

Equal amounts (20 µg/sample) of protein extracts were loaded on 15% SDS-PAGE and blotted onto polyvinyl difluoride membranes. The blots were probed with primary antibody specific for goat polyclonal RANKL (Santa Cruz Biotechnology) and mouse monoclonal β-actin (Sigma-Aldrich) overnight at 4° C.

TRAP Staining and Immunohistochemistry.

Femurs dissected from treated mice were fixed in 4% paraformaldehyde solution in phosphate buffered saline (PBS, pH7.2) for 2 days and then decalcified in 10% EDTA (pH 7.5) for 10 days. After decalcification, they were embedded in paraffin and longitudinally cut to 5 µm thickness. For identification of osteoclasts, the sections were deparaffinized, dehydrated, and stained using TRAP staining kit (B-Bridge International, Inc.) according to the manufacturer's instructions. For immunohistochemical staining of RANKL, after dehydration, the sections were immunolabeled overnight with goat polyclonal antibody against mouse RANKL (Santa Cruz Biotechnology, 1:50) at 4° C. Subsequently, they were incubated with biotinylated goat-specific secondary antibody (Vector Laboratories) followed by DAB staining according to the manufacturer's instructions (Vector Laboratories).

Statistical Analysis.

All the data were expressed as the mean±standard deviation (SD). A one-way ANOVA was used for multiple comparisons using SPSS version 16.0 software. A P value <0.05 was considered statistically significant.

6.2 Results

UDP-Glc Promotes Mobilization of Hematopoietic Stem Progenitor Cells.

Figure 1C:
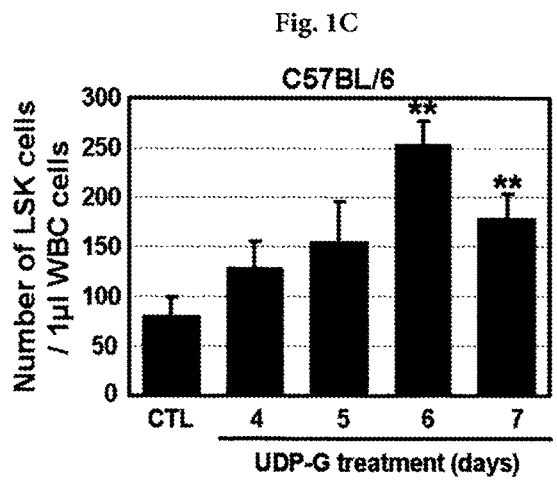
Figure 1D:
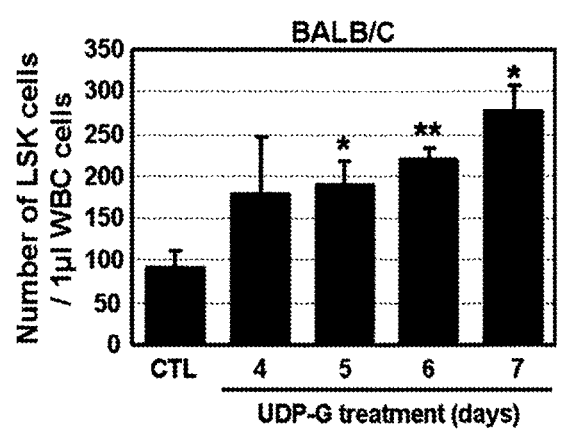
Figure 1E:
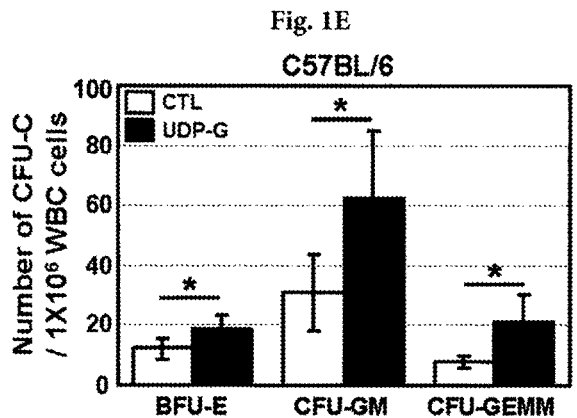
Figure 1F:
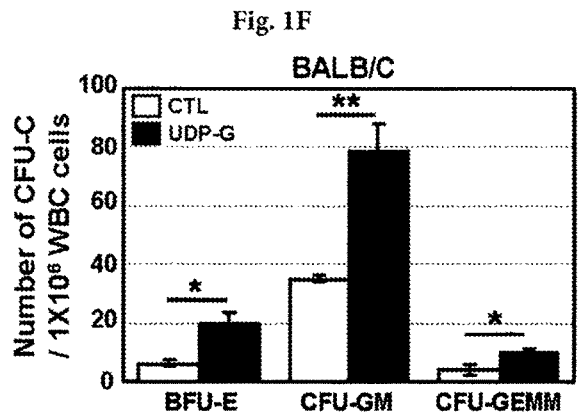

To test whether in vivo administration of exogenous UDP-Glc may mimic stress conditions and trigger HSPC mobilization, we injected UDP-Glc into mice and assessed its ability to mobilize HSPCs that are capable of forming colonies (CFU-Cs). Spleen cells from UDP-Glc-treated mice showed an increase in the number of CFU-GM (FIGS. 1A and 1B), suggesting that UDP-Glc led mobilization of CFU-Cs to extramedullary sites. In determining optimal dose, UDP-Glc exerted its maximal mobilizing effects at a dose of 200 mg/kg mouse body weight (FIG. 1A). Although i.v. administration was superior to s.c. or i.p. in mobilizing CFU-GM (FIG. 1B), s.c. injection was chosen for further studies to minimize potential side effects of i.v. injection and due to its simplicity. Since mobilized HSPCs are routinely harvested from the peripheral blood in the clinic, we quantified HSPCs (Lineage-Sca-1+c-kit+ cells, hereafter referred to as LSK) in the peripheral blood of UDP-Glc-treated mice. There was a notable increase in the frequency of LSK cells in the circulation after 6 daily single UDP-Glc injections (FIG. 1C). The mobilizing effect of UDP-Glc was also evident in BALB/C mice (FIG. 1D), demonstrating that mouse strain did not significantly influence the efficacy of UDP-Glc-induced HSPC mobilization. In line with this, UDP-Glc treatment led to a significant increase of CFU-Cs (CFU-GM, BFU-E, and CFU-GEMM) in the blood of both B6 and BALB/C mice (FIGS. 1E and 1F). These data demonstrate a previously unrecognized role of UDP-Glc in mobilizing HSPCs.

UDP-Glc Mobilizes Long-Term Repopulating Hematopoietic Stem Progenitor Cells.

Figure 2A:
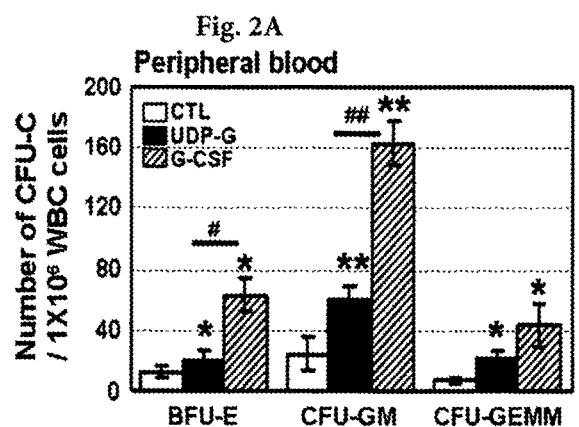
Figure 2B:
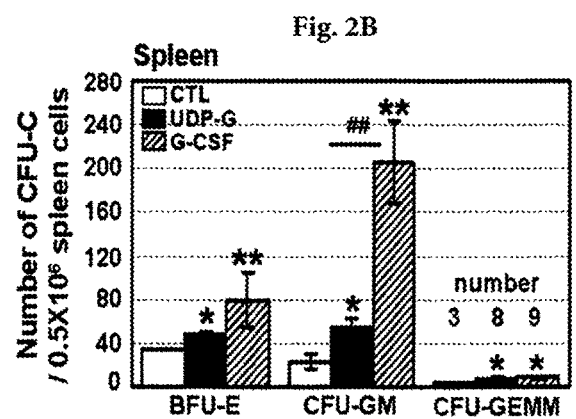
Figure 2C:
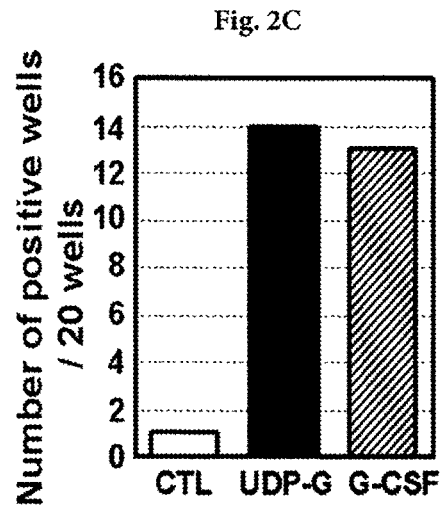
Figure 2D:
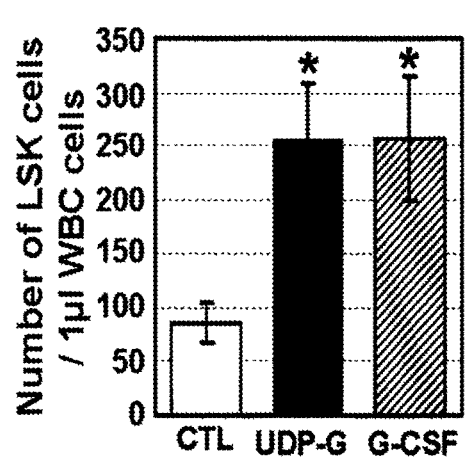
Figure 2E:
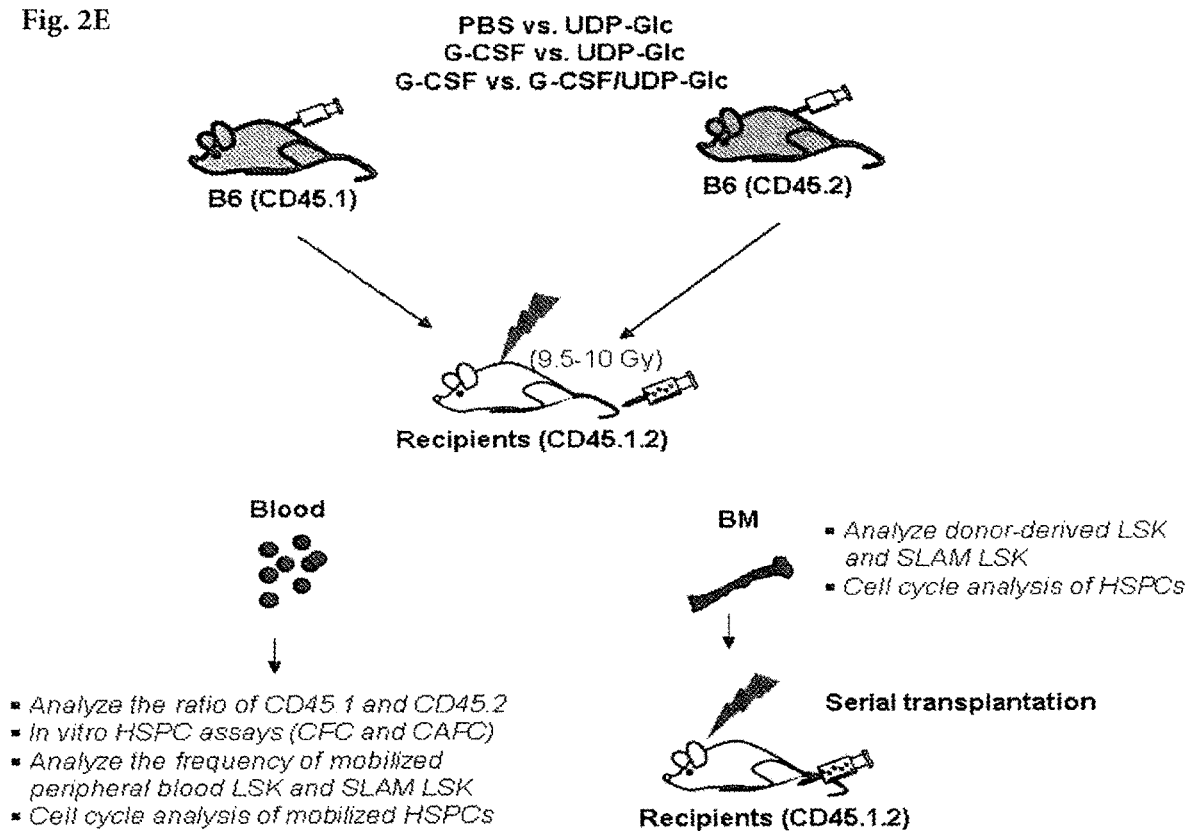
Figure 2F:
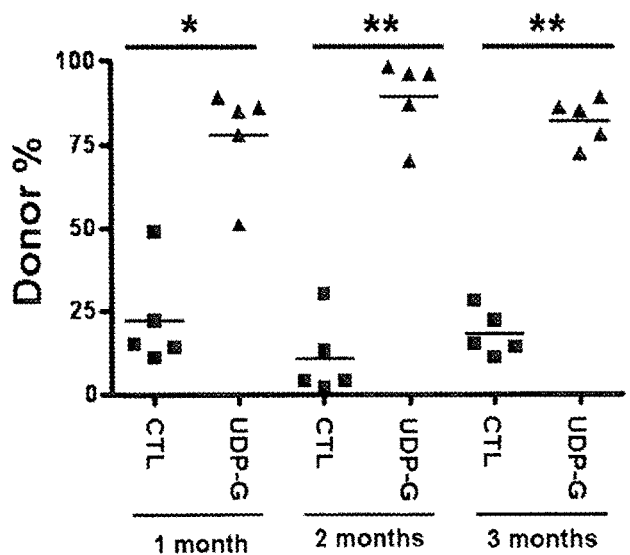

G-CSF is the most commonly used cytokine for mobilization of HSPCs in the clinic. We thus determined the mobilizing capability of UDP-Glc in comparison with G-CSF. G-CSF was administered as described in Broxmeyer et al., 2005 and Wright et al., 2001. UDP-Glc was significantly less efficient than G-CSF in mobilizing CFU-Cs to peripheral blood (FIG. 2A) and spleen (FIG. 2B). We then performed cobblestone area-forming cell assays (CAFC) to estimate the frequency of more primitive progenitor cells in UDP-Glc-mobilized blood. Interestingly, despite their low in vitro colony forming capacity, UDP-Glc-mobilized cells displayed high CAFC activity (approximately 10-14 fold higher than vehicle-injected group), which is similar to the fold increase observed with G-CSF-mobilized cells (FIG. 2C). UDP-Glc was also almost equally potent in mobilizing LSK cells into peripheral blood (FIG. 2D).

Neither phenotypic analysis nor in vitro HSPC assays necessarily accurately reflect stem progenitor cell activity in vivo (Park et al., 2008). To assess the functional properties of UDP-Glc-mobilized HSPCs in vivo, we performed competitive repopulation assays, where the equal number of blood cells, from either control or UDP-Glc-treated mice, was transplanted into conditioned recipient mice. UDP-Glc-mobilized cells showed a significant repopulation advantage compared to vehicle-treated blood cells over a 3-month period post-transplant (FIG. 2F), demonstrating the long-term repopulating potential of UDP-Glc-mobilized HSPCs. No animals transplanted with control blood cells alone survived lethal irradiation, consistent with a previous report (Neben et al., 1993). Of note, while UDP-Glc-mobilized cells provided a better radioprotection than vehicle-treated cells, they were unable to fully protect recipient animals from the effects of lethal irradiation.

Figure 2G:
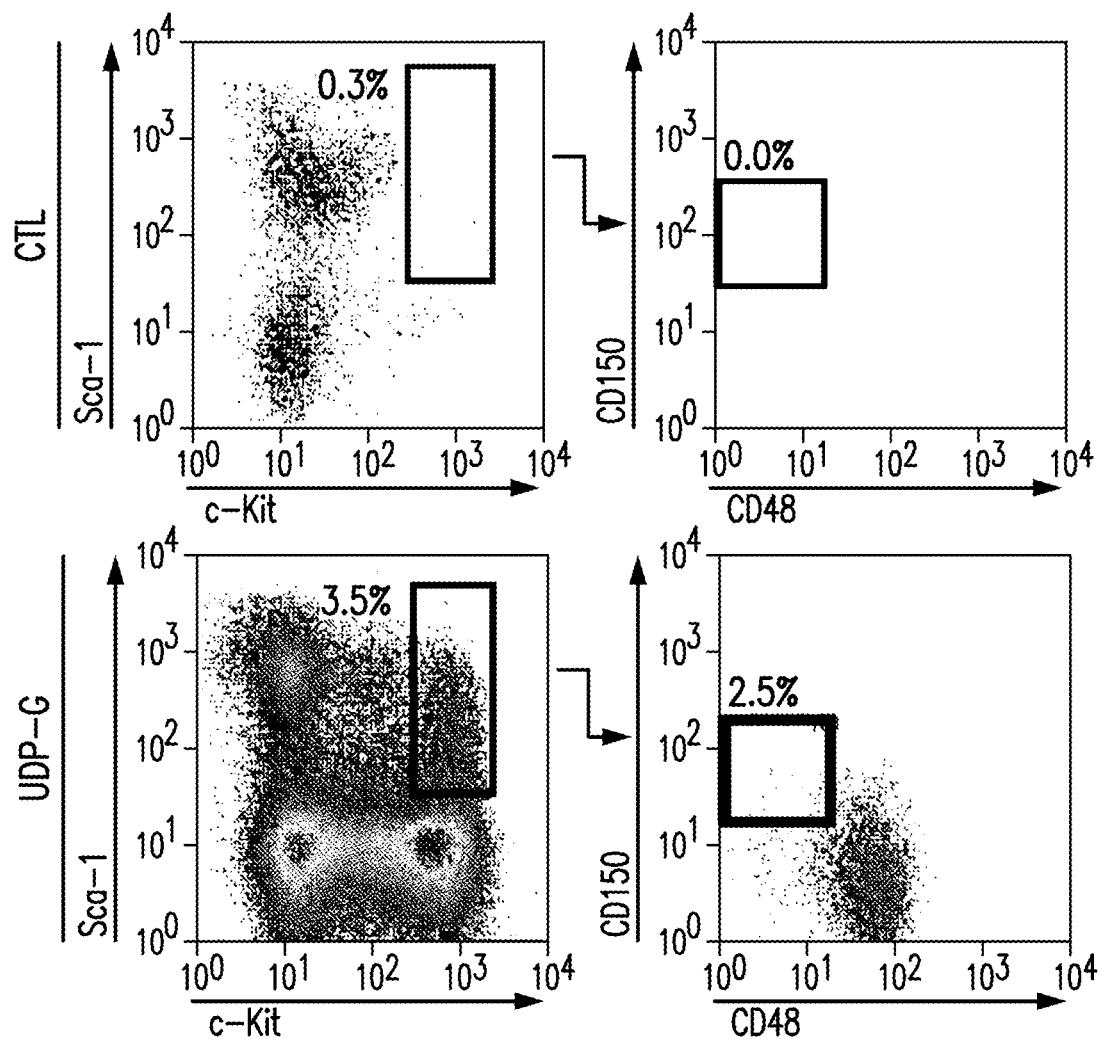
Figure 3A:
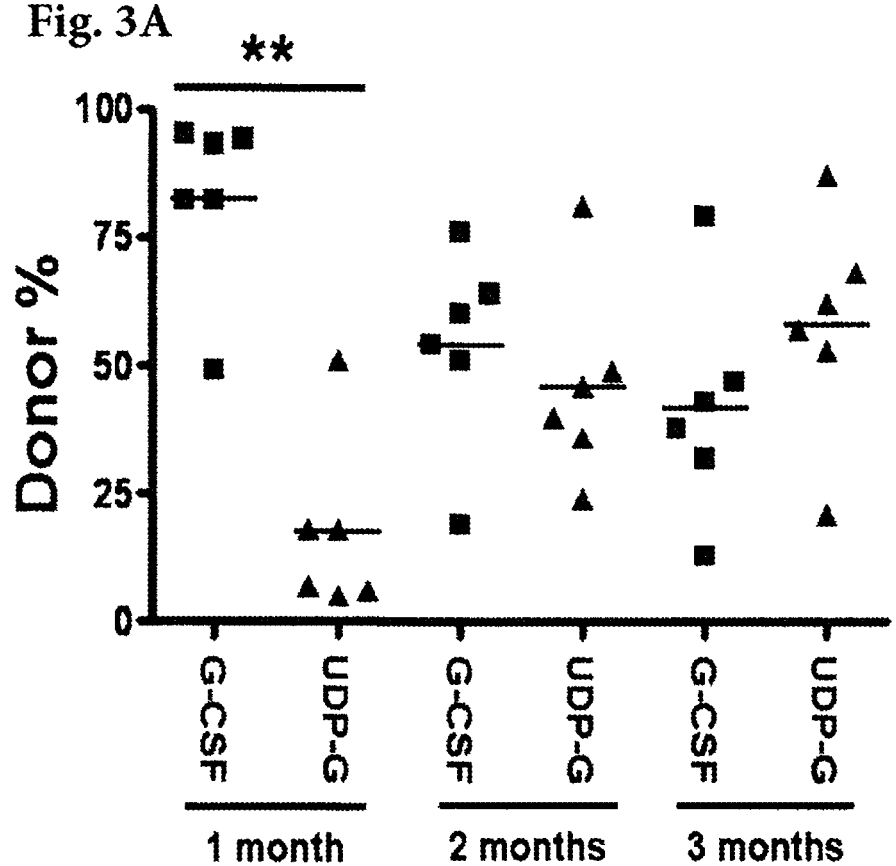
Figure 3B:
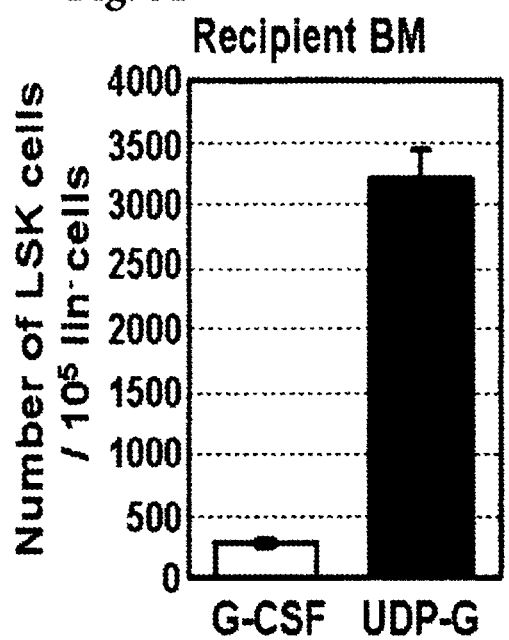
Figure 3C:
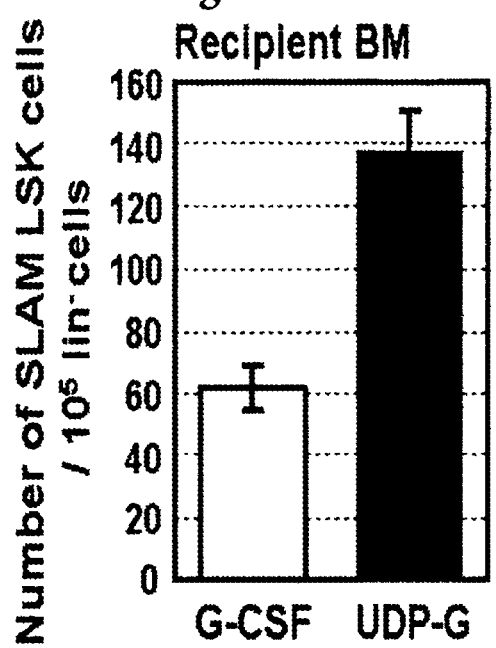
Figure 3D:
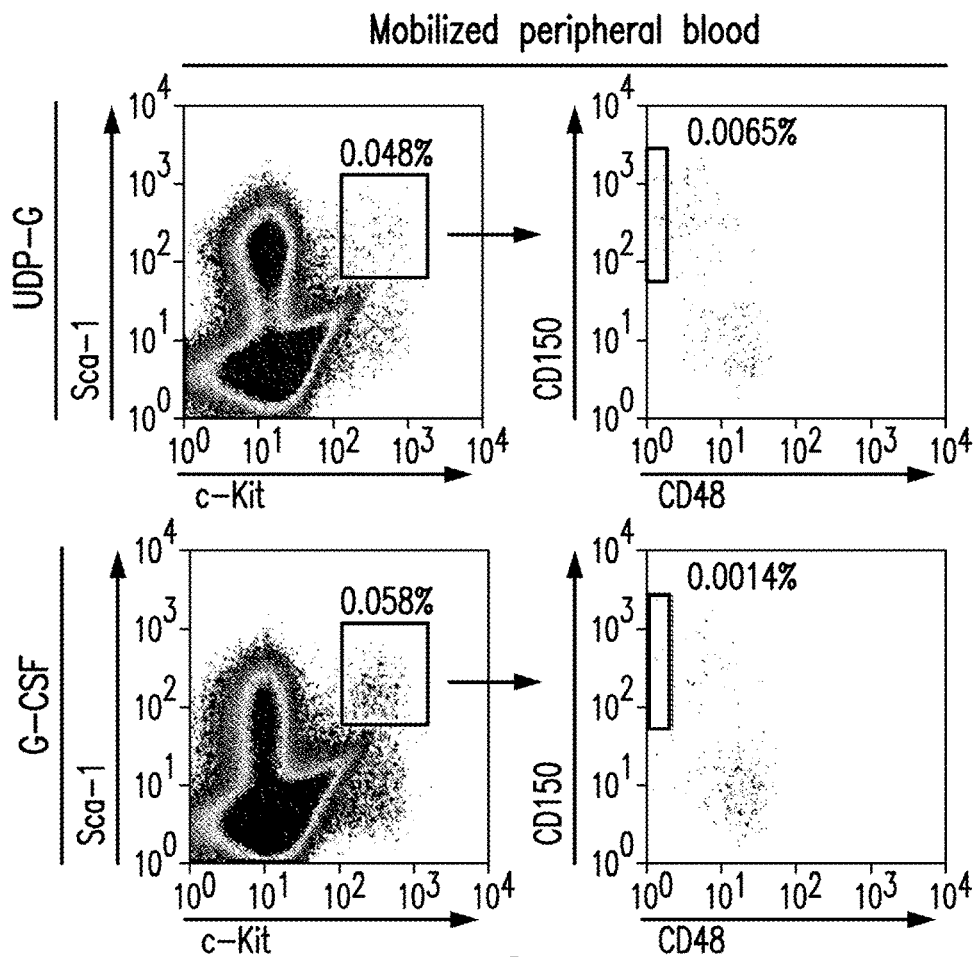
Figure 3E:
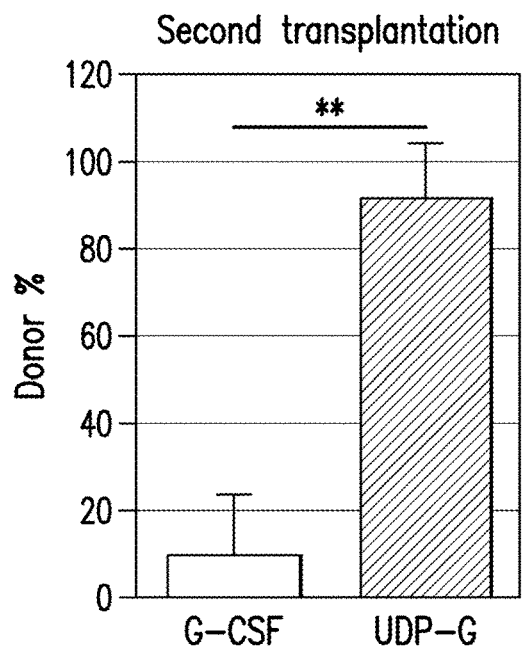
Figure 3F:
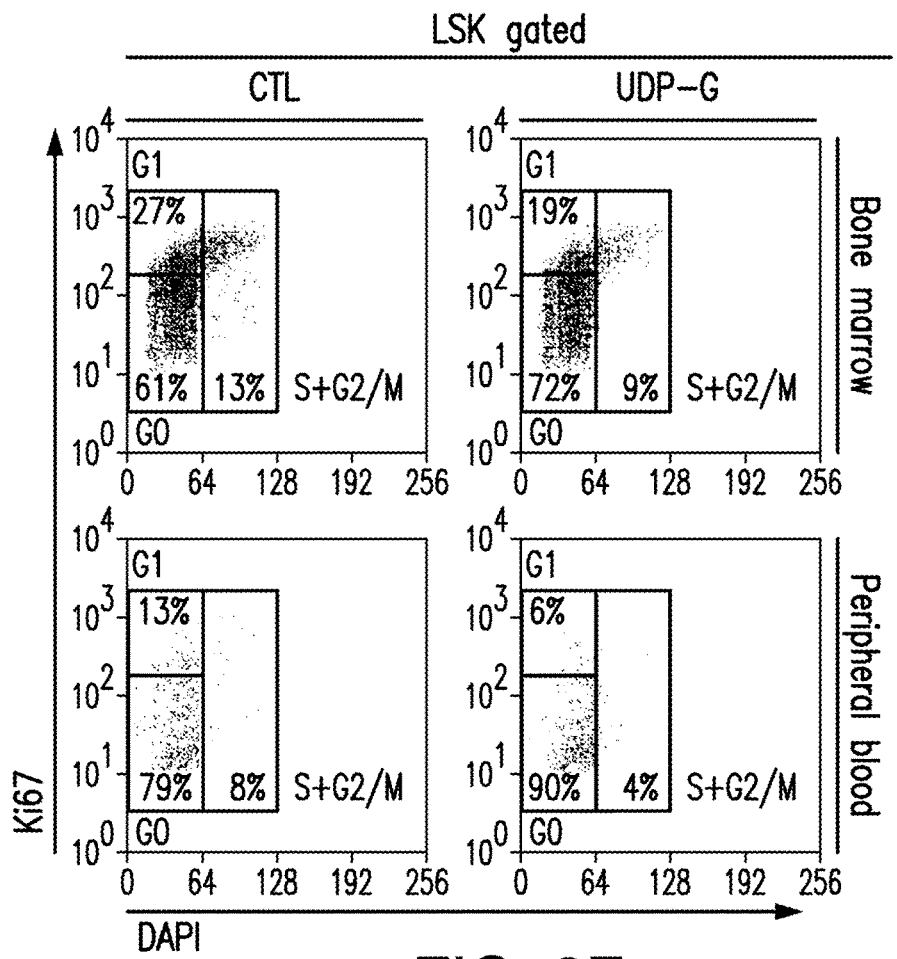
Figure 3G:
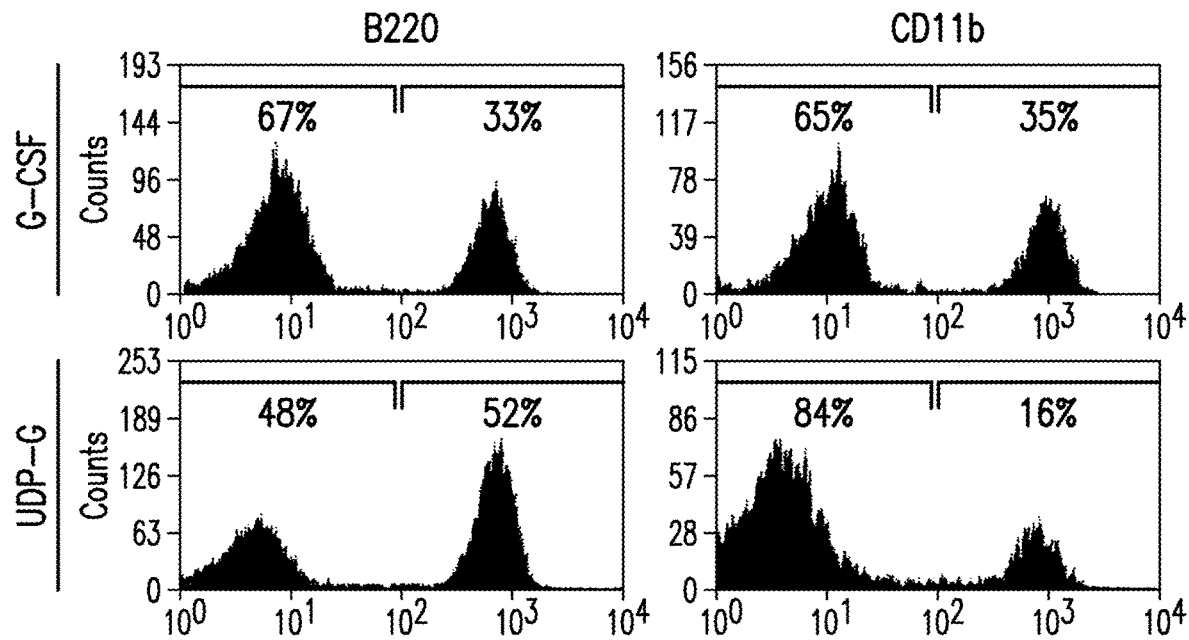

The maintenance of stem cell pool and generation of functional mature blood cells depend on close interaction with specialized microenvironments or niches in bone marrow (Purton and Scadden, 2006). Therefore, the engraftment of HSPCs to bone marrow more accurately represents clinical outcome in clinical protocols. We thus assessed whether donor-derived HSPCs are sustainable in the bone marrow of recipient animals for an extended period after transplantation. Sixteen weeks after transplantation, we could readily detect HSPC population (LSK and SLAM LSK cells) derived from UDP-Glc-mobilized cells in the bone marrow of recipient animals (FIG. 2G, lower panel). In contrast, HSPCs-derived from vehicle-treated mice were very low or undetectable (FIG. 2G, upper panel). In addition, UDP-Glc-mobilized cells were able to repopulate transplanted recipients with both myeloid and lymphoid cells (FIG. 3G, lower panel). Together, these findings demonstrate that UDP-Glc induces the mobilization of HSPCs that have the ability to engraft recipient animals and differentiate into multi-lineage cells.

UDP-Glucose Mobilizes Distinct Subsets of Hematopoietic Stem Progenitor Cells in Comparison with G-CSF.

Next, we compared the HSPC mobilizing capability of UDP-Glc with that of G-CSF using competitive repopulation assay. At one month following transplantation, G-CSF-mobilized cells displayed a considerable competitive advantage over UDP-Glc-mobilized cells (FIG. 3A). However, UDP-Glc-mobilized cells began to gain their abilities to compete with G-CSF-mobilized cells at 2 months post-transplant. Notably, UDP-Glc-mobilized cells became dominant and out-competed G-CSF-mobilized cells starting 3 months post-transplant (FIG. 3A), and sustained their competitive advantage thereafter.

We assessed whether this was because the recipient's bone marrow niches were predominantly occupied by UDP-Glc-mobilized cells. To this end, we analyzed the bone marrow of recipient animals at 18 weeks after transplantation. A significantly higher portion of LSK and SLAM LSK cells in recipient bone marrow were derived from UDP-Glc-treated mice at 18 weeks after transplantation (FIGS. 3B and 3C), indicating that UDP-Glc-mobilized cells achieved higher levels of long-term engraftment than G-CSF-mobilized cells.

The preferential engraftment of long-term repopulating cells with UDP-Glc-mobilized cells may indicate the possibility that UDP-Glc mobilizes a more primitive subset of HSPCs such as SLAM LSK cells than G-CSF. UDP-Glc promoted LSK cell mobilization into the peripheral blood, with efficacy similar to that of G-CSF (0.048% vs. 0.058%) (FIG. 3D, left panels). However, UDP-Glc-mobilized LSK cells contained a significantly higher proportion of SLAM LSK cells compared to that of G-CSF-mobilized cells (0.0065% vs. 0.0014%) (FIG. 3D, right panels).

Serial transplantation represents the gold standard for assessing the long-term repopulation abilities. In order to further compare the long-term repopulation abilities of UDP-Glc- and G-CSF-mobilized HSPCs, we performed serial transplantation experiments under competitive settings. Primary recipients were transplanted with UDP-Glc (CD45.2)- and G-CSF (CD45.1)-mobilized peripheral blood cells as shown in FIG. 3A. At 2-3 months post-transplant, bone marrow cells from primary recipients were sorted based on their expression of CD45. A mixture of equal numbers of CD45.1 (derived from G-CSF mobilization) and CD45.2 (derived from UDP-Glc mobilization) bone marrow cells were then transplanted into lethally irradiated secondary recipients. While G-CSF-mobilized peripheral blood cells have superior short-term repopulating ability in primary recipient animals (FIG. 3A), they were completely out-competed by the cells derived from UDP-Glc mobilization in the secondary recipients over the whole post-transplantation period (FIG. 3E). These data reinforce the hypothesis that UDP-Glc-mobilized HSPCs have enhanced self-renewal capacity when compared to G-CSF-mobilized HSPCs.

Administration of G-CSF promotes cell cycle entry by quiescent HSC in both mice and baboon (Steinman, 2002). Unlike G-CSF, UDP-Glc does not appear to function as a potent mitogen for HSPCs. Therefore, it is conceivable that UDP-Glc releases HSPCs from the niche without disruption of their cell cycle quiescence, and this may improve the long-term engraftment ability of UDP-Glc-mobilized HSPCs. Indeed, UDP-Glc did not result in significant changes in the G2/M or S phase of the cell cycle. Rather, UDP-Glc-treated mice showed an increased quiescent G0 fraction of HSPCs in their bone marrow (61% vs. 72%) (FIG. 3F, upper panels). We then analyzed the cell cycle profiles for UDP-Glc-mobilized peripheral blood HSPCs. A moderate decrease in S or G2/M phase was seen in UDP-Glc-mobilized peripheral blood HSPCs. In contrast, there was an increased proportion of peripheral blood HSPCs in G0 phase (79% vs. 90%) (FIG. 3F, lower panels).

It is also interesting to note that UDP-Glc-mobilized cells, as compared to G-CSF-mobilized counterparts, exhibited a differentiation pattern skewed toward the lymphoid lineage in recipient mice (FIG. 3G). Taken together, these data support the notion that UDP-Glc mobilizes a functionally distinct subset of HSPCs.

The Combination of UDP-Glc with G-CSF Improves Hematopoietic Stem Progenitor Cell Mobilization.

Figure 4A:
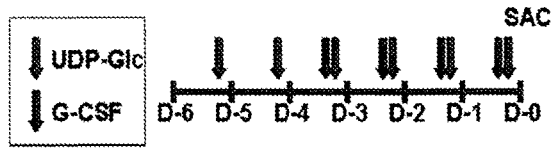
Figure 4B:
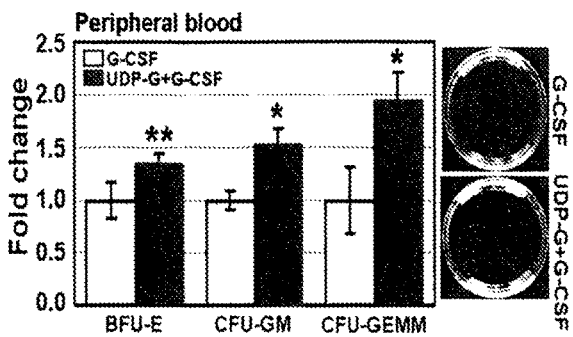
Figure 4C:
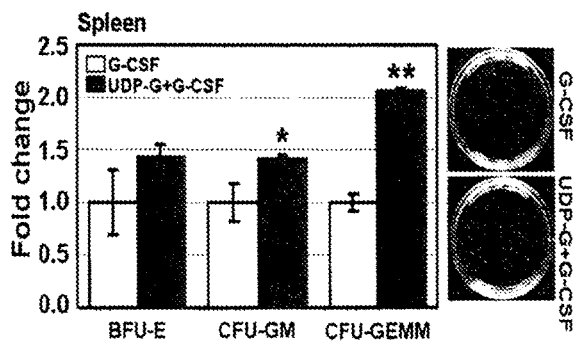
Figure 4D:
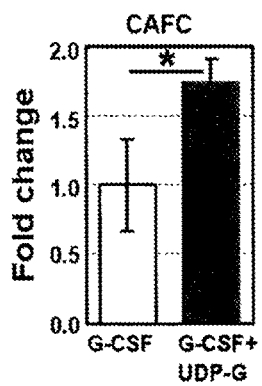
Figure 4E:
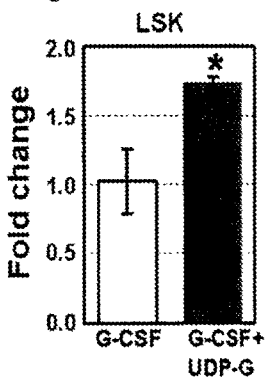
Figure 4F:
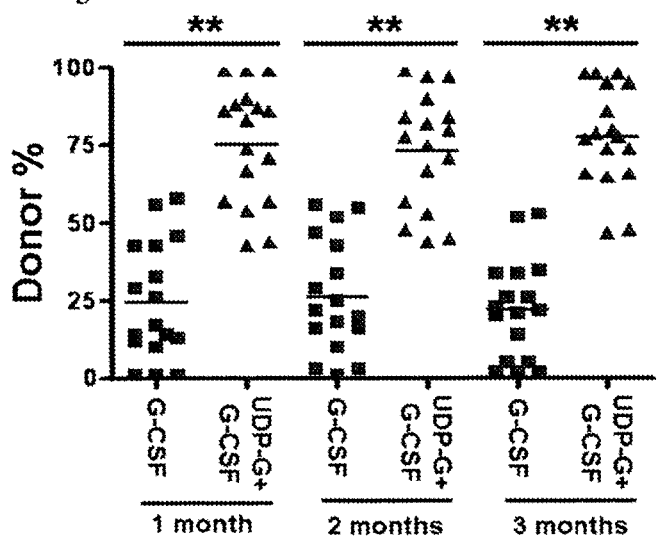

There is a keen interest in improving the mobilizing effects of G-CSF (Broxmeyer et al., 2005). Therefore, we investigated possible functional synergies between UDP-Glc and G-CSF. The mobilizing effect of UDP-Glc peaked 2-3 hours after the sixth daily consecutive injection (FIG. 1C). G-CSF is administered in at least four consecutive daily injections (Broxmeyer et al., 2005). Based on these results, the administration schedule of the compounds was designed to synchronize the maximal effect of each treatment as shown in FIG. 4A. We first assessed the effects of these regimens by assessing the colony forming activity. As shown in FIGS. 4B and 4C, the combination of G-CSF with UDP-Glc mobilized a significantly higher CFU-Cs to peripheral blood and spleen compared with G-CSF alone. CAFC activity was also highly enriched in UDP-Glc/G-CSF-treated cells (FIG. 4D), indicating that G-CSF, when combined with UDP-Glc, performed better in in vitro HSPC assays. Similarly, the combination of UDP-Glc and G-CSF was more efficient in mobilizing LSK cells than G-CSF alone (FIG. 4E). In the setting of competitive repopulation assay, UDP-Glc/G-CSF-mobilized cells were dominant over G-CSF-mobilized cells throughout the whole post-transplantation period (FIG. 4F). Although UDP-Glc alone was not as efficient as G-CSF in mobilizing in vitro colony forming HSPCs (FIGS. 2A and 2B) or in vivo short-term repopulating cells (FIG. 3A), a combination of UDP-Glc and G-CSF markedly enhanced short-term repopulating activity compared with G-CSF alone, and this competitive advantage was continued over at least 3 months after transplantation (FIG. 4F).

UDP-Glc Mobilizes Hematopoietic Stem Progenitor Cells Through the Alterations of the Osteoblast/Osteoclast Balance Mediated by ROS.

Figure 5A:
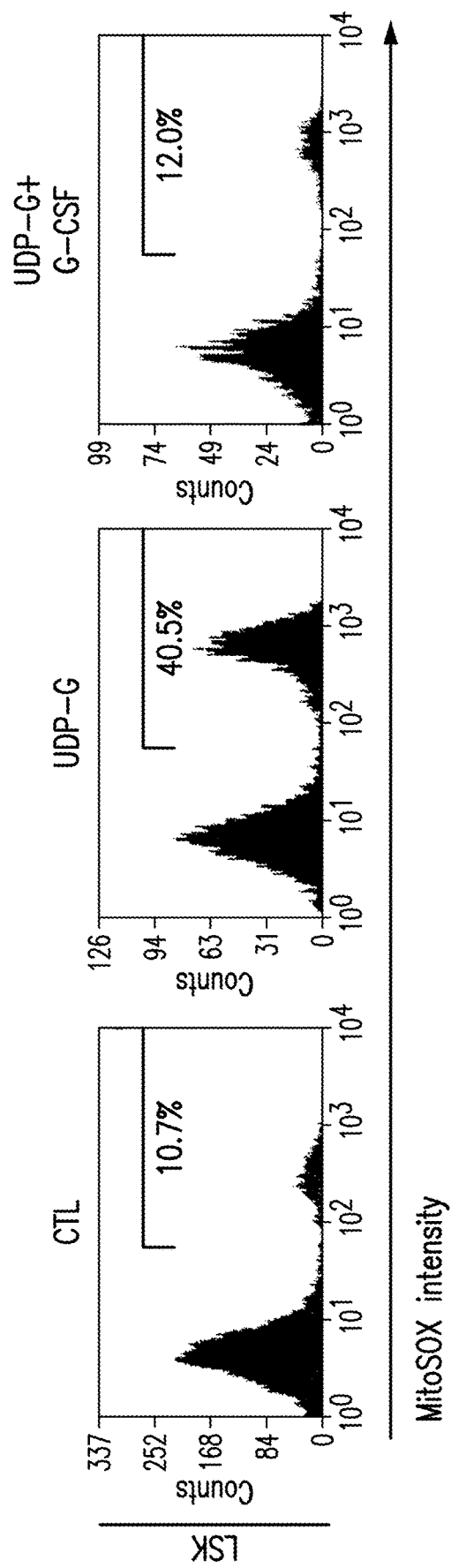
Figure 5B:
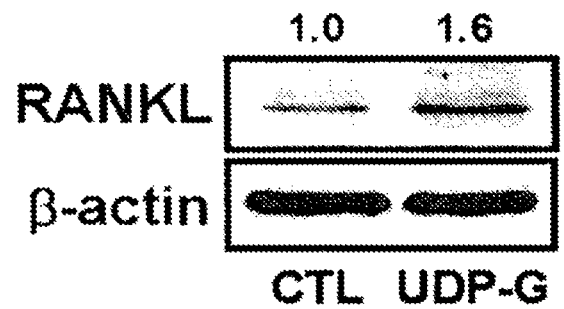
Figure 5C:
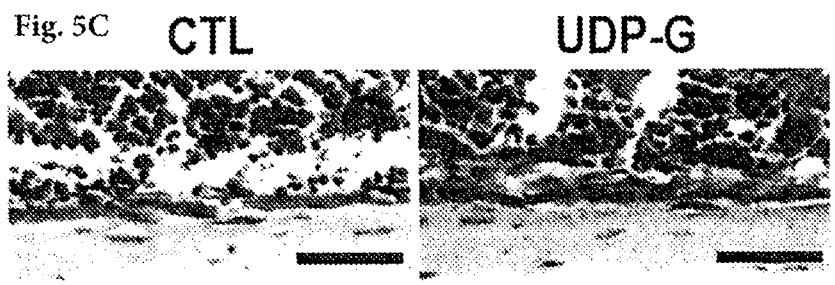
Figure 5D:
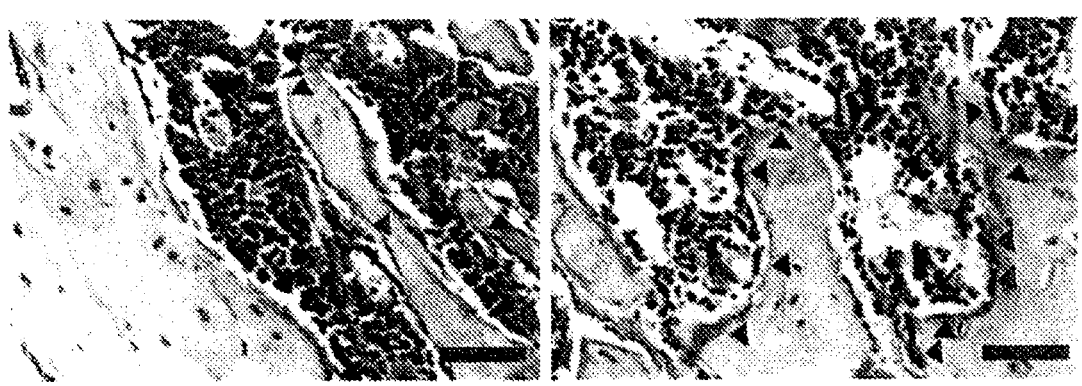

It has been recently proposed that Reactive Oxygen Species (ROS) signaling is closely associated with HSPC mobilization (Dar et al., 2011; Tesio et al., 2011). We therefore examined whether UDP-Glc modulates the level of intracellular ROS levels. Since mitochondria are a major source of ROS, we measured the levels of mitochondrial superoxide in LSK cells. Upon UDP-Glc treatment, ROS levels were significantly increased in LSK cells (FIG. 5A, middle panel). As increased intracellular ROS levels upregulate RANKL expression (Bai et al., 2005; Barsony et al., 2011), which could in turn enhance HSPC mobilization (Kollet et al., 2006), we examined whether UDP-Glc has any direct effect on RANKL expression. UDP-Glc induced an increase of RANKL expression, as demonstrated by both Western blot and immunohistochemical analyses (FIGS. 5B and 5C). RANKL is a potent driver of osteoclast formation, and tipping the balance in favor of osteoclasts leads to mobilization of HSPCs (Purton and Scadden, 2006). We observed a higher proportion of osteoclast cells in UDP-Glc-treated mice, as evidenced by the expression of the osteoclast-associated enzyme tartrate-resistant acid phosphatase (TRAP) (FIG. 5D). However, this UDP-Glc-induced osteoclastogenesis was transient, since the ratio of osteoblasts to osteoclasts returned to the pre-stimulation baseline value 3-4 weeks after the treatment was stopped (See FIG. 8).

Figure 6A:
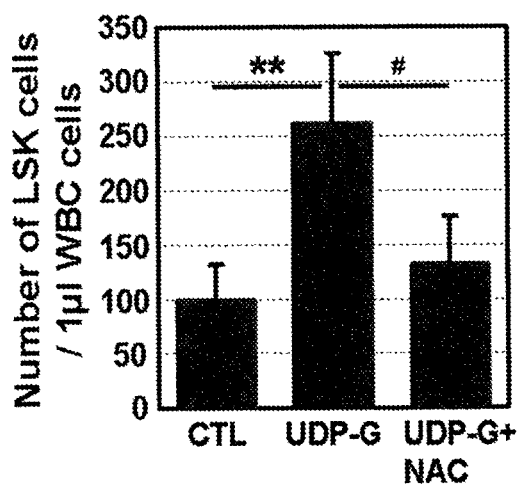
Figure 6C:
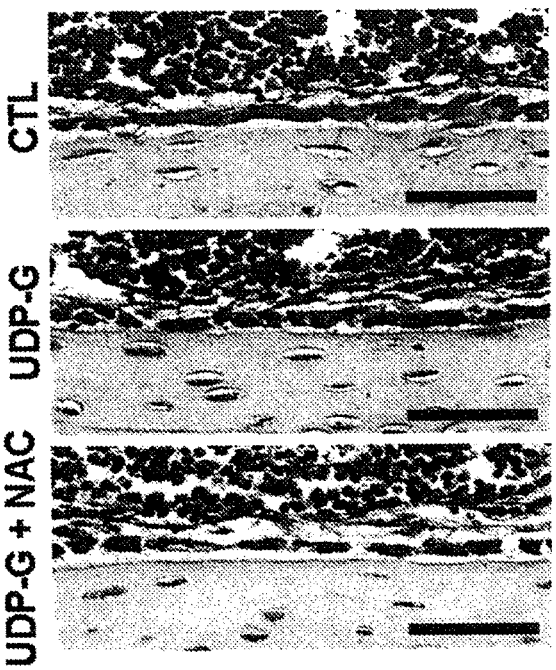
Figure 6B:
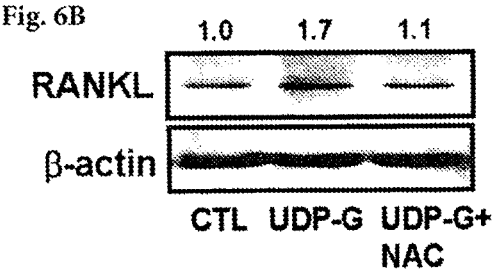
Figure 6D:
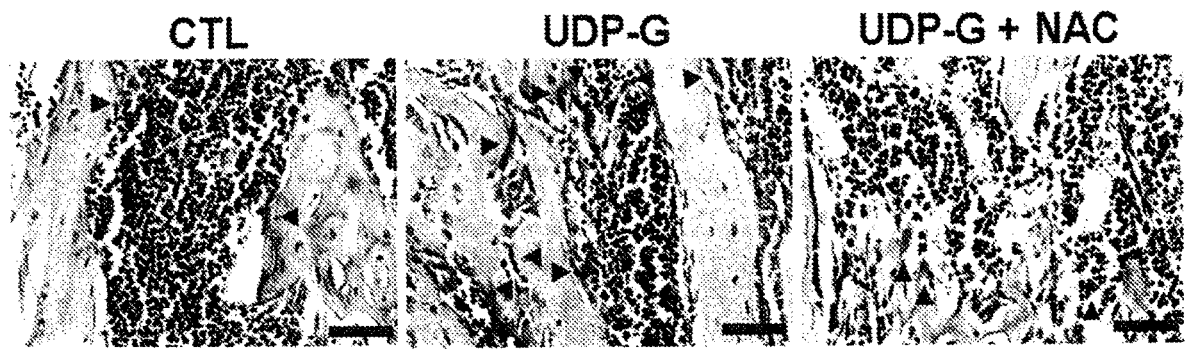

To investigate if the elevated ROS levels are indeed potential mediators of the UDP-Glc-mediated HSPC mobilization, an antioxidant, N-Acetylcysteine (NAC), was administered. NAC was able to significantly abrogate the LSK cell mobilization induced by UDP-Glc (FIG. 6A), suggesting that ROS acted as potential mediators in UDP-Glc mobilization. We then asked whether the abrogation of UDP-Glc mobilization by NAC is through inhibition of RANKL expression. Indeed, RANKL expression was notably lowered in NAC-treated animals in comparison with UDP-Glc-treated animals (FIGS. 6B and 6C). Similarly, the level of UDP-Glc-induced osteoclastogenesis was significantly suppressed with NAC treatment (FIG. 6D).

Without being bound to any particular theory, it is plausible that UDP-Glc increases ROS levels, and this in turn enhances RANKL-induced osteoclast differentiation, leading to HSPC mobilization.

Interestingly, while the combination of UDP-Glc and G-CSF augmented HSPC mobilization, it significantly reduced ROS levels compared to UDP-Glc alone (FIG. 5A, right panel). This suggests that the combination of UDP-Glc and G-CSF augments its mobilizing effect through as yet unknown mechanisms, rather than via a further increment of ROS level.

6.3 Discussion

Mobilized HSPCs could regenerate a complete hematopoietic system for cancer patients with hematolymphoid malignancies or solid tumors, yet, more than 20 percent of patients fail to mobilize sufficient stem cells for transplantation (Schmitz et al., 1996). These so-called "poor mobilizer patients" include patients who were previously treated with intensive radiation and chemotherapy; those who have genetic disorders such as Fanconi's anemia; and those who are over 60 years of age (Broxmeyer et al., 2005; Cottler-Fox et al., 2003). A combination of G-CSF with cytotoxic agents improves HSPC mobilization in the poor mobilizer patients, but often is accompanied by serious side effects (Hornung and Longo, 1992). Such limitations necessitate the discovery of novel mobilizing regimens that permit tailoring therapy on an individual basis.

In this study, we identified UDP-Glc as a novel mobilizer of HSPCs and investigated the phenotypic and functional features of UDP-Glc-mobilized cells.

Following administration of UDP-Glc, the blood contained increased numbers of HSPCs including CFU-GM, BFU-E and CFU-GEMM. However, UDP-Glc-mobilized cells had a significantly lower capacity to form in vitro colonies compared to G-CSF-mobilized cells. This indicates that UDP-Glc is not as efficient as G-CSF in mobilizing lineage committed progenitor cells. In contrast, UDP-Glc and G-CSF exhibited an approximately equivalent level of CAFC activity, suggesting that UDP-Glc preferentially mobilize the more primitive subset of HSPCs.

Functional characteristics of HSPC, such as homing, engraftment, cell cycle status and self renewal vary according to their tissue of origin (Chitteti et al., 2011; Lapid et al., 2008). Indeed, circulating blood stem cells cannot compete effectively against bone marrow-derived stem cells for long-term multilineage repopulation (Micklem et al., 1975). Therefore, when mobilized cells are assessed for their functional activity, it is more legitimate to compare cells from same tissue origin, i.e. G-CSF-mobilized peripheral blood vs. UDP-Glc-mobilized peripheral blood.

To this end, we adapted a competitive repopulation assay in which a mixture of equal numbers of UDP-Glc- and G-CSF-mobilized blood cells are transplanted into conditioned recipients, which allows a direct comparison of UDP-Glc-mobilized cells to G-CSF-mobilized cells under the same microenvironment. Using the donor chimerism analysis at several time points following transplantation, we found that G-CSF-mobilized cells were predominant during the early post-transplantation period, which probably reflects the superior ability of G-CSF to mobilize HSPCs and/or short-term repopulating cells. However, as post-transplant time passed, UDP-Glc-mobilized cells out-competed G-CSF-mobilized cells for the repopulation of recipient animals.

While long-term and short-term HSPCs show a similar multilineage potential, their self renewal capacity is different. Therefore, one of the most important aspects of stem cell mobilization is whether cells mobilized by "mobilizers" have a long-term repopulating ability. UDP-Glc-mobilized peripheral blood contained a greater numbers of SLAM LSK cells than G-CSF-mobilized cells, which could provide a potential explanation for their superior long term repopulating ability (FIG. 3D). The skewing of the lymphoid/myeloid ratio toward the lymphoid lineage was pronounced in the UDP-Glc-mobilized HSPCs (FIG. 3G). All these properties taken together strongly suggest that UDP-Glc mobilizes a functionally distinct subset of the HSPC pool.

It is known that quiescent HSCs have higher long-term repopulating abilities than HSCs in active cell cycle (Passegue et al., 2005). Since UDP-Glc did not disrupt cell cycle quiescence of HSPC (FIG. 3F), this also could contribute to the enhanced long-term engraftment potential of UDP-Glc-mobilized cells. Alternatively, UDP-Glc-mobilized cells gradually gain a competitive advantage over G-CSF-mobilized cells with time, since G-CSF-mobilized cells have reduced long-term repopulation ability (Tesio et al., 2011; Yeoh et al., 2007).

Peripheral blood cells mobilized by a combination of G-CSF and UDP-Glc consistently out-compete G-CSF-mobilized cells throughout the whole post-transplantation period, indicating that the combination regimen enhances both short- and long-term repopulating capacity of the mobilized cells. In this context, UDP-Glc can also be viewed as a complementary regimen that potentiates the long-term repopulating capacity of G-CSF mobilization.

HSPC mobilization is a dynamic, cyclical, and multistage process. The molecular mechanisms that are responsible for HSPC mobilization are complex. Redox signaling plays a central role in regulating HSPC mobilization (Tesio et al., 2011), because many of the cytokines, chemokines and adhesion molecules associated with HSPC mobilization are regulated through a redox-regulated process (Lekli et al., 2009). Mice treated with UDP-Glc expressed high levels of mitochondrial superoxide in their HSPCs. Lowering these ROS levels by antioxidants significantly reduced the mobilizing effect of UDP-Glc and this coincided with the reduction in RANKL and osteoclastogenesis. These results, therefore, suggest that ROS play a role in mediating the UDP-Glc-induced HSPC mobilization through an increase of RANKL expression and osteoclast activity. The other mechanisms for UDP-Glc-induced mobilization would be an indirect effect involving activation of neutrophils with the subsequent release of proteases (Pruijt et al., 2002), since the increased levels of proteases can attack several target proteins, including CXCR4, SDF-1, or VCAM-1, leading to inactivation of CXCR4/CXCL12- or VCAM-1/VLA-4-dependent signals and thus cell migration out of BM. This is however unlikely to be the scenario, because UDP-Glc-mobilized HSPCs appear to favor differentiation of lymphoid rather than myeloid lineage (FIG. 3G).

UDP-Glc is a natural product, so that it may mitigate many of the side effects which are often associated with other synthetic mobilizers. Indeed, none of the UDP-Glc-treated animals showed signs of side effects such as spleen enlargement (See FIG. 7). They appeared normal and healthy during the course of the study. Furthermore, UDP-Glc-induced osteoclastogenesis is only temporary (reversible). The small size of UDP-Glc offers other tangible advantages over other protein-based mobilizers, including easy access to intracellular targets and low cost and ease of production as well as oral bioavailability.

6.4. References

Abbracchio, M. P., and Burnstock, G. (1998). Purinergic signalling: pathophysiological roles. Jpn J Pharmacol 78, 113-145.

Alcino, A., Fresno, M., and Alarcon, B. (1988) Activity of P536, an Analog of UDP-Glucose, Against *Trypanosoma cruzi*. Antimicrob. Agents and Chemother. 32(9), 1412-1415.

Arase, T., Uchida, H., Kajitani, T., Ono, M., Tamaki, K., Oda, H., Nishikawa, S., Kagami, M., Nagashima, T., Masuda, H., et al. (2009). The UDP-glucose receptor P2RY14 triggers innate mucosal immunity in the female reproductive tract by inducing IL-8. J Immunol 182, 7074-7084.

Bai, X. C., Lu, D., Liu, A. L., Zhang, Z. M., Li, X. M., Zou, Z. P., Zeng, W. S., Cheng, B. L., and Luo, S. Q. (2005). Reactive oxygen species stimulates receptor activator of NF-kappaB ligand expression in osteoblast. J Biol Chem 280, 17497-17506.

Barsony, J., Sugimura, Y., and Verbalis, J. G. (2011). Osteoclast response to low extracellular sodium and the mechanism of hyponatremia-induced bone loss. J Biol Chem 286, 10864-10875.

Brautigam, V. M., Dubyak, G. R., Crain, J. M., and Watters, J. J. (2008). The inflammatory effects of UDP-glucose in N9 microglia are not mediated by P2Y14 receptor activation. Purinergic Signal 4, 73-78.

Broxmeyer, H. E., Orschell, C. M., Clapp, D. W., Hangoc, G., Cooper, S., Plett, P. A., Liles, W. C., Li, X., Graham-Evans, B., Campbell, T. B., et al. (2005). Rapid mobilization of murine and human hematopoietic stem and progenitor cells with AMD3100, a CXCR4 antagonist. J Exp Med 201, 1307-1318.

Campbell R. and Tanner, M. (1999). UDP-Glucose Analogues as Inhibitors and Mechanistic Probes of UDP-Glucose Dehydrogenase. J. Org. Chem., 64(26), 9487-9492.

Carter R L, Fricks I P, Barrett M O, Burianek L E, Zhou Y, Ko H, Das A, Jacobson K A, Lazarowski E R, Harden T K. (2009) Quantification of Gi-mediated inhibition of adenylyl cyclase activity reveals that UDP is a potent agonist of the human P2Y14 receptor. Mol Pharmacol. 76(6):1341-8.

Cashen, A. F., Nervi, B. and Dipersio, J. (2007) AMD3100: CXCR4 antagonist and rapid stem cell-mobilizing agent. Future Oncol. 3 (1):19-27.

Chen, Y., Corriden, R., Inoue, Y., Yip, L., Hashiguchi, N., Zinkernagel, A., Nizet, V., Insel, P. A., and Junger, W. G.

(2006). ATP release guides neutrophil chemotaxis via P2Y2 and A3 receptors. Science 314, 1792-1795.

Chitteti, B. R., Liu, Y., and Srour, E. F. (2011). Genomic and proteomic analysis of the impact of mitotic quiescence on the engraftment of human CD34+ cells. PLoS One 6, e17498.

Cottler-Fox, M. H., Lapidot, T., Petit, I., Kollet, O., DiPersio, J. F., Link, D., and Devine, S. (2003). Stem cell mobilization. Hematology Am Soc Hematol Educ Program, 419-437.

Cramer, D., Wagner, S., Li, B., Liu, J., Hansen, R., Reca, R., Wu, W., Surma, E. Z., Laber, D. A., Ratajczak, M. Z., and Yan, J., (2008). Mobilization of Hematopoietic Progenitor Cells by Yeast-Derived-Glucan Requires Activation of Matrix Metalloproteinase-9. Stem Cells 26, 1231-1240.

D'Addio, A., Curti, A., Worel, N., Douglas, K., Motta, M. R., Rizzi, S., Dan, E., Taioli, S., Giudice, V., Agis, H., et al. (2011). The addition of plerixafor is safe and allows adequate PBSC collection in multiple myeloma and lymphoma patients poor mobilizers after chemotherapy and G-CSF. Bone Marrow Transplant 46, 356-363.

Dar, A., Schajnovitz, A., Lapid, K., Kalinkovich, A., Itkin, T., Ludin, A., Kao, W. M., Battista, M., Tesio, M., Kollet, O., et al. (2011). Rapid mobilization of hematopoietic progenitors by AMD3100 and catecholamines is mediated by CXCR4-dependent SDF-1 release from bone marrow stromal cells. Leukemia.

Di Virgilio, F., Chiozzi, P., Ferrari, D., Falzoni, S., Sanz, J. M., Morelli, A., Torboli, M., Bolognesi, G., and Baricordi, O. R. (2001). Nucleotide receptors: an emerging family of regulatory molecules in blood cells. Blood 97, 587-600.

Eigenbrodt, E., Reinacher, M., Scheefers-Borchel, U., Scheefers, H., and Friis, R. (1992). Double role for pyruvate kinase type M2 in the expansion of phosphometabolite pools found in tumor cells. Crit Rev Oncog 3, 91-115.

Fricks, I. P., Maddileti, S., Carter, R. L., Lazarowski, E. R., Nicholas, R. A., Jacobson, K. A., and Harden, T. K. (2008) UDP Is a Competitive Antagonist at the Human P2Y14 Receptor) Pharmacol Exp Ther. 325(2), 588-594.

Greenbaum, A. M., and Link, D. C. (2011). Mechanisms of G-CSF-mediated hematopoietic stem and progenitor mobilization. Leukemia 25, 211-217.

Hamel et al., (2011) J Biomol Screen 16 (9), 1098-1105.

Hartmann, O., Le Corroller, A. G., Blaise, D., Michon, J., Philip, I., Norol, F., Janvier, M., Pico, J. L., Baranzelli, M. C., Rubie, H., et al. (1997). Peripheral blood stem cell and bone marrow transplantation for solid tumors and lymphomas: hematologic recovery and costs. A randomized, controlled trial. Ann Intern Med 126, 600-607.

Hill, G. R., Olver, S. D., Kuns, R. D., Varelias, A., Raffelt, N. C., Don, A. L., Markey, K. A., Wilson, Y. A., Smyth, M. J., Iwakura, Y., et al. (2010). Stem cell mobilization with G-CSF induces type 17 differentiation and promotes scleroderma. Blood 116, 819-828.

Hornung, R. L., and Longo, D. L. (1992). Hematopoietic stem cell depletion by restorative growth factor regimens during repeated high-dose cyclophosphamide therapy. Blood 80, 77-83.

Kollet, O., Dar, A., Shivtiel, S., Kalinkovich, A., Lapid, K., Sztainberg, Y., Tesio, M., Samstein, R. M., Goichberg, P., Spiegel, A., et al. (2006). Osteoclasts degrade endosteal components and promote mobilization of hematopoietic progenitor cells. Nat Med 12, 657-664.

Lapid, K., Vagima, Y., Kollet, O., and Lapidot, T. (2008). Egress and mobilization of hematopoietic stem and progenitor cells.

Lazarowski, E. R., Shea, D. A., Boucher, R. C., and Harden, T. K. (2003). Release of cellular UDP-glucose as a potential extracellular signaling molecule. Mol Pharmacol 63, 1190-1197.

Lekli, I., Gurusamy, N., Ray, D., Tosaki, A., and Das, D. K. (2009). Redox regulation of stem cell mobilization. Can J Physiol Pharmacol 87, 989-995.

Linden, J. (2006). Cell biology. Purinergic chemotaxis. Science 314, 1689-1690.

Liu, F., Poursine-Laurent, J., and Link, D. C. (2000). Expression of the G-CSF receptor on hematopoietic progenitor cells is not required for their mobilization by G-CSF. Blood 95, 3025-3031.

Majolino, I., Aversa, F., Bacigalupo, A., Bandini, G., Arcese, W., and Reali, G. (1995). Allogeneic transplants of rhG-CSF-mobilized peripheral blood stem cells (PBSC) from normal donors. GITMO. Gruppo Italiano Trapianto di Midollo Osseo. Haematologica 80, 40-43.

Micklem, H. S., Anderson, N., and Ross, E. (1975). Limited potential of circulating haemopoietic stem cells. Nature 256, 41-43.

Mollee, P., Pereira, D., Nagy, T., Song, K., Saragosa, R., Keating, A., and Crump, M. (2002). Cyclophosphamide, etoposide and G-CSF to mobilize peripheral blood stem cells for autologous stem cell transplantation in patients with lymphoma. Bone Marrow Transplant 30, 273-278.

Neben, S., Marcus, K., and Mauch, P. (1993). Mobilization of hematopoietic stem and progenitor cell subpopulations from the marrow to the blood of mice following cyclophosphamide and/or granulocyte colony-stimulating factor. Blood 81, 1960-1967.

Park, C. Y., Majeti, R., and Weissman, I. L. (2008). In vivo evaluation of human hematopoiesis through xenotransplantation of purified hematopoietic stem cells from umbilical cord blood. Nat Protoc 3, 1932-1940.

Passegue, E., Wagers, A. J., Giuriato, S., Anderson, W. C., and Weissman, I. L. (2005). Global analysis of proliferation and cell cycle gene expression in the regulation of hematopoietic stem and progenitor cell fates. J Exp Med 202, 1599-1611.

Platzbecker, U., Prange-Krex, G., Bornhauser, M., Koch, R., Soucek, S., Aikele, P., Haack, A., Haag, C., Schuler, U., Berndt, A., et al. (2001). Spleen enlargement in healthy donors during G-CSF mobilization of PBPCs. Transfusion 41, 184-189.

Ploemacher, R. E., van der Sluijs, J. P., Voerman, J. S., and Brons, N. H. (1989). An in vitro limiting-dilution assay of long-term repopulating hematopoietic stem cells in the mouse. Blood 74, 2755-2763.

Pruijt, J. F., Verzaal, P., van Os, R., de Kruijf, E. J., van Schie, M. L., Mantovani, A., Vecchi, A., Lindley, I. J., Willemze, R., Starckx, S., et al. (2002). Neutrophils are indispensable for hematopoietic stem cell mobilization induced by interleukin-8 in mice. Proc Natl Acad Sci USA 99, 6228-6233.

Pulliam, A. C., Hobson, M. J., Ciccone, S. L., Li, Y., Chen, S., Srour, E. F., Yang, F. C., Broxmeyer, H. E., and Clapp, D. W. (2008). AMD3100 synergizes with G-CSF to mobilize repopulating stem cells in Fanconi anemia knockout mice. Exp Hematol 36, 1084-1090.

Purton, L. E., and Scadden, D. T. (2006). Osteoclasts eat stem cells out of house and home. Nat Med 12, 610-611.

Rossi, L., Manfredini, R., Bertolini, F., Ferrari, D., Fogli, M., Zini, R., Salati, S., Salvestrini, V., Gulinelli, S., Adinolfi, E., et al. (2007). The extracellular nucleotide UTP is a potent inducer of hematopoietic stem cell migration. Blood 109, 533-542.

Sak, K., Boeynaems, J. M., and Everaus, H. (2003). Involvement of P2Y receptors in the differentiation of haematopoietic cells. J Leukoc Biol 73, 442-447.

Schmitz, N., Linch, D. C., Dreger, P., Goldstone, A. H., Boogaerts, M. A., Ferrant, A., Demuynck, H. M., Link, H., Zander, A., and Barge, A. (1996). Randomised trial of filgrastim-mobilised peripheral blood progenitor cell transplantation versus autologous bone-marrow transplantation in lymphoma patients. Lancet 347, 353-357.

Scrivens, M., and Dickenson, J. M. (2005). Pharmacological effects mediated by UDP-glucose that are independent of P2Y14 receptor expression. Pharmacol Res 51, 533-538.

Steinman, R. A. (2002). Cell cycle regulators and hematopoiesis. Oncogene 21, 3403-3413.

Tesio, M., Golan, K., Corso, S., Giordano, S., Schajnovitz, A., Vagima, Y., Shivtiel, S., Kalinkovich, A., Caione, L., Gammaitoni, L., et al. (2011). Enhanced c-Met activity promotes G-CSF-induced mobilization of hematopoietic progenitor cells via ROS signaling. Blood 117, 419-428.

Tricot, G., Jagannath, S., Vesole, D., Nelson, J., Tindle, S., Miller, L., Cheson, B., Crowley, J., and Barlogie, B. (1995). Peripheral blood stem cell transplants for multiple myeloma: identification of favorable variables for rapid engraftment in 225 patients. Blood 85, 588-596.

Wihlborg A K, Balogh J, Wang L, Borna C, Dou Y, Joshi B V, Lazarowski E, Jacobson K A, Amer A, Erlinge D. (2006). Positive inotropic effects by uridine triphosphate (UTP) and uridine diphosphate (UDP) via P2Y2 and P2Y6 receptors on cardiomyocytes and release of UTP in man during myocardial infarction. Circ Res. 98(7):970-6

Wright, D. E., Cheshier, S. H., Wagers, A. J., Randall, T. D., Christensen, J. L., and Weissman, I. L. (2001). Cyclophosphamide/granulocyte colony-stimulating factor causes selective mobilization of bone marrow hematopoietic stem cells into the blood after M phase of the cell cycle. Blood 97, 2278-2285.

Yeoh, J. S., Ausema, A., Wierenga, P., de Haan, G., and van Os, R. (2007). Mobilized peripheral blood stem cells provide rapid reconstitution but impaired long-term engraftment in a mouse model. Bone Marrow Transplant 39, 401-409.

7. EXAMPLE 2

UDP-Glucose is a Novel Mobilizer of Long-Term Repopulating Primitive Hematopoietic Cells

7.1 Materials and Methods

Animals and Treatment.

Mice received subcutaneous injections of UDP-glucose (200 mg/kg, Sigma) dissolved in sterile endotoxin-free PBS. G-CSF (Neupogen, Amgen) was administered daily at a dose of 300 µg/kg subcutaneously for 4 consecutive days as previously described (10). For the combination group, mice were injected UDP-Glc at 200 mg/kg subcutaneously for 6 consecutive days (from day 0 to day 5), accompanied by 300 µg/kg subcutaneous injections of G-CSF (from day 2 to day 5). Antioxidant, N-acetyl-L-cysteine (Sigma-Aldrich), was administered subcutaneously at 100 mg/kg/day. Bone marrow cells were obtained from both femur and tibia and used for flow cytometry and Western blot analysis. All animal studies were conducted after review by the University of Pittsburgh's Institutional Animal Care and Use Committee and in accordance with the University of Pittsburgh's Policy on the Care, Welfare and Treatment of Laboratory Animals.

Colony Forming Cell (CFC) Assay and Cobblestone Area Forming Cell (CAFC) Assay.

Mobilized mononuclear peripheral blood cells ($1\times10^6$) and spleen cells ($0.5\times10^6$) were seeded for CFC assay. The number of BFU-E, CFU-GM and CFU-GEMM colonies was counted using standard criteria. CAFC assay was performed in duplicate using MyeloCult M5300 (StemCell Technologies) as described previously (58). After 5 weeks, wells containing cobblestone areas were counted as positive wells.

Transplantation.

For competitive repopulation assays, an equal number of peripheral blood cells mobilized by each agent (PBS vs. UDP-Glc; UDP-Glc vs. G-CSF; G-CSF vs. UDP-Glc/G-CSF) were transplanted into conditioned recipient mice (CD45.1.2., 9.5-10Gy). Although we used CD45 congenic animals (B6) in competitive repopulation assay, in order to confirm that our results are not due to potential variability resulting from the disparity between the CD45.1 and CD45.2, the results were further confirmed by injecting mobilizers the other way around (ex; inject G-CSF into CD45.1 and UDP-Glc to CD45.2 mice, and vice versa). The ratio of CD45.1/CD45.2 cells in recipient's peripheral blood was determined at various times after transplantation. When we transplant sorted CD45.1+ SLAM LSK or CD45.2+ SLAM LSK cells into lethally irradiated animals, 1-$2\times10^6$ peripheral blood cells (CD45.1.2) were co-administered whose contribution to recipient hematopoietic reconstitution is minimal.

Flow Cytometry Analysis.

The relative contributions of UDP-Glc, G-CSF, and UDP-Glc/G-CSF-mobilized peripheral blood cells to recipient blood and bone marrow were assessed by flow cytometry analysis using anti-CD45.1 and anti-CD45.2 antibodies (eBioscience). Peripheral blood Lin-/Sca-1+/c-Kit+(LSK) and CD150+CD48-(SLAM) LSK cells were phenotyped using the following antibodies: lineage markers PE-Cy7-conjugated anti-CD3, anti-CD4, anti-CD8, anti-CD45R, anti-CD11b, anti-Gr-1, and anti-TER-119 (eBioscience); PE-conjugated anti-Sca-1 (eBioscience); APC-conjugated anti-c-Kit (eBioscience); perCP/Cy5.5-conjugated anti-CD150 (BioLegend); pacific Blue™-conjugated anti-CD48 (BioLegend). The percentage of bone marrow LSK and SLAM LSK cells derived from UDP-Glc- and G-CSF-mobilized cells was analyzed among gated either the CD45.1 or CD45.2 compartment. Mitochondrial superoxide level was measured using MitoSox™ (Invitrogen) within LSK cells, according to manufacturer's instructions.

Western Blot Analysis.

Equal amounts (20 µg/sample) of protein extracts were loaded on 15% SDS-PAGE and blotted onto polyvinyl difluoride membranes. The blots were probed with primary antibody specific for goat polyclonal RANKL (Santa Cruz Biotechnology) and mouse monoclonal β-actin (Sigma-Aldrich) overnight at 4° C. Densitometric analysis was performed using Un-scan-IT image analysis software.

TRAP Staining and Immunohistochemistry:

Femurs dissected from treated mice were fixed in 4% paraformaldehyde solution in phosphate buffered saline (PBS, pH7.2) for 2 days and then decalcified in 10% EDTA (pH 7.5) for 10 days. After decalcification, they were embedded in paraffin and longitudinally cut to 5 µm thickness. For identification of osteoclasts, the sections were deparaffinized, dehydrated, and stained using TRAP staining kit (B-Bridge International, Inc.) according to the manufacturer's instructions. For the in vitro osteoclast differentiation assay, bone marrow cells ($2\times10^5$) were pretreated with 20 ng/ml M-CSF (eBioscience) for 3 days and further cultured 4 days with various concentrations (0-200 □M) of UDP-Glc. After seven days of incubation, the cells were stained and counted as described above. For immunohistochemical staining of RANKL, after dehydration, the sections were immunolabeled overnight with goat polyclonal antibody against mouse RANKL (Santa Cruz Biotechnology, 1:50) at 4° C. Subsequently, they were incubated with biotinylated goat-specific secondary antibody (Vector Laboratories) followed by DAB staining according to the manufacturer's instructions (Vector Laboratories).

Chemotaxis Assay.

For chemotactic assays, lineage-depleted cells (106/well) were placed in the upper chamber. UDP, UTP and UDP-G (10 µM, Sigma) were placed to the bottom chamber with or without CXCL12 (120 ng/ml, Peprotech). After 6 hours incubation, migrated cells were stained with FITC-conjugated anti-mouse Sca-1 (eBioscience) and APC-conjugated anti-mouse c-Kit (eBioscience). Flow cytometry was used to enumerate migrated cells.

Zymographic Analysis.

For zymography, bone marrow supernatants were loaded on 10% pre-casted polyacrylamide gel with gelatin for MMP-2 and MMP-9, and 12.5% pre-casted polyacrylamide gel (BIO-RAD) with casein for neutrophil elastase (NE) and cathepsin G (CG) under non-reducing conditions. After electrophoresis, the gels were washed in zymogram renaturation buffer (2.5% Triton X-100) and then incubated overnight at 37° C. in zymogram development buffer (BIO-RAD). The gels were then stained with 0.5% Coomassie blue solution and destained with 30% ethanol and 10% acetic acid. Proteinase activity was determined by colorless zones against a blue background.

Statistical Analysis.

All the data were expressed as the mean±standard deviation (SD). A one-way ANOVA was used for multiple comparisons using SPSS version 16.0 software. A P value <0.05 was considered statistically significant.

7.2 Results

UDP-Glc Promotes Mobilization of Hematopoietic Stem Progenitor Cells.

Figure 9A:
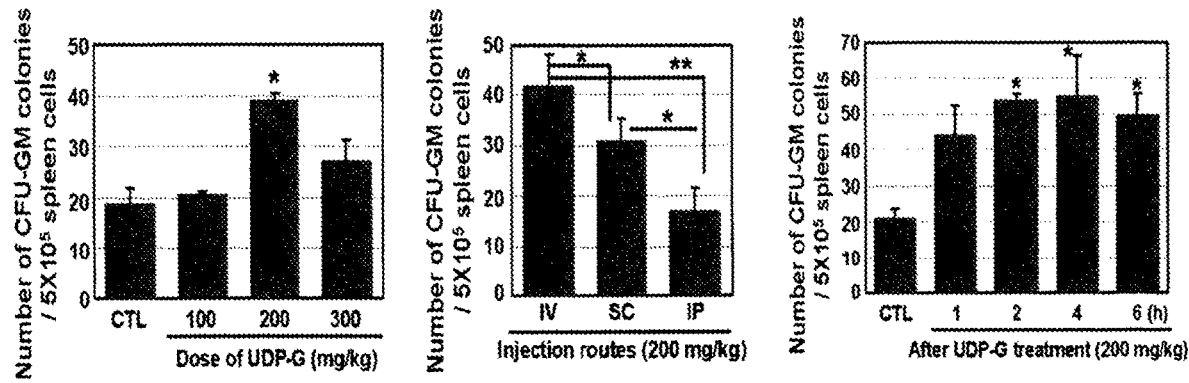
Figure 9B:
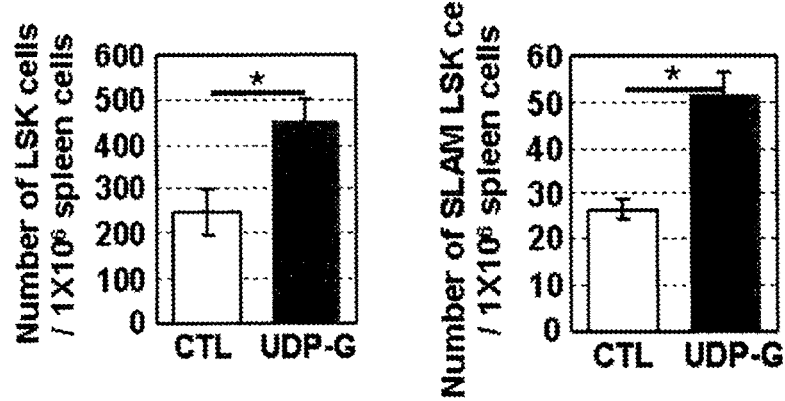

To investigate whether in vivo administration of exogenous UDP-Glc may mimic stress conditions to trigger HSC/HPC mobilization, we injected UDP-Glc into mice and assessed for its ability to mobilize HPCs that are capable of forming colonies (CFU-Cs). Spleen cells from UDP-Glc-treated mice showed an increase in the number of colony-forming unit-granulocyte-macrophage (CFU-GM) (FIG. 9), suggesting that UDP-Glc led mobilization of CFU-Cs to extramedullary sites. In determining optimal dose, UDP-Glc exerted its maximal mobilizing effects at a dose of 200 mg/kg body weight (FIG. 9A, left panel). Although i.v. administration was superior to s.c. or i.p. in mobilizing CFU-GM (FIG. 9A, middle panel), s.c. injection was chosen for further studies to minimize potential side effects of i.v. injection and due to its simplicity. The number of spleen-derived CFU-GM was evident within one hour after UDP-Glc administration, reaching a peak in approximately two to four hours (FIG. 9A, right panel). Regardless of the assay conditions, we consistently observed an increased number of CFU-GM from the spleen of UDP-Glc-treated mice (P<0.05) (FIG. 16). In addition, we observed a statistically significant increase in the number of HSPCs (Lineage-Sca-1+c-kit+ cells, hereafter referred to as LSK) in the spleen of UDP-Glc-treated mice (FIG. 9B, left panel). In particular, UDP-Glc-treated mice exhibited a significant increase in the splenic SLAM LSK cells (FIG. 9B, right panel), which is a very rare and primitive hematopoietic stem cell subset (24). While there is the possibility that UDP-Glc exerts a proliferative effect on the splenic HSPCs thus increasing the number of CFU-GM, the addition of UDP-Glc to the CFU-GM assay did not further increase the number of colonies, excluding such possibility (FIG. 16, right panel).

Figure 9C:
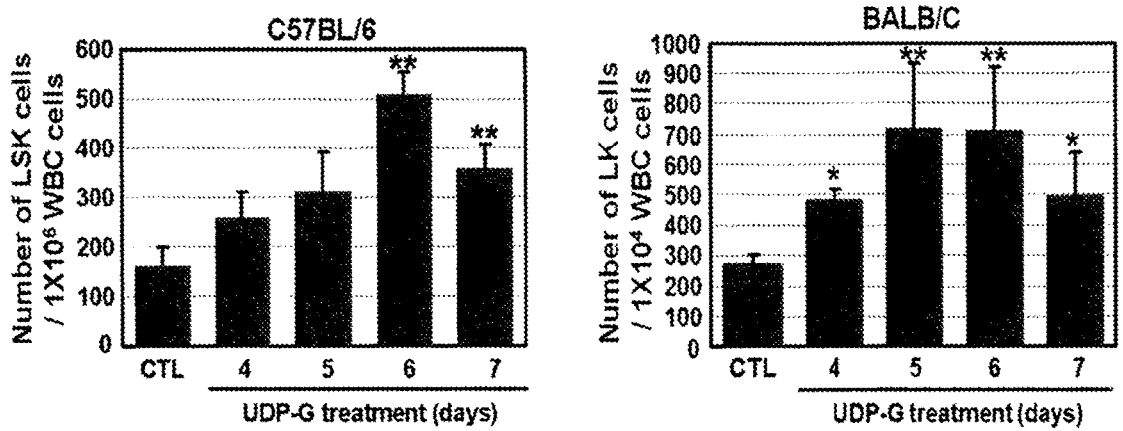
Figure 9D:
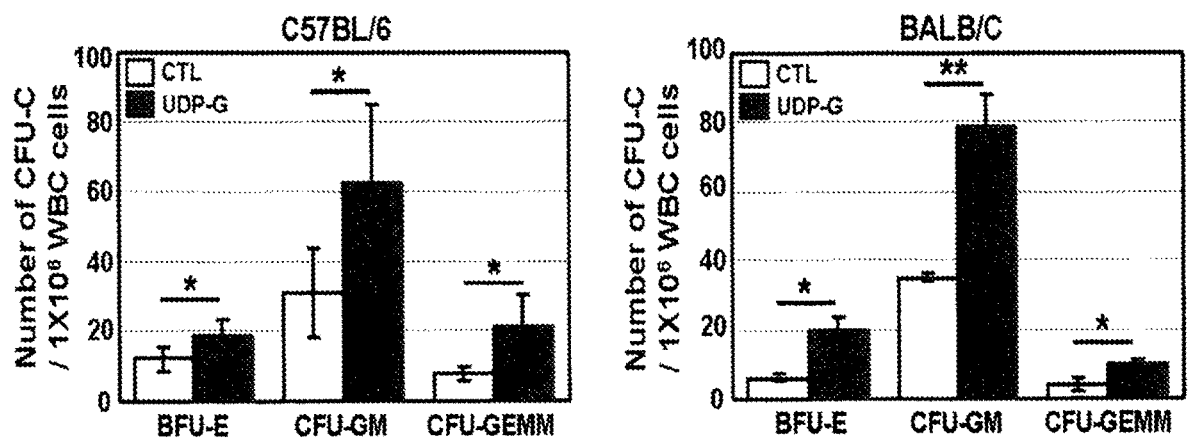

Since mobilized HSPCs are routinely harvested from the peripheral blood in the clinic, we quantified HSPCs in the peripheral blood of UDP-Glc-treated mice. There was a notable increase in the frequency of LSK cells in the circulation after 6 daily single UDP-Glc injections in B6 mice, which is one of the most difficult mouse strain to be mobilized (25) (FIG. 9C, left panel). The mobilizing effect of UDP-Glc was also evident in BALB/C mice (FIG. 9C, right panel), demonstrating that mouse strain did not significantly influence the efficacy of UDP-Glc-induced HSPC mobilization. In line with this, UDP-Glc treatment led to a statistically significant increase of CFU-Cs (CFU-GM, BFU-E, and CFU-GEMM) in the blood of both B6 and BALB/C mice (FIG. 9D). For further study, B6 mice were used not just because of the availability mice that are congenic to for the CD45 isoform, which is useful to track donor cell populations, but also because the KO mice used in the present study to investigate underlying mechanisms have been produced in a B6 background.

Figure 9E:
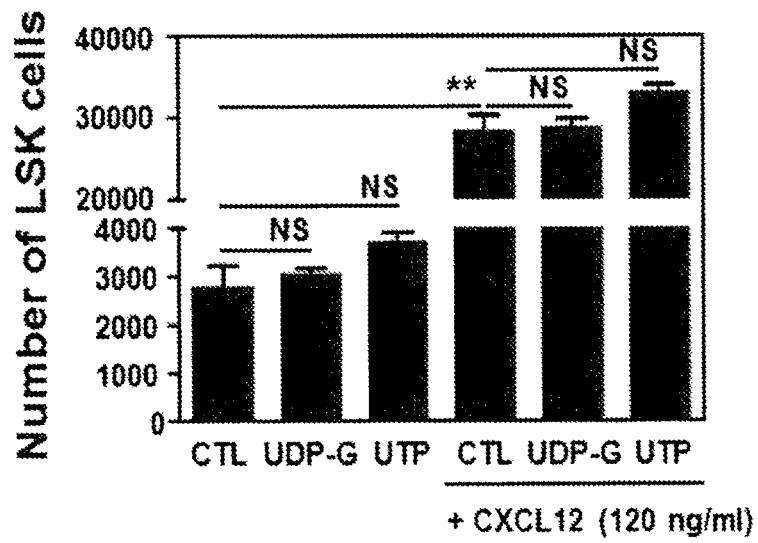

It is known that uridine-5'-triphosphate (UTP) is functionally associated with human HSPC migration and their engraftment (18, 19). We thus examined whether UDP-Glc possesses a similar activity on mouse HSPCs. SDF-1α (CXCL12), as anticipated, potently chemoattracted mouse HSPCs (LSK) cells (FIG. 9E). However, we found no clear evidence that UDP-Glc acts as a chemoattractant for mouse LSK cells either in the absence or presence of CXCL12 (FIG. 9E). While UTP is a known to chemoattract human CD34+ cells, it elicited only a slight increase for mouse LSK cell migration with no statistical significance.

UDP-Glc Mobilizes Long-Term Repopulating Hematopoietic Stem Progenitor Cells.

Figure 10A:
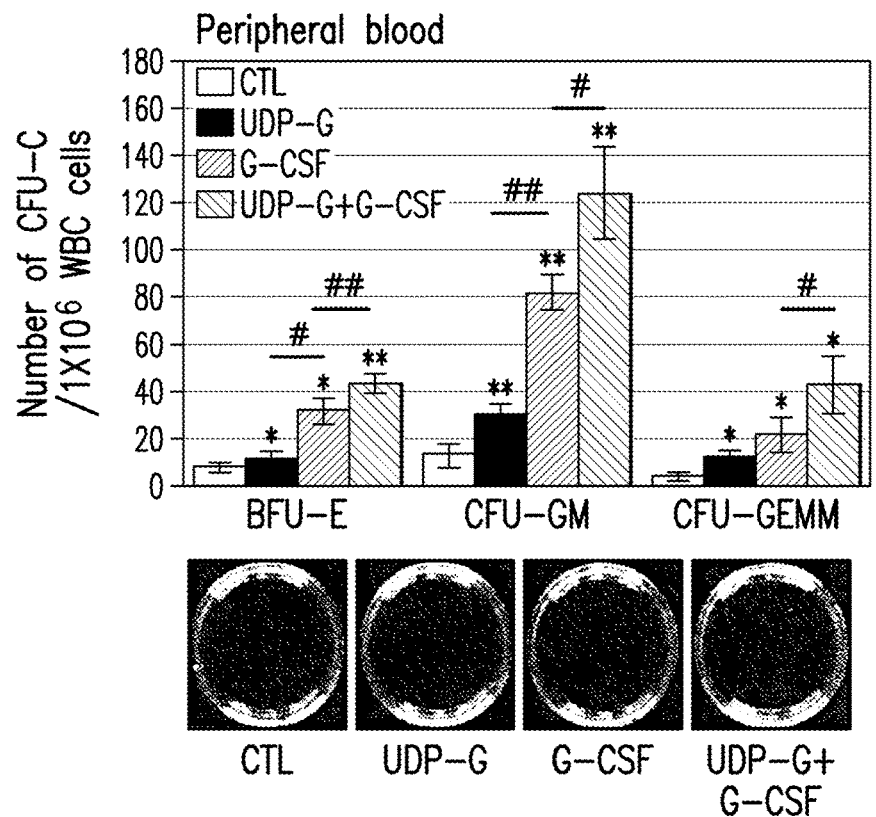
Figure 10B:
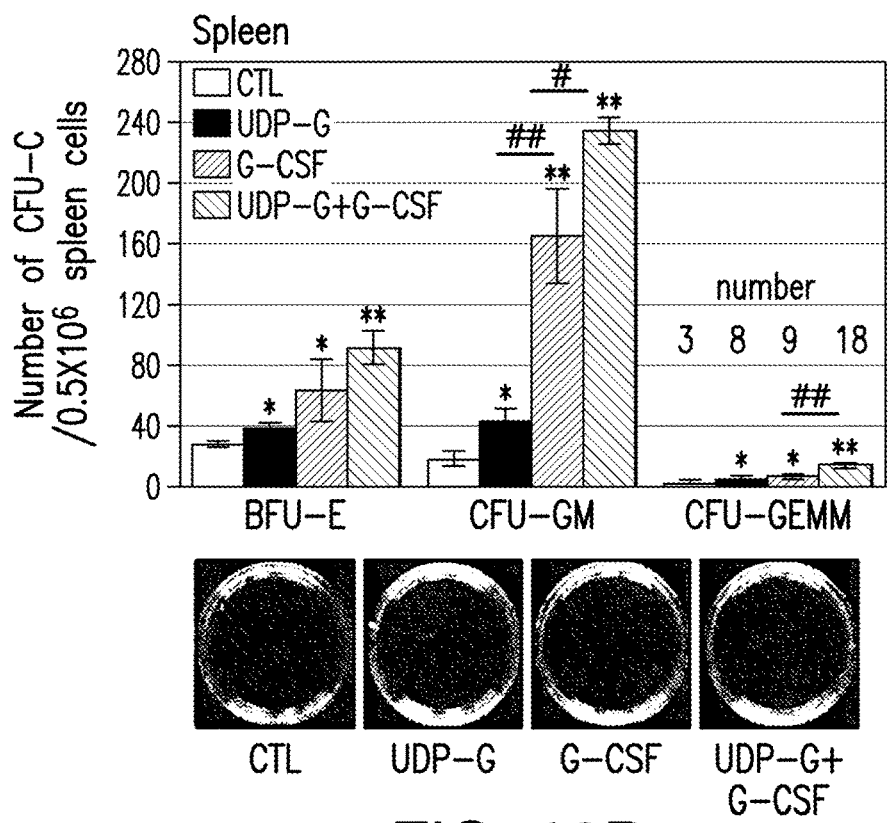
Figure 10C:
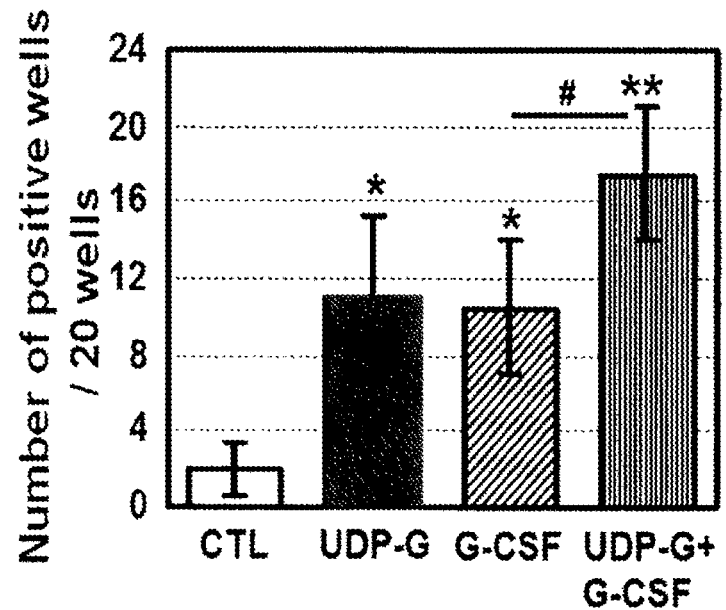
Figure 10D:
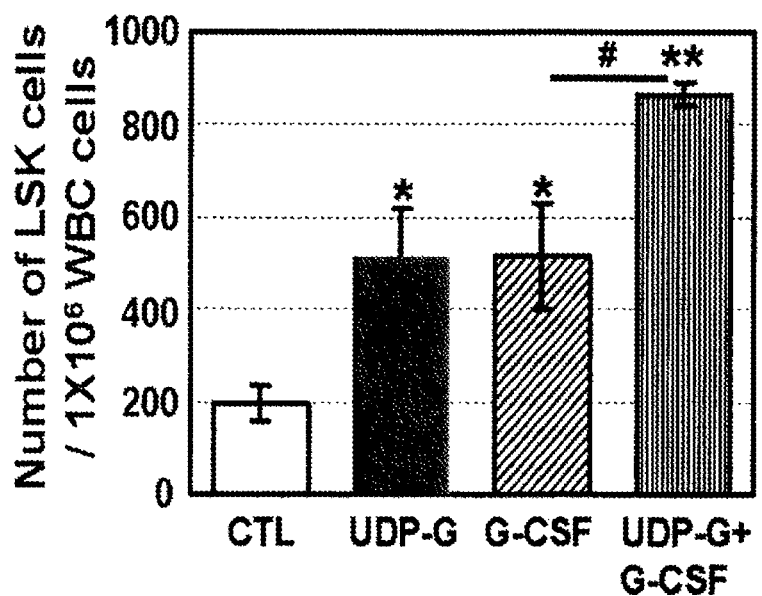
Figure 10E:
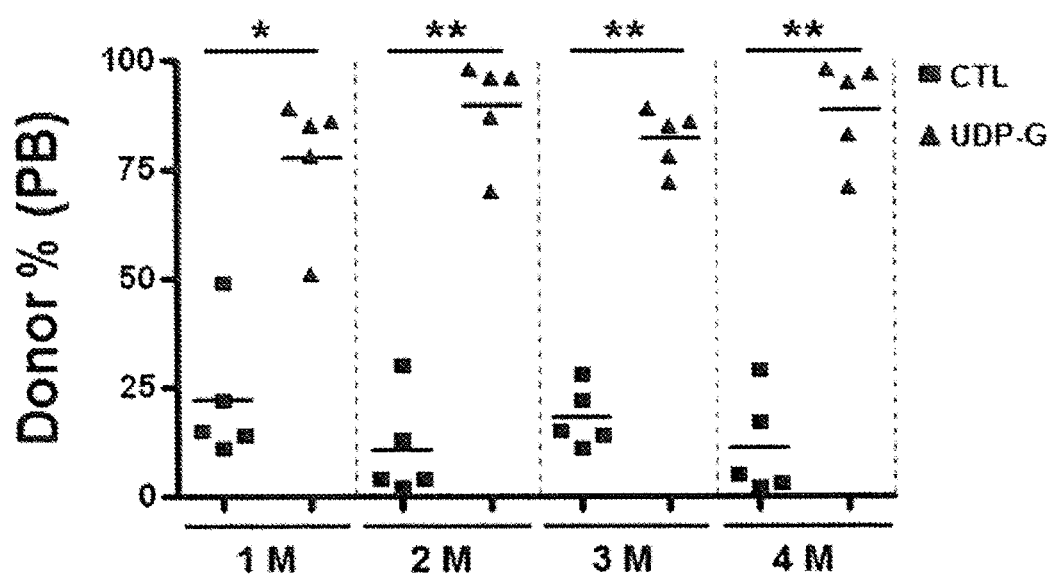

G-CSF is the most commonly used cytokine for mobilization of HSPCs in the clinic. We thus determined the mobilizing capability of UDP-Glc in comparison with G-CSF. G-CSF was administered as described in the previous study (10, 11). As shown in FIGS. 10A and B, UDP-Glc (black bars) was significantly less efficient than G-CSF (hatched bars) in mobilizing CFU-Cs to peripheral blood and spleen. We then performed cobblestone area-forming cell assays (CAFC) to estimate the frequency of more primitive progenitor cells in UDP-Glc-mobilized blood. Despite their low in vitro colony forming capacity, UDP-Glc-mobilized cells displayed high CAFC activity (approximately 10-14 fold higher than vehicle-injected group), which is similar to the fold increase observed with G-CSF-mobilized cells (FIG. 10C). In addition, UDP-Glc was also almost equally potent in mobilizing LSK cells into peripheral blood when compared with G-CSF (FIG. 10D).

Neither phenotypic analysis nor in vitro HPC assays necessarily accurately reflect stem progenitor cell activity in vivo (26). To assess the functional properties of UDP-Glc-mobilized HSPCs in vivo, we performed competitive repopulation assays, where the equal number of blood cells, from either control or UDP-Glc-treated mice, was transplanted into conditioned recipient mice (FIG. 17). UDP-Glc-mobilized cells showed a significant repopulation advantage compared to vehicle-treated blood cells over a 4-month period post-transplant (FIG. 10E), suggesting the long-term repopulating potential of UDP-Glc-mobilized HSPCs. Of note, none of recipients transplanted with control blood cells alone (peripheral blood cells from vehicle (PBS)-injected mice) survived to lethal irradiation. This is primarily due to the fact that HSPCs are present at very low frequencies in steady-state peripheral blood as previously described (3). Only when combined with UDP-Glc-mobilized cells, recipient animals could survive, suggesting that UDP-Glc-mobilized peripheral blood (PB) contains enough HSPCs that allow the lethally irradiated animal to survive the post irradiation.

Figure 10F:
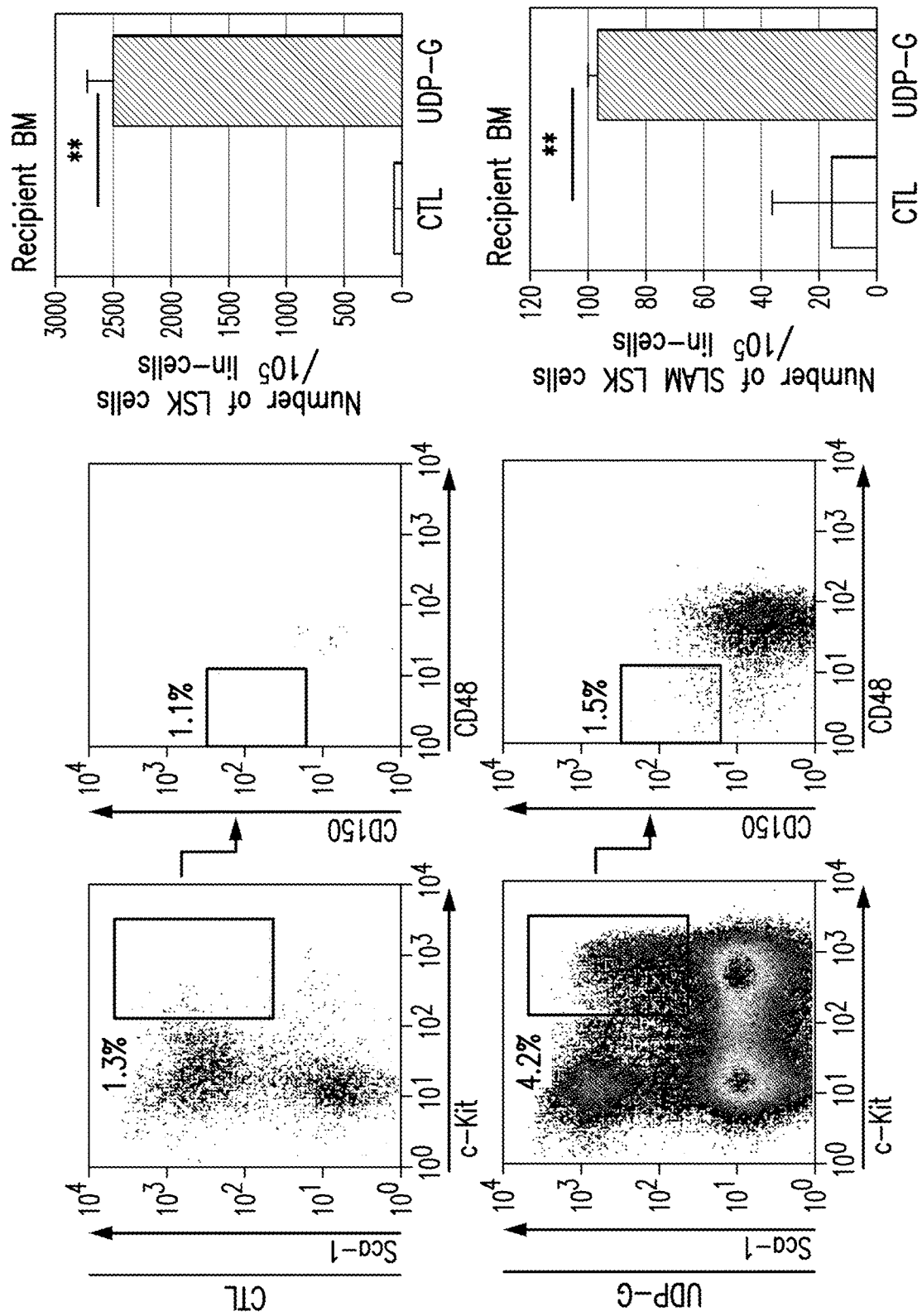
Figure 10G:
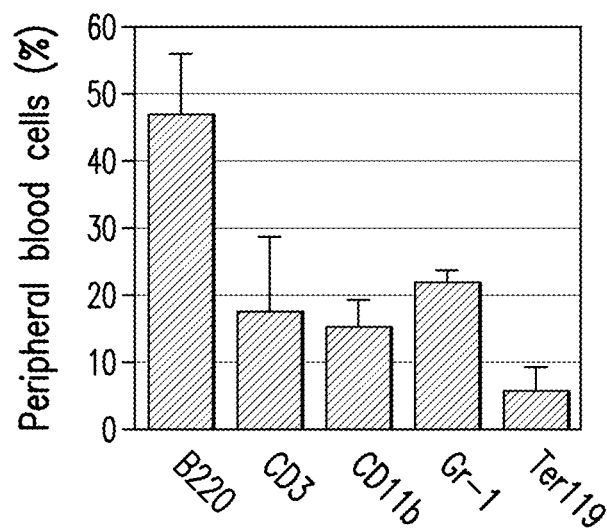
Figure 10G:
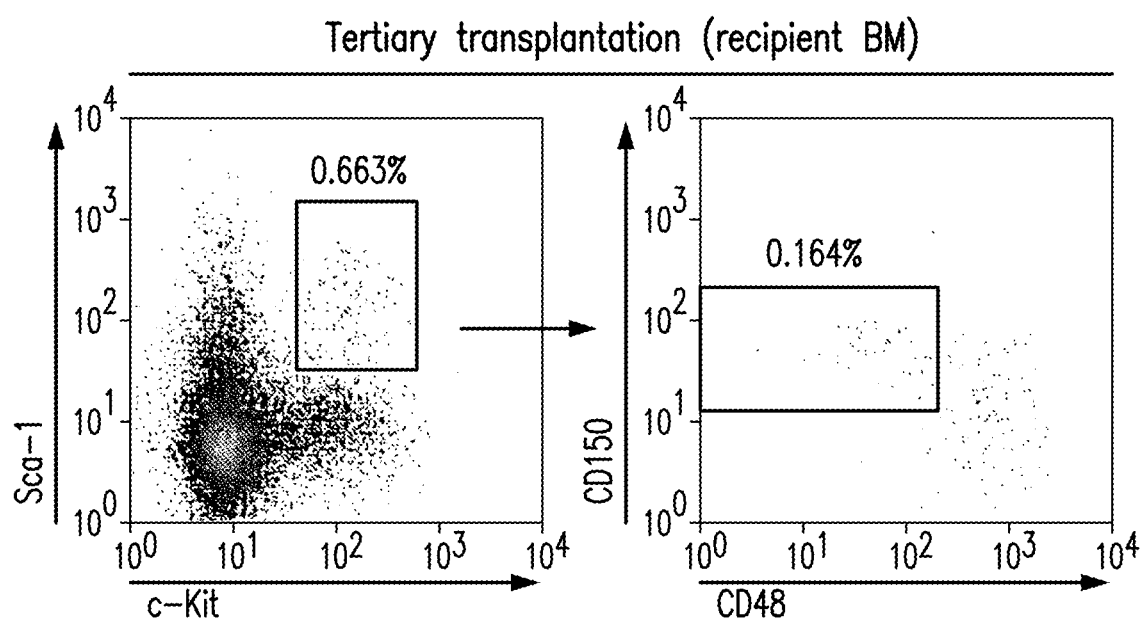

The maintenance of stem cell pool and generation of functional mature blood cells depend on close interaction with specialized microenvironments or niches in bone marrow (27). Therefore, the engraftment of HSPCs to bone marrow more accurately represents clinical outcome in clinical protocols. We thus assessed whether donor-derived HSPCs are sustainable in the bone marrow of recipient animals for an extended period after transplantation. Sixteen weeks after transplantation, we could readily detect HSPC population (LSK and SLAM LSK cells) derived from UDP-Glc-mobilized cells in the bone marrow of recipient animals (FIG. 10F). In contrast, HSPCs-derived from vehicle-treated mice were very low or undetectable. To further validate the phenotypically defined SLAM LSK cells in the primary recipient bone marrow are indeed functional HSPCs, SLAM LSK cells were sorted, then subjected to serial transplantation. As shown in FIG. 10G, donor-derived SLAM LSK cells were capable of durable multi-lineage engraftment on serial transplantation. These results demonstrate that the SLAM LSK subsets detected in the primary recipient bone marrow are functional HSPCs.

Figure 10H:
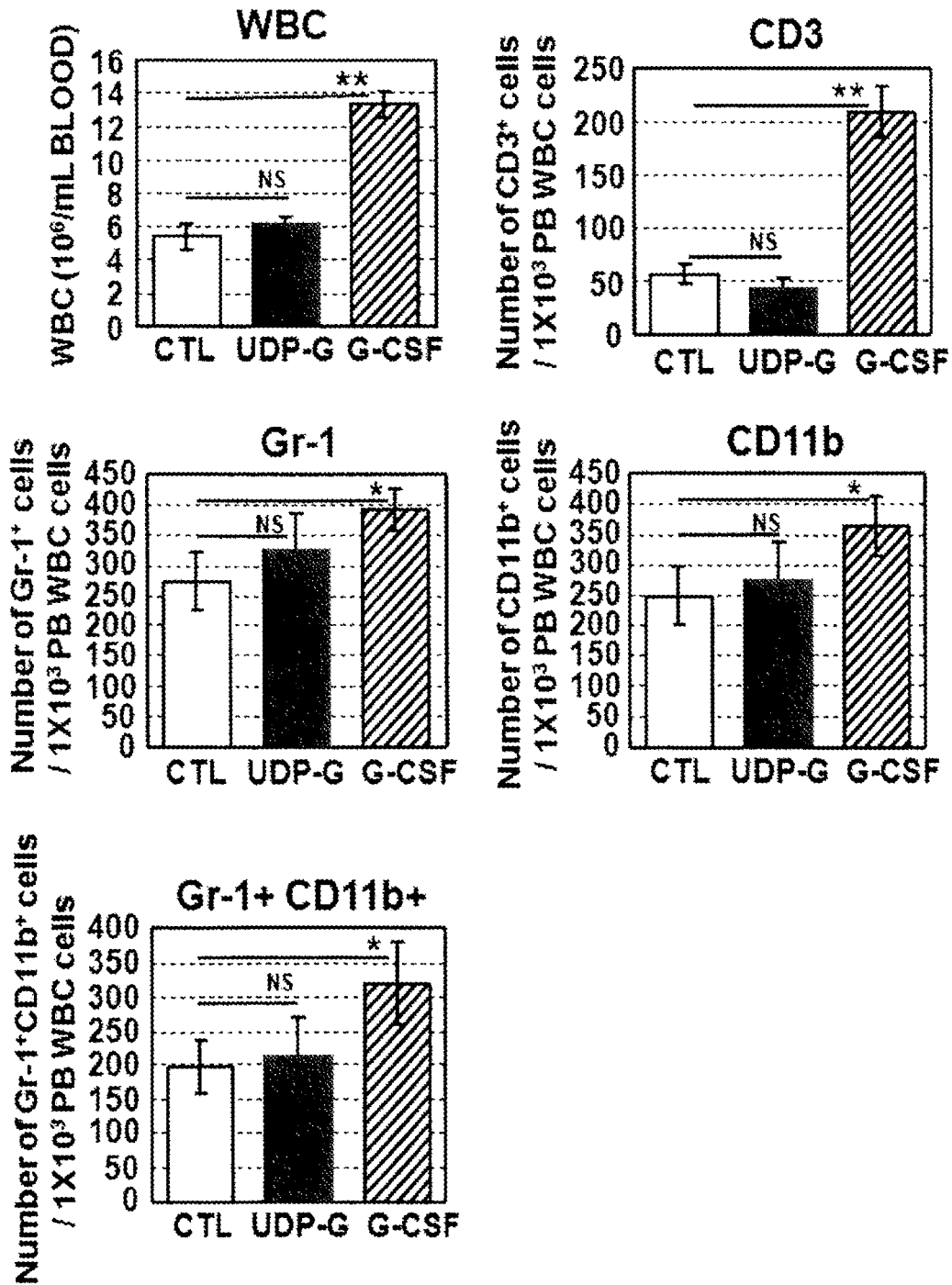

Of note, despite the significant increases in peripheral HSPCs, there was no significant change in the number of white blood cells (WBC) in mice treated with UDP-Glc (FIG. 10H). Importantly, UDP-Glc-treated mice did not show a significant increase in the number of CD3+, Gr-1+ and CD11b+ cells in their peripheral blood, which is contrary to those observed in mice treated with G-CSF (FIG. 10H).

Figure 10I:
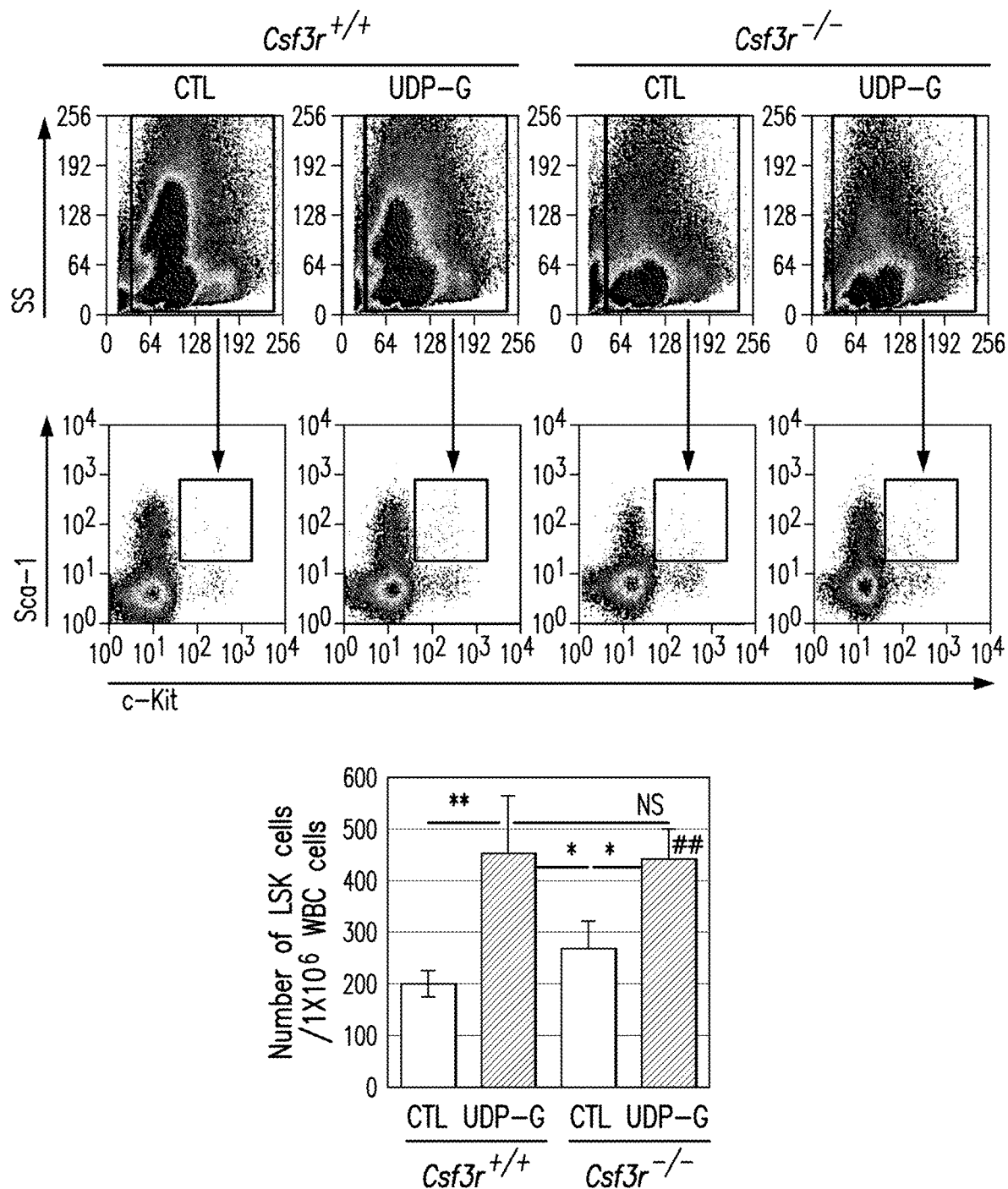
Figure 10J:
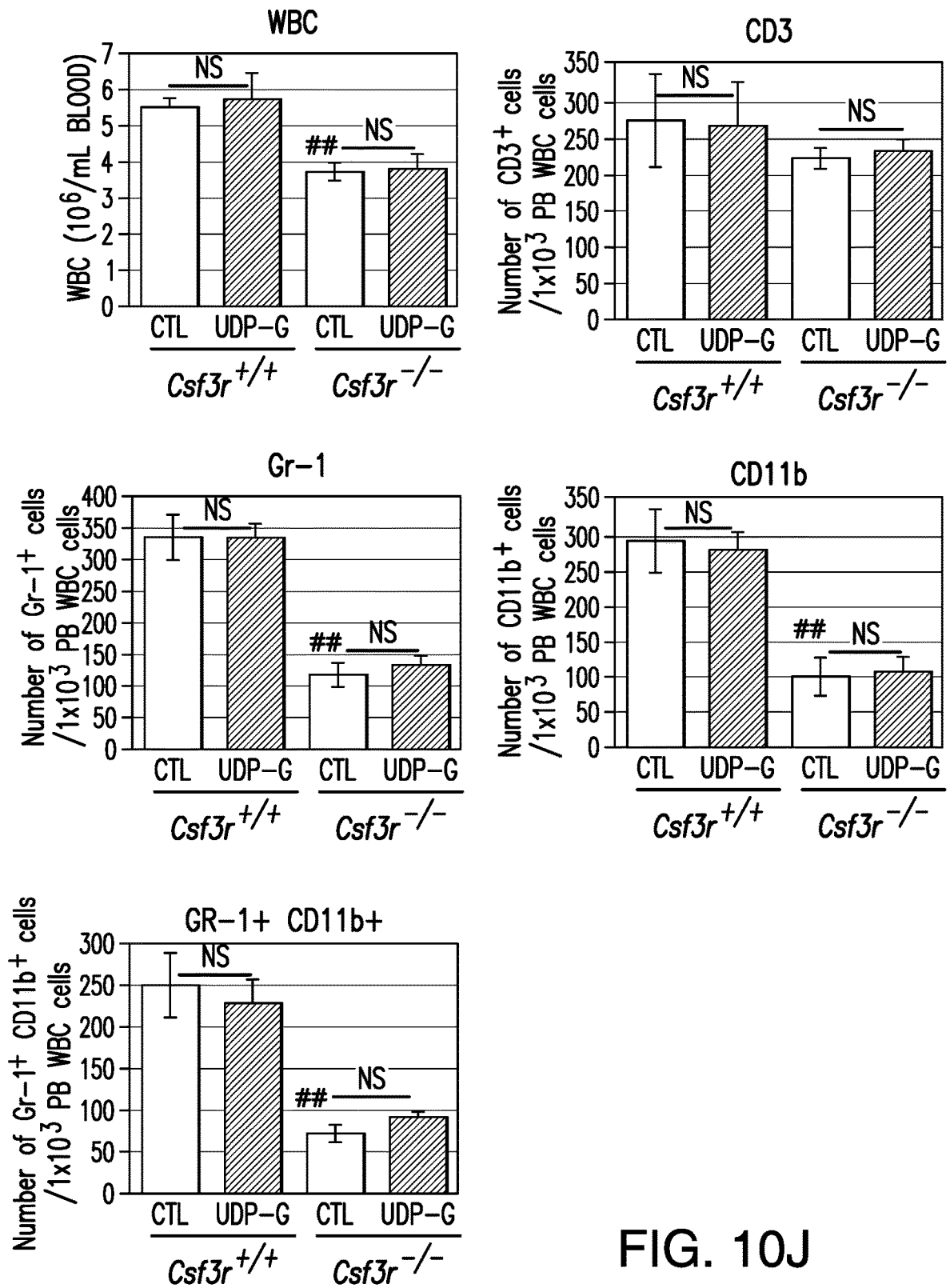

A similar pattern in response to UDP-Glc was observed in G-CSFR deficient mice (Csf3r−/−). Despite the fact that G-CSFR deficient mice are neutrophenic at baseline (28), UDP-Glc was still able to induce a statistically significant mobilization of LSK cells in Csf3r−/− mice (FIG. 10I). Meanwhile, the number of peripheral CD11b+, GR1+ and CD3+ cells was minimally affected in UDP-treated Csf3r−/− mice (FIG. 10J).

UDP-Glucose Mobilizes Distinct Subsets of Hematopoietic Stem Progenitor Cells in Comparison with G-CSF.

Figure 11A:
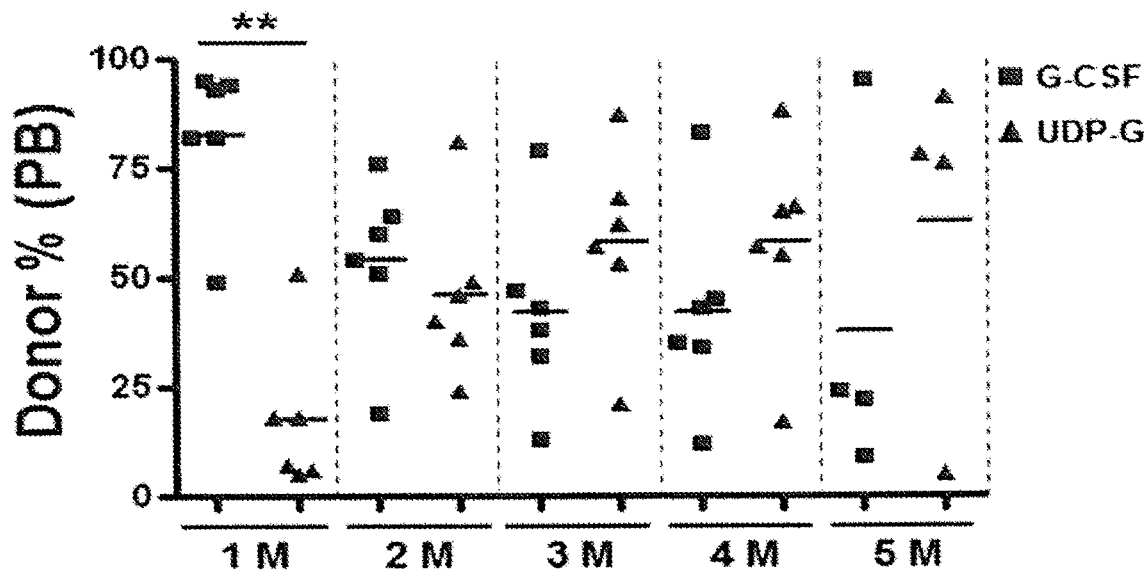
Figure 11B:
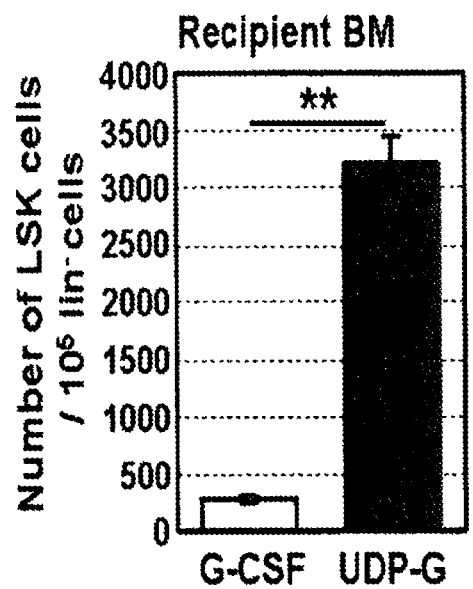
Figure 11C:
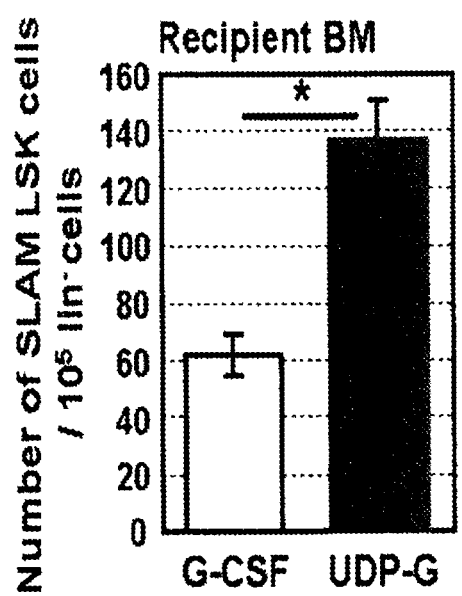

Next, we compared the HSPC mobilizing capability of UDP-Glc with that of G-CSF using competitive repopulation assay. At one month following transplantation, G-CSF-mobilized cells displayed a considerable competitive advantage over UDP-Glc-mobilized cells (FIG. 11A). However, UDP-Glc-mobilized cells began to gain their abilities to compete with G-CSF-mobilized cells at 2 months post-transplant. Notably, UDP-Glc-mobilized cells became dominant and out-competed G-CSF-mobilized cells starting 3 months post-transplant (FIG. 11A), and sustained their competitive advantage thereafter.

We assessed whether this was because recipient's bone marrow niches were predominantly occupied by UDP-Glc-mobilized cells. To this end, we analyzed the bone marrow of primary recipient animals at 18 weeks after transplantation. A significantly higher portion of LSK and SLAM LSK cells in recipient bone marrow were derived from UDP-Glc-treated mice (FIGS. 11B and 11C), indicating that UDP-Glc-mobilized cells achieved higher levels of long-term engraftment than G-CSF-mobilized cells.

Figure 11D:
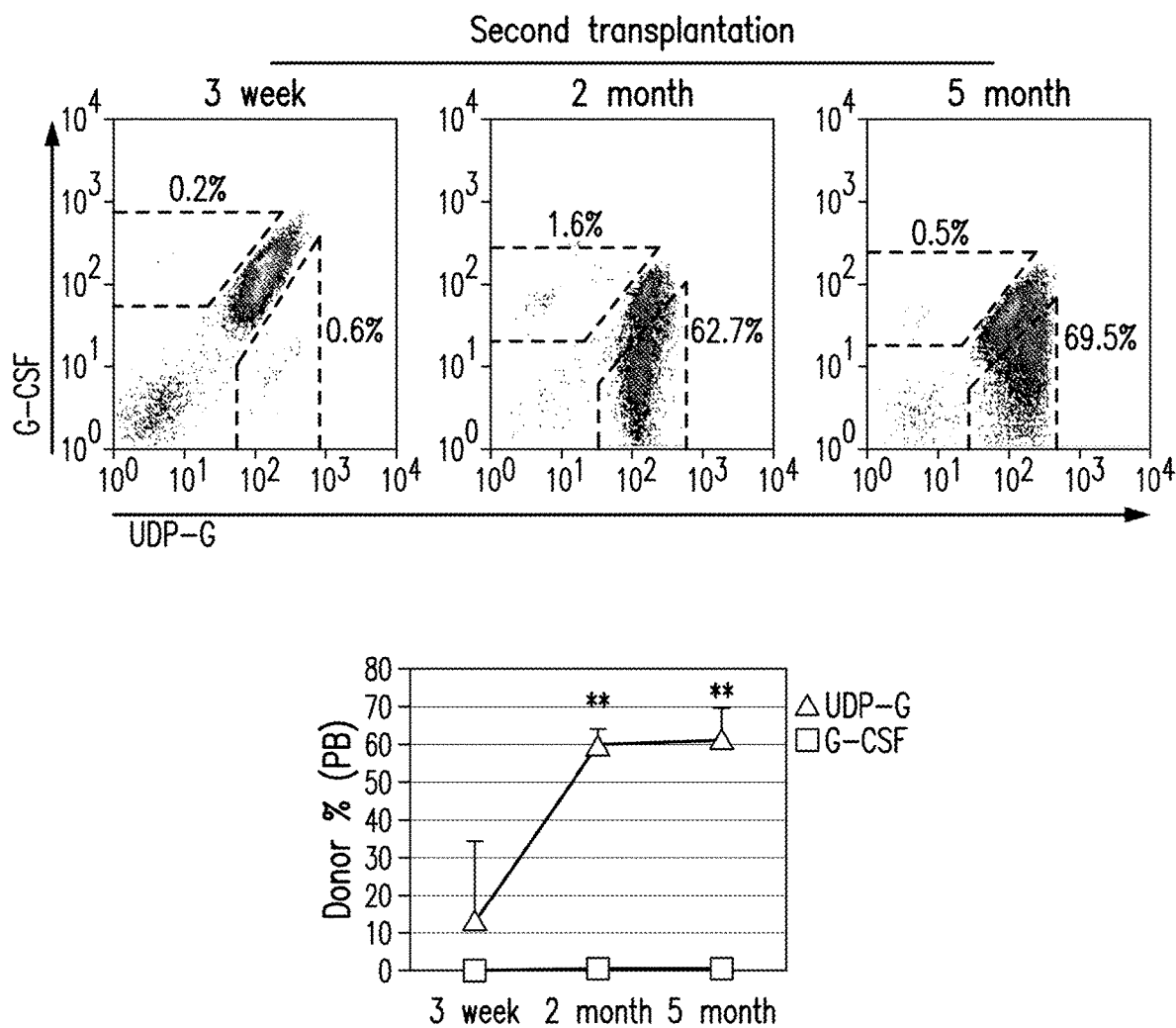
Figure 11E:
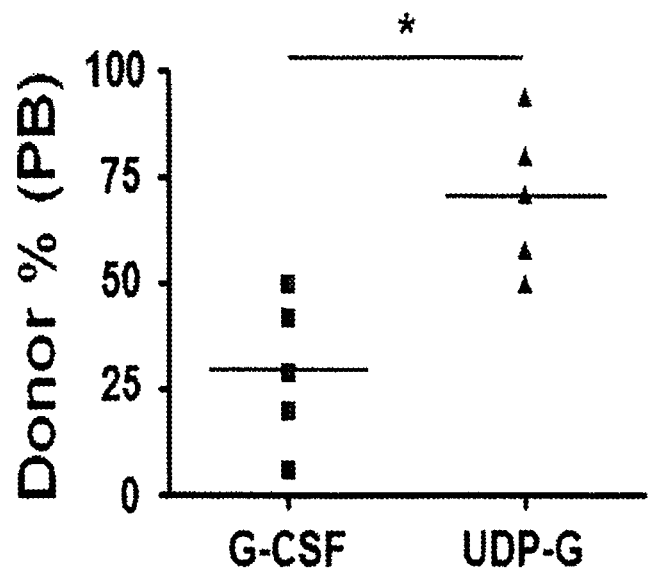
Figure 11E:
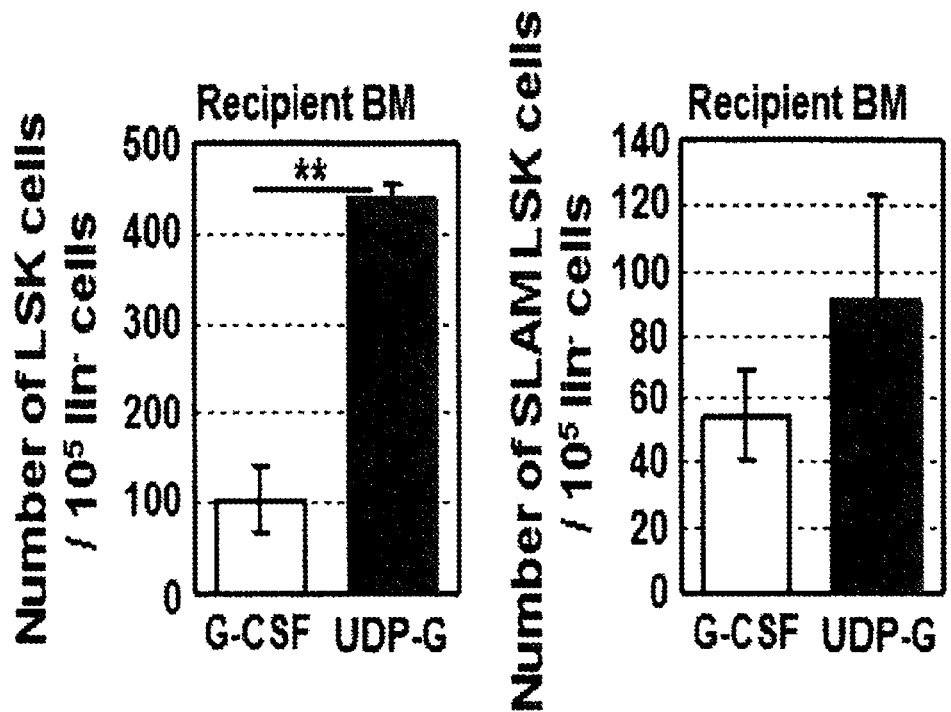

Serial transplantation represents the gold standard for assessing the long-term repopulation abilities. In order to further compare the long-term repopulation abilities of UDP-Glc- and G-CSF-mobilized HSPCs, we performed serial transplantation experiments under competitive settings. Primary recipients (CD45.1.2) were transplanted with UDP-Glc (CD45.2)- and G-CSF (CD45.1)-mobilized peripheral blood cells as shown in FIG. 3A. At 2-3 months post-transplant, bone marrow cells from primary recipients were sorted based on their expression of CD45. A mixture of equal numbers of CD45.1 (derived from G-CSF mobilization) and CD45.2 (derived from UDP-Glc mobilization) bone marrow cells were then transplanted into lethally irradiated secondary recipients (CD45.1.2). G-CSF mobilization-derived cells were out-competed by the cells derived from UDP-Glc mobilization in the secondary recipients over the whole post-transplantation period (FIG. 11D). To confirm the phenotypically defined bone marrow SLAM LSK cells in primary recipients (FIG. 11C) is correlated with stem cell function, we sorted SLAM LSK cells from the bone marrow of primary recipient animals and then tested their ability to support serial transplantation. When equal numbers of sorted bone marrow SLAM LSK cells were subjected to competitive serial transplantation, CD45.2+ SLAM LSK cells (derived from the bone marrow of recipients transplanted with UDP-Glc-mobilized PB) exhibited superior engraftment potential as compared to CD45.1+ SLAM LSK cells (derived from the bone marrow of recipients transplanted with G-CSF-mobilized PB) (FIG. 11E).

Figure 11F:
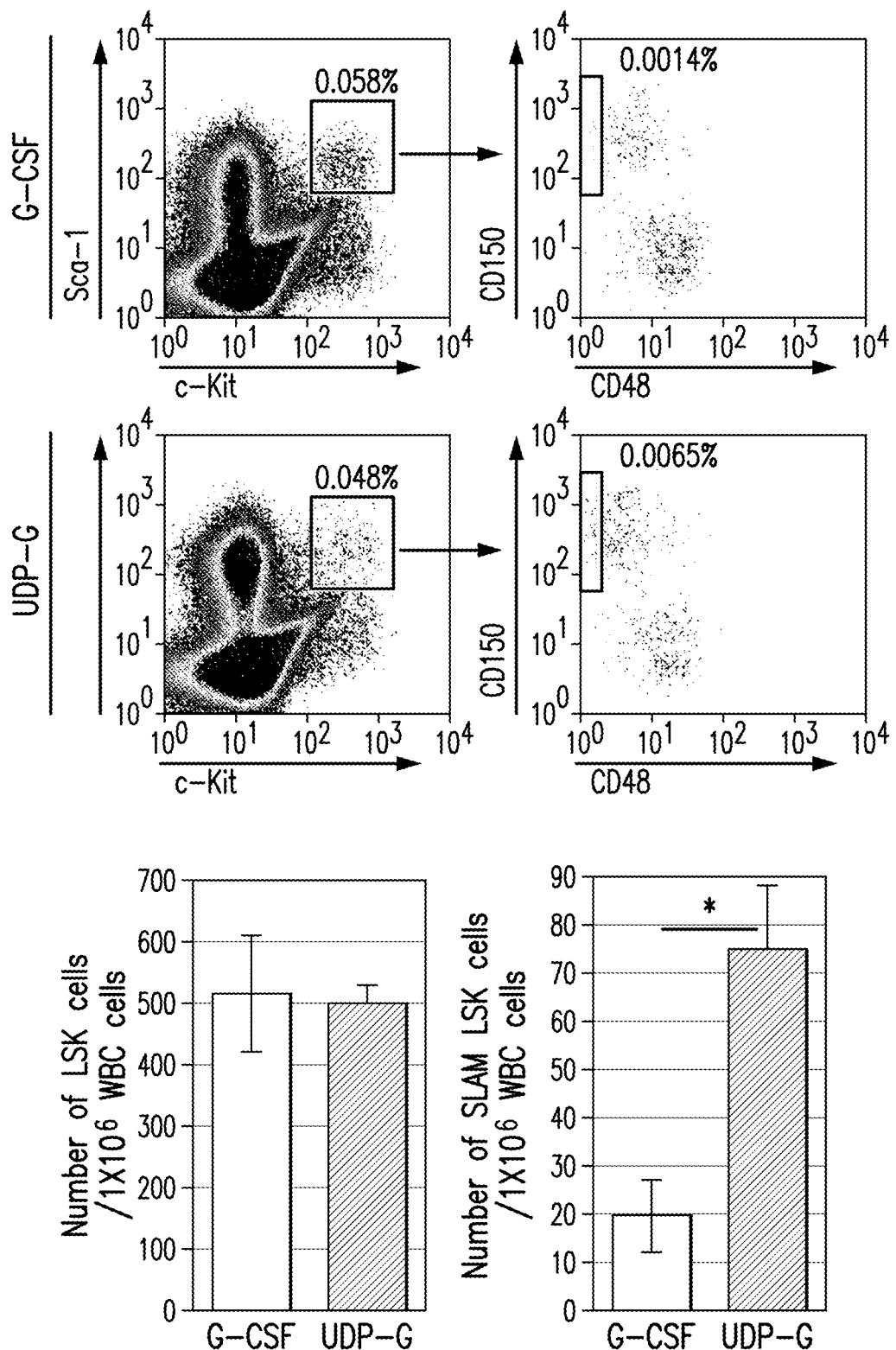
Figure 11G:
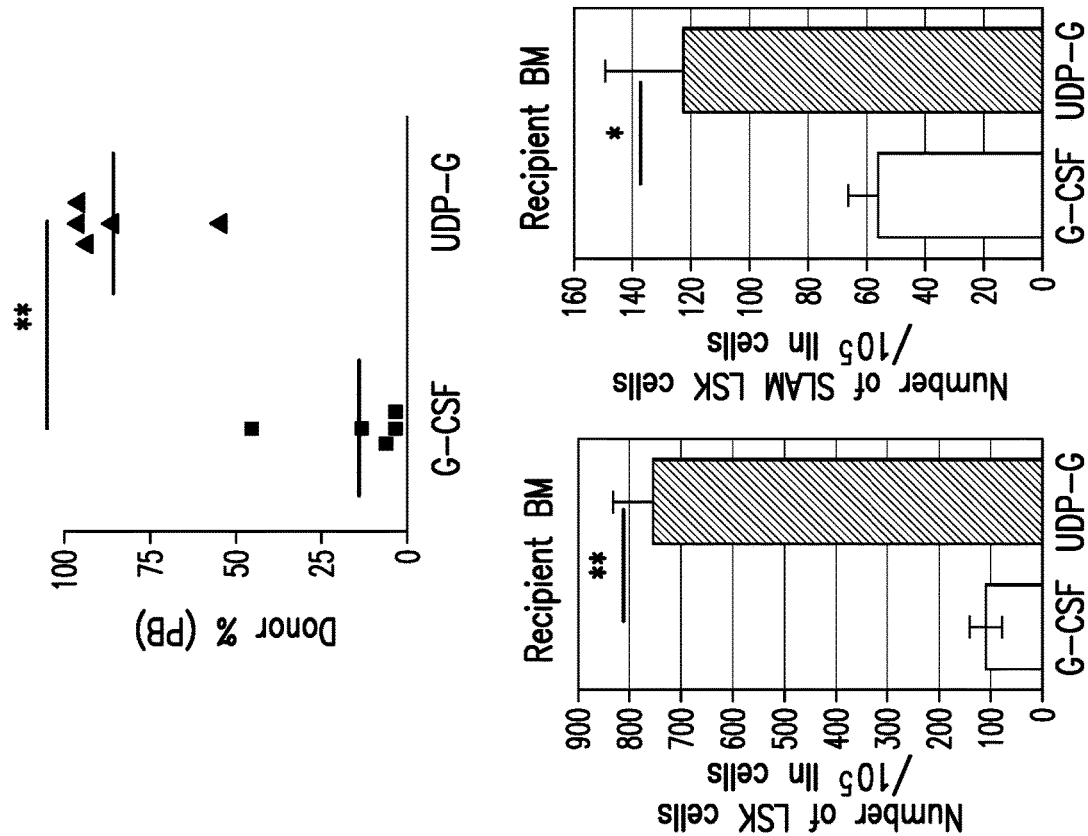

The preferential engraftment of long-term repopulating cells with UDP-Glc-mobilized cells may indicate the possibility that UDP-Glc mobilizes a more primitive subset of HSPCs such as SLAM LSK cells than G-CSF. UDP-Glc promoted LSK cell mobilization into the peripheral blood, with efficacy similar to that of G-CSF (0.048% vs. 0.058%) (FIG. 11F). However, UDP-Glc-mobilized LSK cells contained a significantly higher proportion of SLAM LSK cells compared to that of G-CSF-mobilized LSK cells (0.0065% vs. 0.0014%) (FIG. 11F). To directly compare HSC activity of UDP-Glc- and G-CSF-mobilized PBSC, we purified SLAM LSK cells from the peripheral blood of mice treated with G-CSF or UDP-Glc, and evaluated their HSC activity in a serial transplantation assay. UDP-Glc-mobilized peripheral blood SLAM LSK cells have greater HSPC activity than G-CSF-mobilized counterpart cells, as evidenced by their superior ability to reconstitute the hematopoietic system of irradiated recipients in serial transplantation assays (FIG. 11G). Taken together with the data shown above, these results strongly reinforce the hypothesis that UDP-Glc-mobilized HSPCs have enhanced self-renewal capacity when compared to G-CSF-mobilized HSPCs.

Figure 11H:
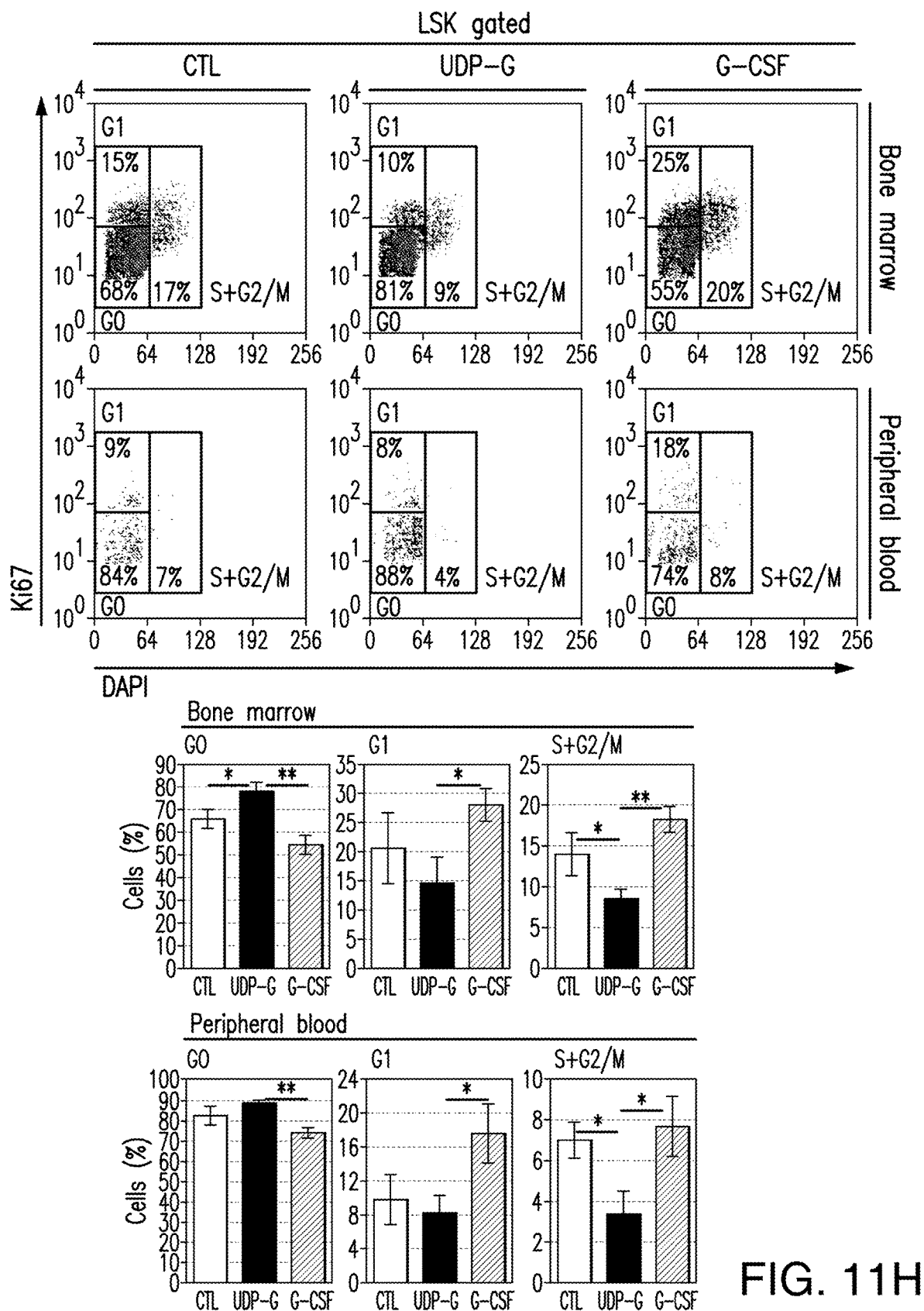

It is known that G-CSF administration promotes cell cycle entry by quiescent bone marrow HSC in both mice and baboon (29). Unlike G-CSF, UDP-Glc does not appear to function as a potent mitogen for bone marrow HSPCs (FIG. 11H); Kook et al.). Therefore, we hypothesized that UDP-Glc releases HSPCs from the niche without causing a significant disruption in their cell cycle quiescence, and this may improve the long-term engraftment ability of UDP-Glc-mobilized HSPCs. Indeed, compared with bone marrow LSK cells isolated from G-CSF-treated mice (hatched bars in FIG. 11H, upper right panel), bone marrow LSK cells isolated from UDP-Glc treated mice (black bars in FIG. 11H, upper right panel) contained a significantly higher proportion of cells in G0 and lower proportion in the G1, S, and G2/M phases. We then analyzed the cell cycle profiles for UDP-Glc-mobilized peripheral blood LSK cells. In comparison to G-CSF-mobilized peripheral blood LSK cells (hatched bars in FIG. 11H, lower right panel), UDP-Glc-mobilized peripheral blood LSK cells (black bars in FIG. 11H, lower right panel) showed an increased distribution in quiescent (G0) fraction and concomitant decreases in G1, S, and G2/M fractions.

Figure 11I:
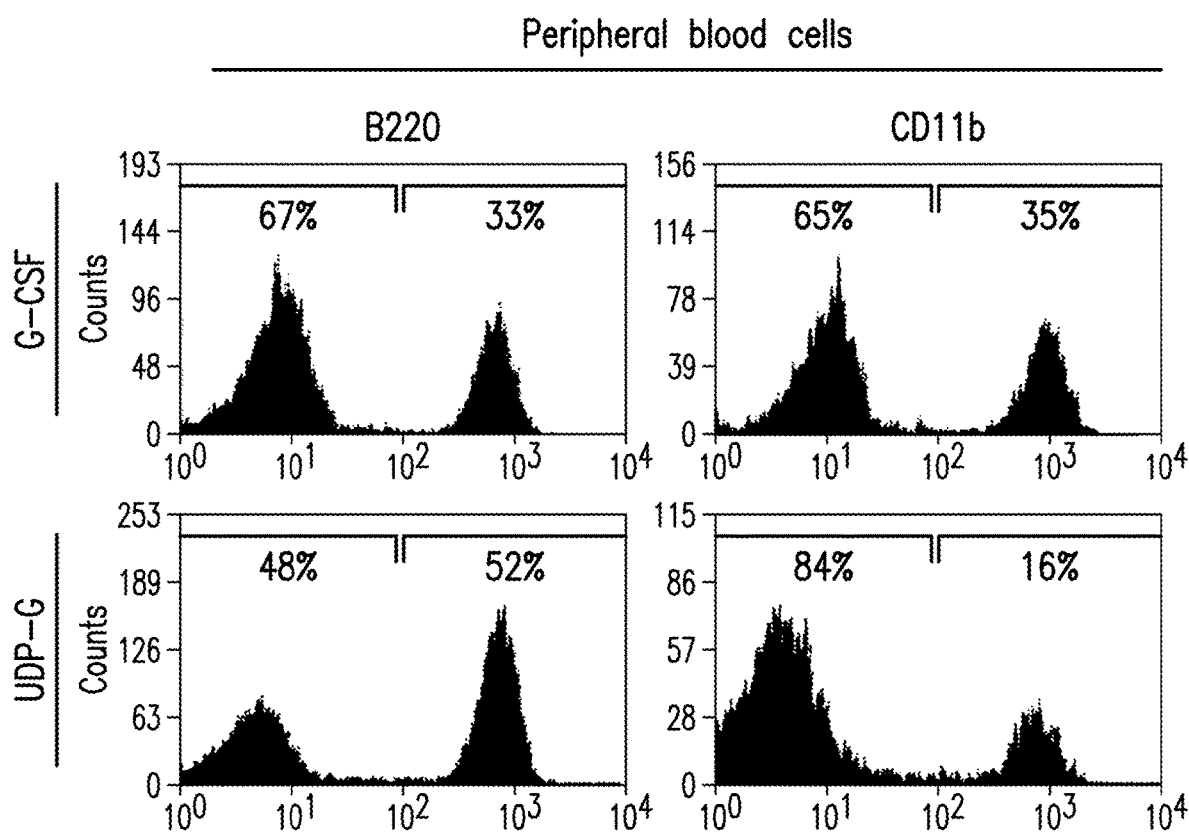
Figure 11J:
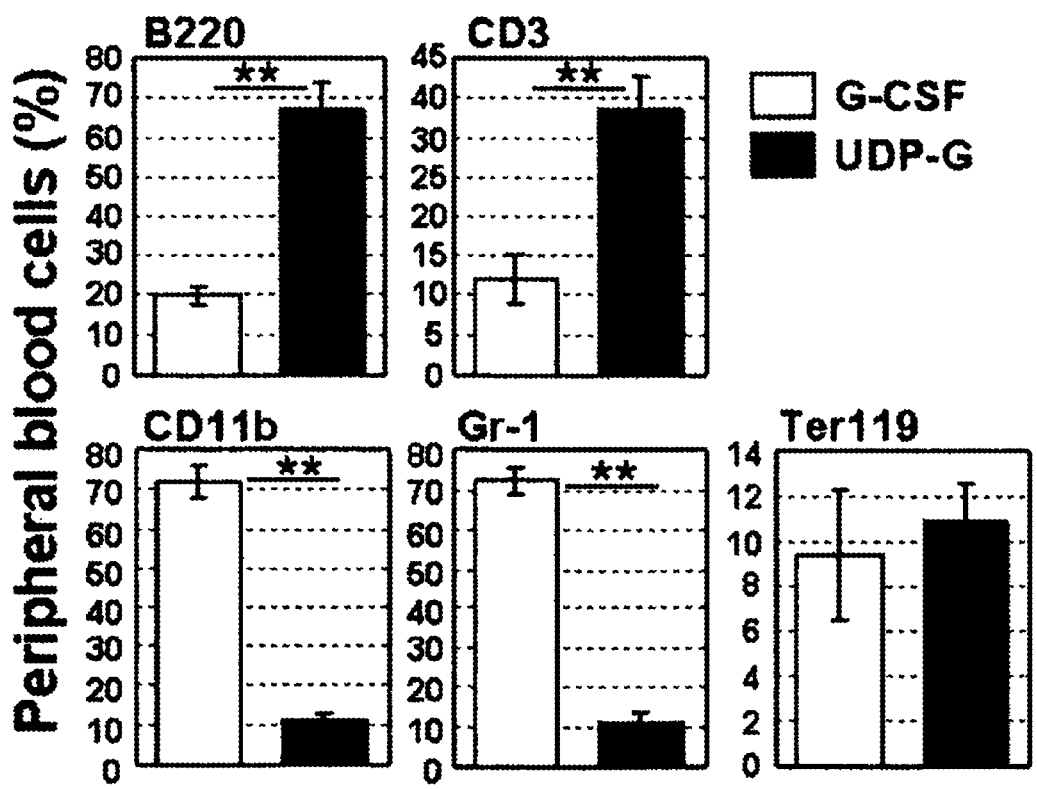

It is also noteworthy that UDP-Glc-mobilized cells, as compared to G-CSF-mobilized counterparts, exhibited a differentiation pattern skewed toward the lymphoid lineage in recipient mice (FIG. 11I). Of note, with more time elapsed from transplantation, the lineage skewing became more prominent: UDP-Glc-mobilized HSPCs became more skewed towards lymphoid cells with a longer post transplantation period (FIG. 11J). These data support the notion that UDP-Glc mobilizes a functionally distinct subset of HSPCs.

The Combination of UDP-Glc with G-CSF Improves Hematopoietic Stem Progenitor Cell Mobilization.

There is a keen interest in improving the mobilizing effects of G-CSF (10). Therefore, we investigated possible functional synergies between UDP-Glc and G-CSF. The mobilizing effect of UDP-Glc peaked 2-4 hours after the sixth daily consecutive injection (FIG. 9C). Standard G-CSF therapy requires four consecutive daily injections (10). Based on these results, the administration schedule of the compounds was designed to synchronize the maximal effect of each treatment as shown in FIG. 12A. We first assessed the effects of these regimens by assessing the colony forming activity. As shown in FIGS. 10A and 10B, the combination of G-CSF with UDP-Glc (vertically striped bars) mobilized a significantly higher CFU-Cs to peripheral blood and spleen compared with G-CSF alone (hatched bars). CAFC activity was also highly enriched in UDP-Glc/G-CSF-treated cells (FIG. 10C), indicating that G-CSF, when combined with UDP-Glc, performed better in in vitro HPC assays. Similarly, the combination of UDP-Glc and G-CSF was more efficient in mobilizing LSK cells than either alone (FIG. 10D). In the setting of competitive repopulation assay, UDP-Glc/G-CSF-mobilized cells were dominant over G-CSF-mobilized cells throughout the whole post-transplantation period (FIG. 12B). Although UDP-Glc alone was not as efficient as G-CSF in mobilizing in vitro colony forming HPCs (FIGS. 10A and 10B) or in vivo short-term repopulating cells (at one month posttransplantation in FIG. 11A), a combination of UDP-Glc and G-CSF markedly enhanced short-term repopulating activity compared with G-CSF alone, and this competitive advantage was continued over at least 5 months after transplantation (FIG. 12B). Accordingly, a significantly higher portion of LSK and SLAM LSK cells in recipient bone marrow were derived from UDP-Glc/G-CSF-treated mice (FIGS. 12C and 12D).

UDP-Glc Mobilizes Hematopoietic Stem Progenitor Cells Through the Alterations of the Osteoblast/Osteoclast Balance Mediated by Mitochondrial Superoxide.

Figure 13A:
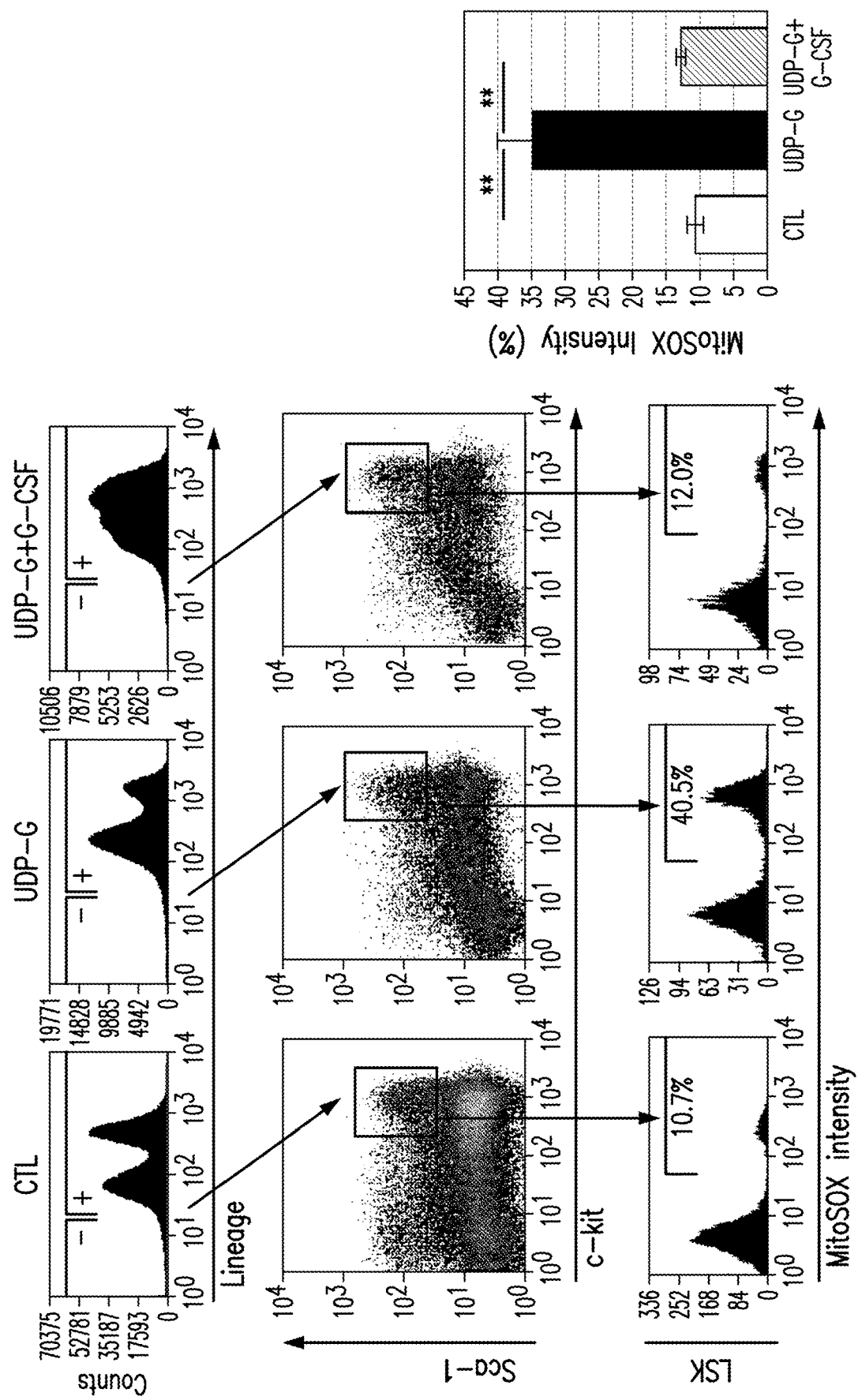
Figure 13B:
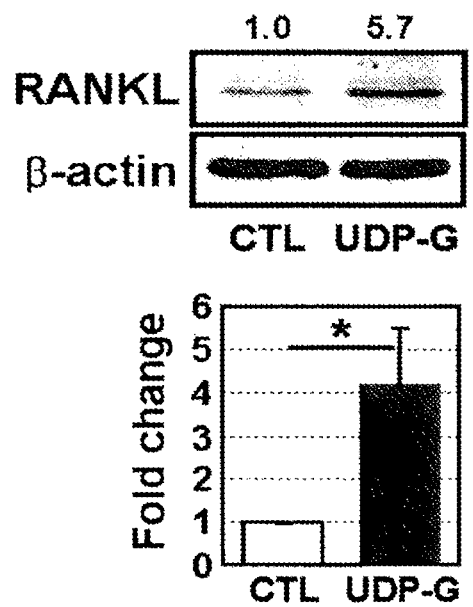
Figure 13C:
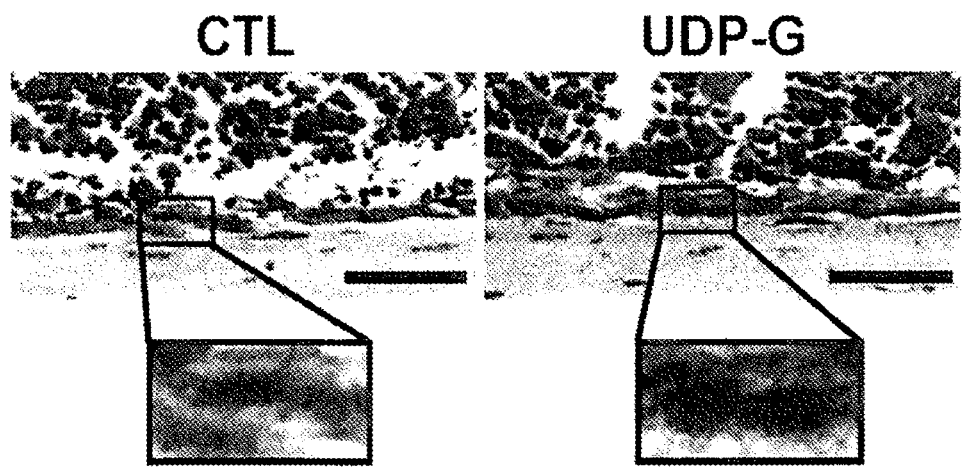
Figure 13D:
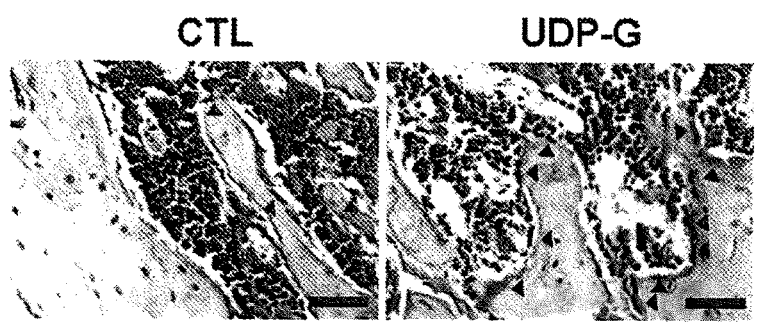
Figure 13E:
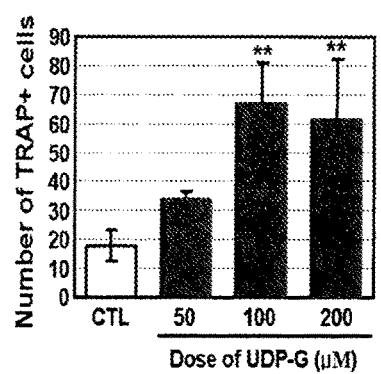
Figure 13F:
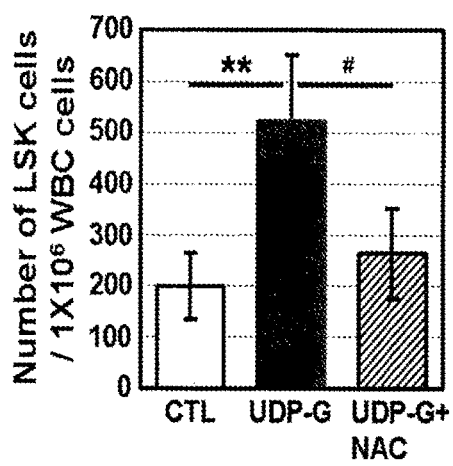
Figure 13G:
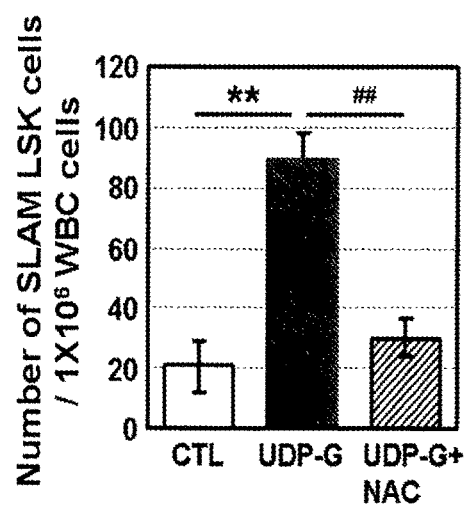

It has been recently proposed that Reactive Oxygen Species (ROS) signaling is closely associated with HSPC mobilization (30, 31). We examined whether UDP-Glc modulates the level of intracellular ROS levels in HSPCs. Since mitochondria are a major source of ROS, we measured the levels of mitochondrial superoxide in LSK cells. Upon UDP-Glc treatment, superoxide levels were significantly increased in LSK cells (FIG. 13A). As increased intracellular ROS levels upregulate RANKL expression (32, 33), which could in turn enhance HSPC mobilization (34), we examined whether UDP-Glc has any direct effect on RANKL expression. UDP-Glc induced an increase of RANKL expression, as demonstrated by both Western blot and immunohistochemical analyses (FIGS. 13B and 13C). RANKL is a potent driver of osteoclast formation, and tipping the balance in favor of osteoclasts leads to mobilization of HSPCs (27). We observed a higher proportion of osteoclast cells in UDP-Glc-treated mice, as evidenced by the expression of the osteoclast-associated enzyme tartrate-resistant acid phosphatase (TRAP) (FIG. 13D). However, this UDP-Glc-induced osteoclastogenesis was transient, since the ratio of osteoblasts to osteoclasts returned to the pre-stimulation baseline value 3-4 weeks after the treatment was stopped (See FIG. 18). In the in vitro osteoclast differentiation assay, UDP-Glc also promoted the generation of osteoclasts (FIG. 13E).

Figure 13H:
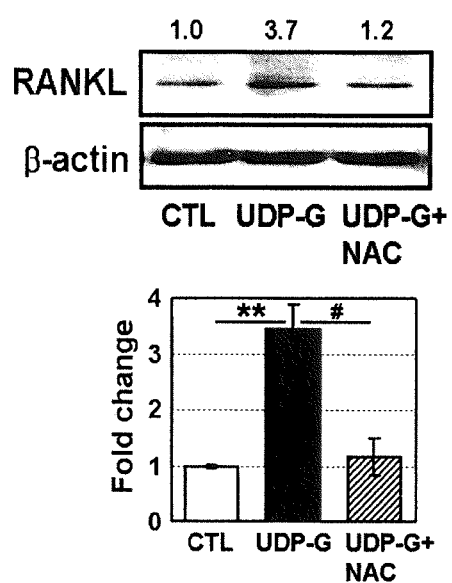
Figure 13I:
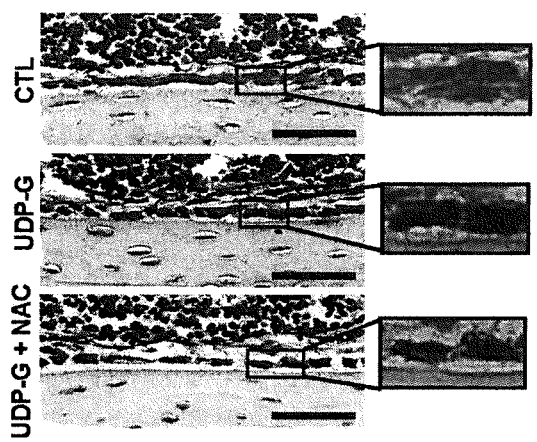
Figure 13J:
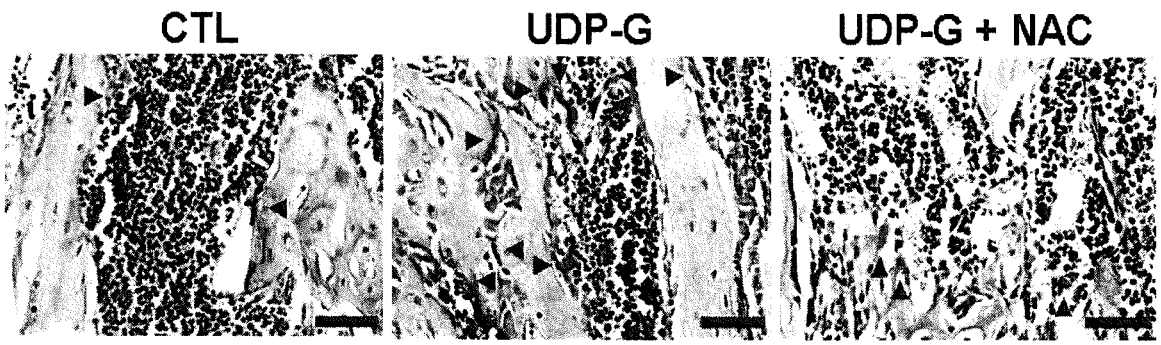

To investigate if the elevated superoxide levels are indeed potential mediators of the UDP-Glc-mediated HSPC mobilization, an antioxidant, N-Acetylcysteine (NAC), was administered. NAC was able to significantly abrogate the LSK and SLAM LSK cell mobilization induced by UDP-Glc (FIGS. 13F and 13G), suggesting that superoxide acted as potential mediators in UDP-Glc mobilization. We then asked whether the abrogation of UDP-Glc mobilization by NAC is through inhibition of RANKL expression. Indeed, RANKL expression was notably lowered in NAC-treated animals in comparison with UDP-Glc-treated animals (FIGS. 13H and 13I). Similarly, the level of UDP-Glc-induced osteoclastogenesis was significantly suppressed with NAC treatment (FIG. 13J). Without being bound to any particular theory, it is plausible that UDP-Glc increases ROS levels, and this in turn enhances RANKL-induced osteoclast differentiation, leading to HSPC mobilization. Interestingly, while the combination of UDP-Glc and G-CSF augmented HSPC mobilization, it significantly reduced mitochondrial superoxide levels compared to UDP-Glc alone (FIG. 13A, right panel). This suggests that the combination of UDP-Glc and G-CSF augments its mobilizing effect through as yet unknown mechanisms, rather than via a further increment of ROS level.

Figure 14A:
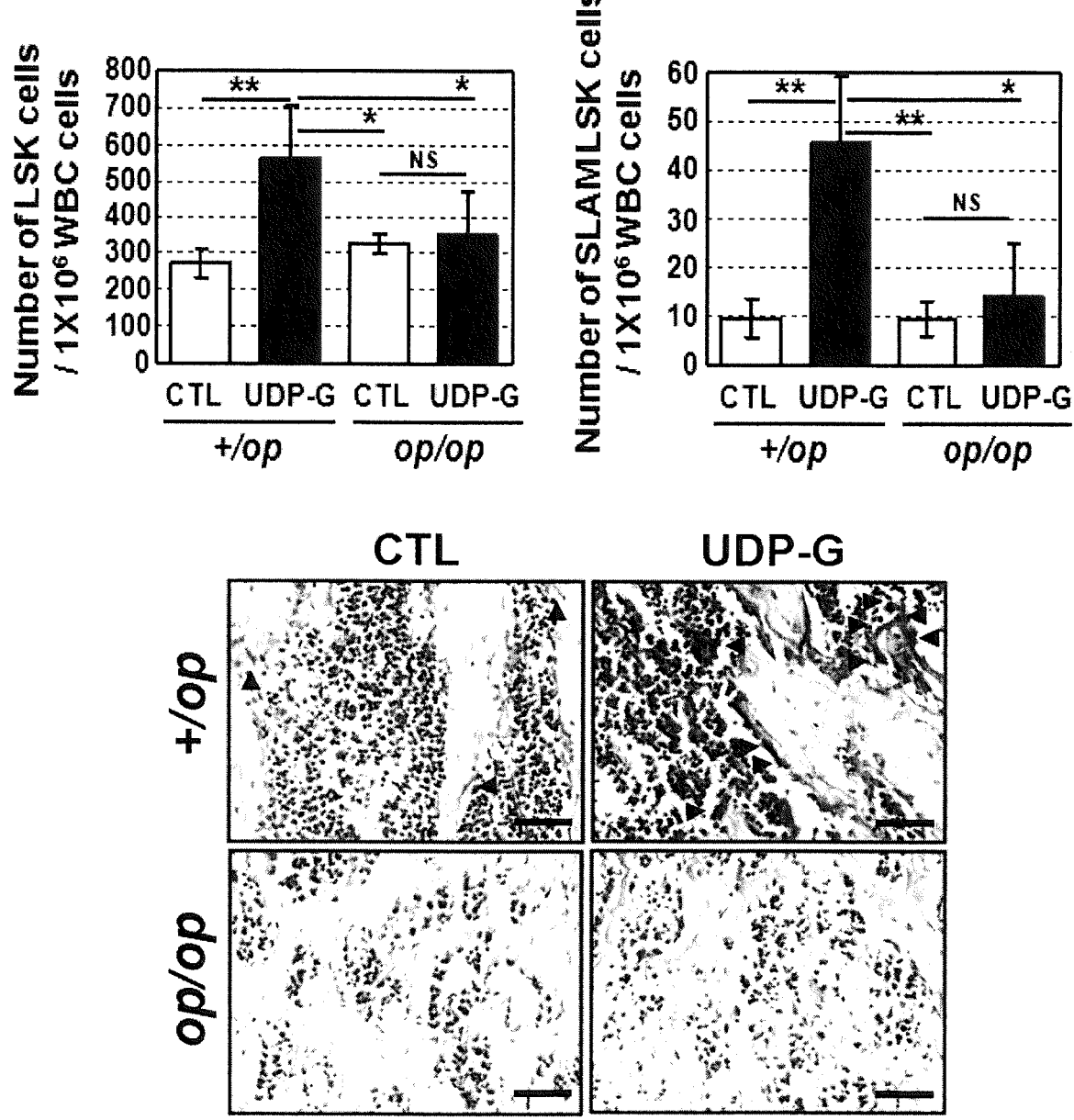

Controversy still exists regarding the role of osteoclasts in regulating HSPC mobilization (34-37) raising a question as to whether osteoclasts indeed play an essential role in UDP-Glc-mediated HSPC mobilization. To address this question, we first utilized the osteopetrotic (op/op) mouse model. Mice homozygous for the op mutation exhibit a severe deficiency of osteoclasts so that this strain can serve as a model to investigate the role of osteoclasts in UDP-Glc-mediated HSPC mobilization (38). Administration of UDP-Glc into littermate control mice (CTL; +/op) induced osteoclastogenesis and promoted the mobilization of LSK cells and SLAM LSK cells (FIG. 14A). However, op/op mice given the same treatment showed no changes in osteoclastogenesis and failed to show a statistically significant increase in the number of peripheral LSK and SLAM LSK cells (FIG. 14A). These results suggest that osteoclasts play an important role in the regulation of UDP-Glc-mediated HSPC mobilization.

Figure 14B:
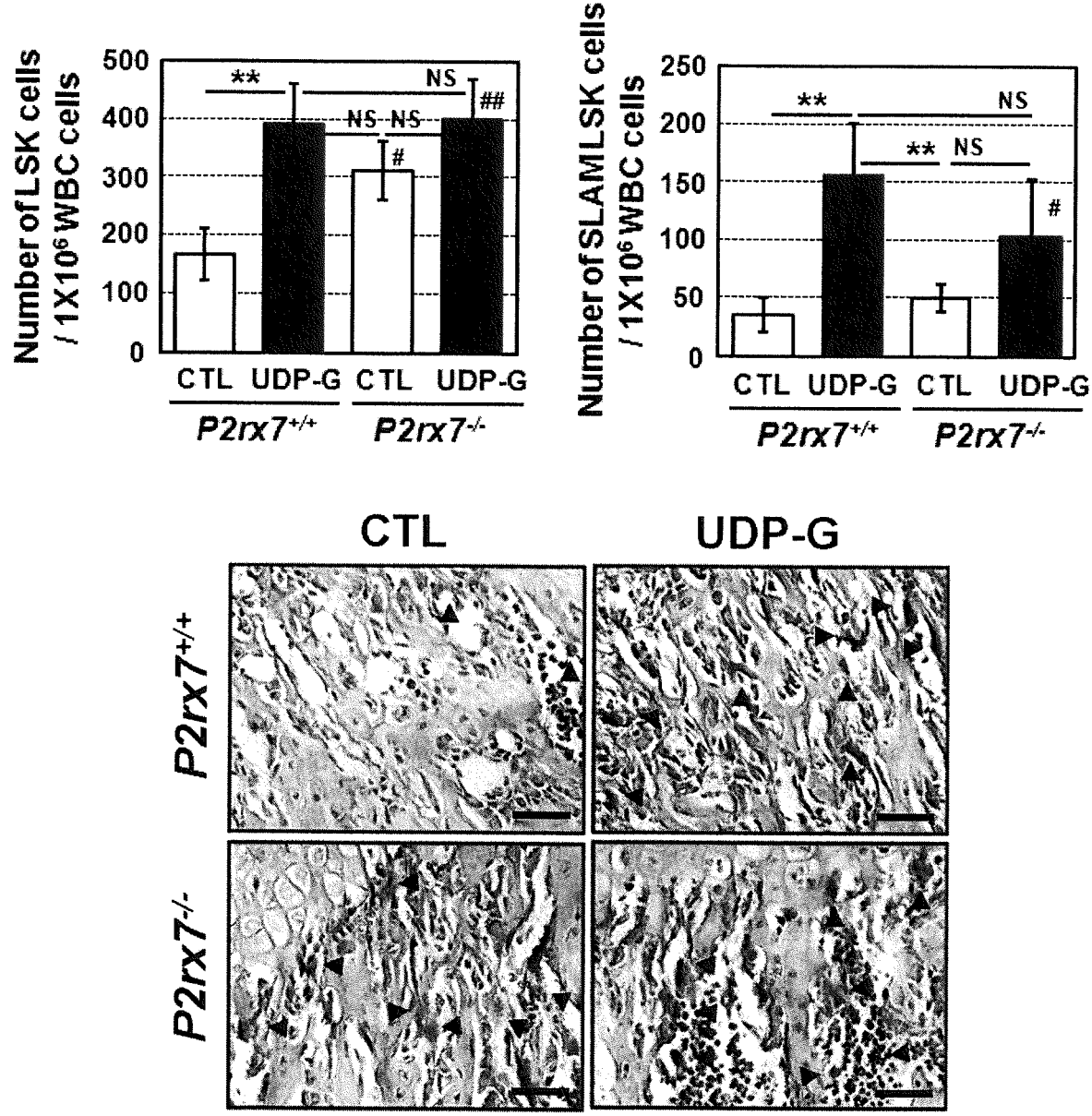
Figure 14C:
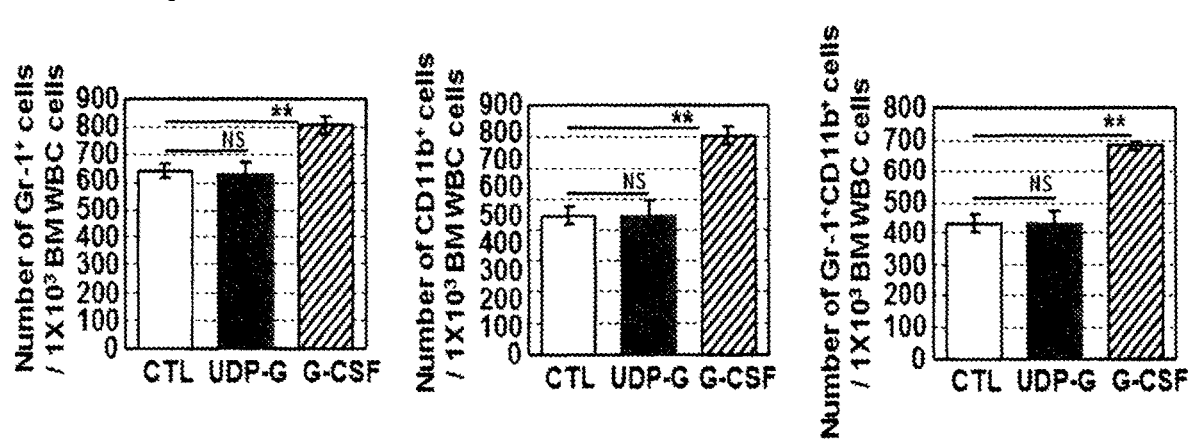

To further study the impact of osteoblasts/osteoclasts in UDP-Glc-mediated HSPC mobilization, P2X7 deficient mice were analyzed. Deficiency of P2X7 in mice results in impaired bone formation and excessive bone resorption (39). In accordance with this finding, a significantly increased numbers of osteoclasts were detected in non-treated P2X7 KO mice (FIG. 14B). UDP-Glc did not lead to a further noticeable increase in osteoclast activity in P2X7 KO mice. Similarly, UDP-Glc-treated P2X7 KO mice showed no significant increase in the number of peripheral LSK cells, compared to the vehicle-treated P2X7 KO mice (FIG. 14B, upper left). There was a trend towards moderately increased numbers of SLAM LSK cells (~1.9 fold) in the blood of UDP-Glc-injected P2X7 KO mice. However, this did not reach statistical significance. Of note, steady-state levels of circulating LSK cells were elevated in P2X7 KO mice compared to those in WT mice (FIG. 14B, upper left), suggesting the possibility that P2X7 deficiency may lead to constitutive LSK cell mobilization in part through increased osteoclast activity. Without being bound to any particular theory, the results described above suggest a potential role of osteoclasts in UDP-Glc-induced HSPC mobilization.

Figure 14D:
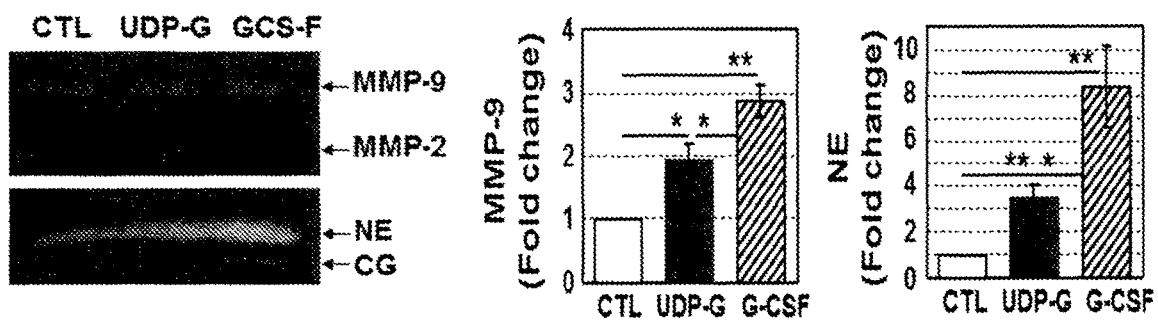

Meanwhile, since the proteolytic enzymes produced by monocytes/granulocytes are also important contributors mediating HSPCs mobilization (40), we examined whether UDP-Glc could induce the release of proteases from monocytes/granulocytes. As previously documented, there were overall increases in the percent of CD11b+ and/or Gr-1+ cells in the bone marrow of G-CSF-treated mice (hatched bars in FIG. 14C). In contrast, UDP-Glc did not lead to any notable changes in the percent of CD11b+ and/or Gr-1+ cells in the bone marrow (black bars in FIG. 14C). Elevated levels of the proteolytic enzymes such as matrix metalloproteinase-9 (MMP-9), neutrophil elastase (NE), and cathepsin G (CG) were observed in mice treated with G-CSF (FIG. 14D). UDP-Glc also elevated the level of MMP-9 and NE but at a significantly lower level compared to those treated with G-CSF (FIG. 14D). There were no significant differences in MMP-2 and CG levels between vehicle- and UDP-Glc-injected groups.

Figure 14E:
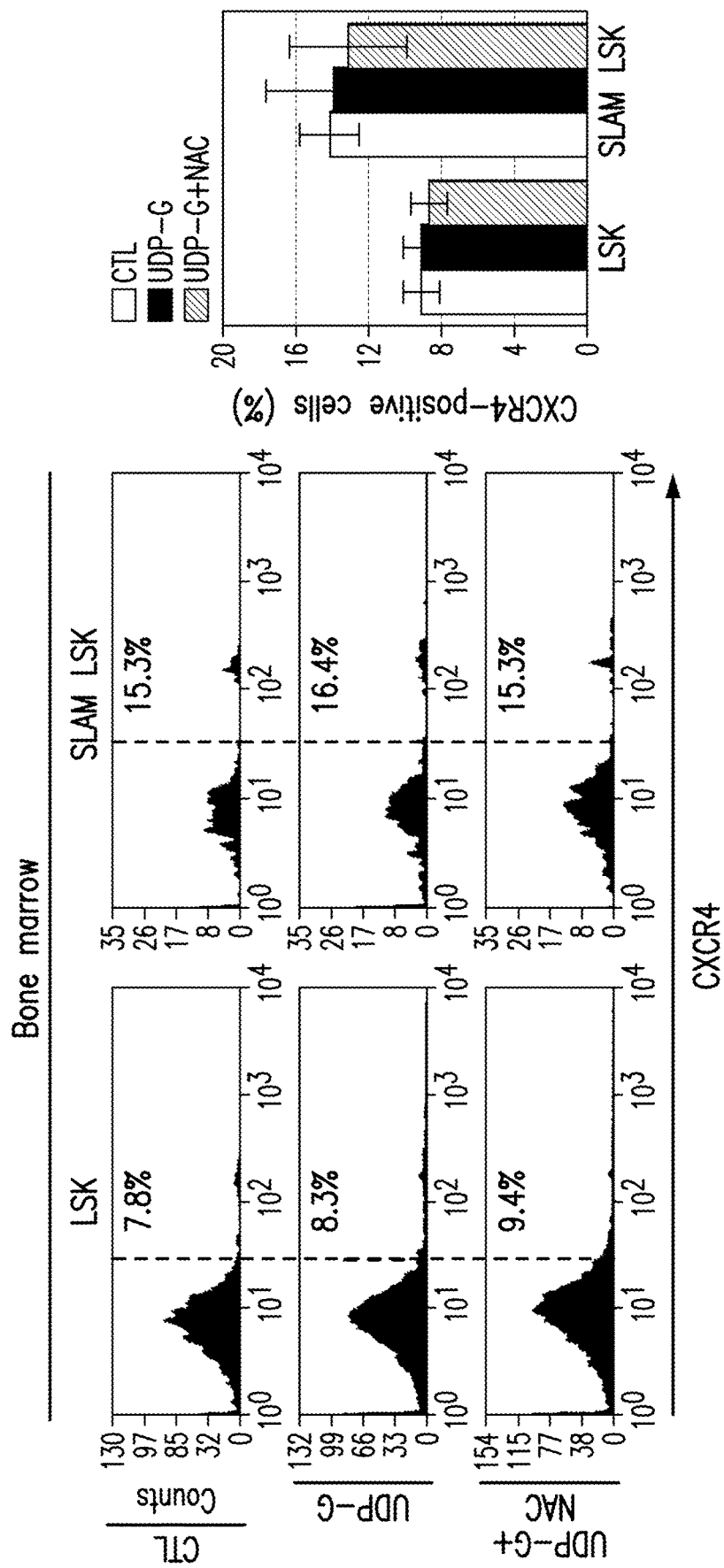
Figure 14E:
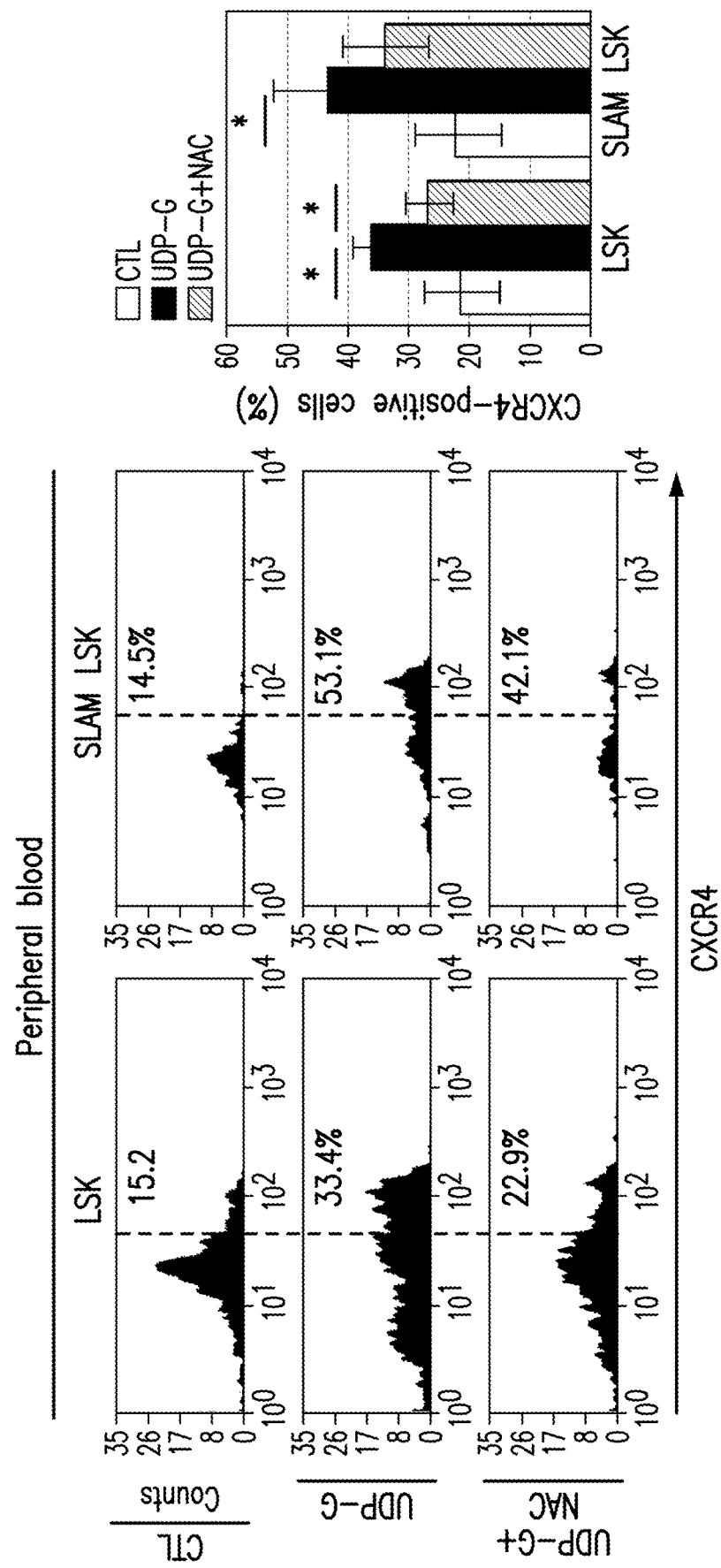
Figure 14F:
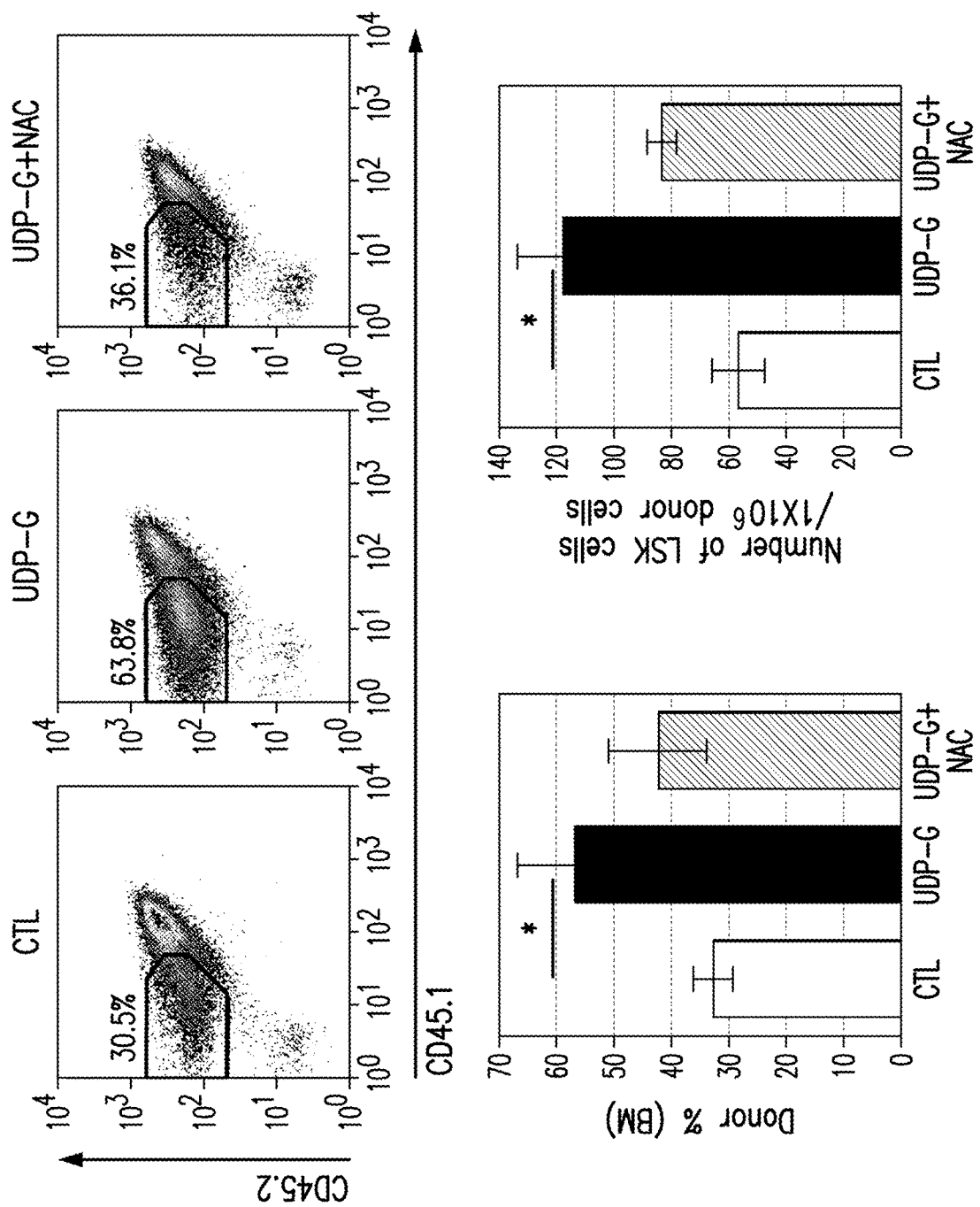

We then determined the effect of UDP-Glc on the expression of CXCR4, which plays a key role in homing and mobilization of HSPCs (41). UDP-Glc-treated mice displayed no significant change in the percentage of CXCR4 expressing cells in their bone marrow LSK and SLAM LSK cells (FIG. 14E, upper panel). In contrast, UDP-Glc treatment led to an increased CXCR4 expression in peripheral (circulating) LSK (33.4 vs. 15.2%) and SLAM LSK (53.1% vs. 14.5%) populations (FIG. 14E, lower panel). NAC was able to abrogate the increase of CXCR4 expression induced by UDP-Glc, albeit not completely. When injected, UDP-Glc-mobilized peripheral blood cells homed to the bone marrow more efficiently than vehicle-treated peripheral blood cells (FIG. 14F). Homing of UDP-Glc-mobilized cells was inhibited by NAC pretreatment. A significantly higher number of donor-derived LSK cells (*P<0.05) were found in the bone marrow of mice transplanted with UDP-Glc-mobilized peripheral blood cells than in those of mice transplanted with vehicle-treated peripheral blood cells (FIG. 14F). However, considering that UDP-Glc-mobilized peripheral blood contained greater numbers of LSK cells FIG. 10D), UDP-Glc doesn't appear to have a major effect on the homing capacity of the mobilized LSK cells. We were unable to determine the number of SLAM LSK cells that homed to the bone marrow (especially in mice transplanted with vehicle-treated cells), since the majority of injected cells, including HSCs, are trapped in the lung, kidney and liver during their journey to the bone marrow, and the number of events acquired for the analyses of SLAM LSK cells was far too low for a reliable enumeration.

Figure 15A:
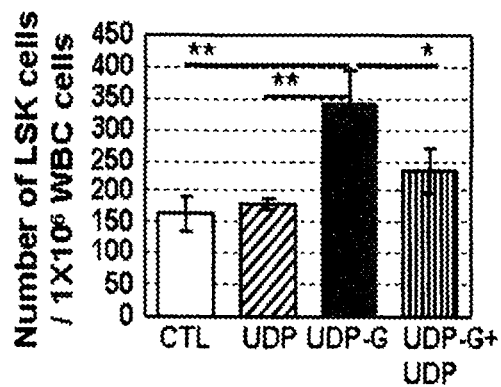
Figure 15B:
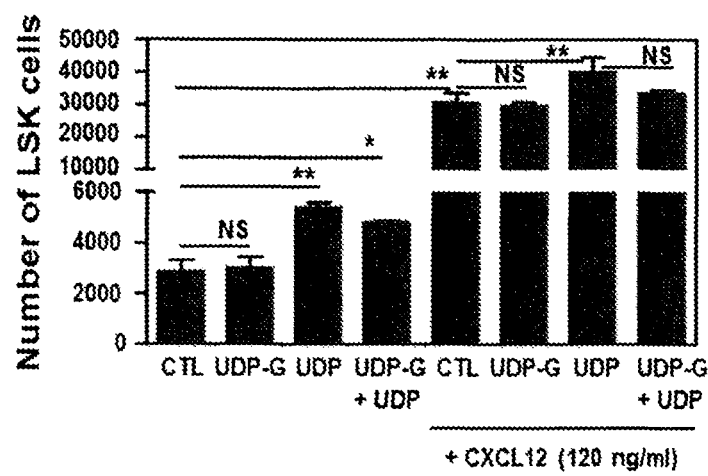

It is previously known that UDP antagonizes the action of UDP-Glc (42). We thus evaluated the effects of UDP on UDP-Glc-mediated HSPCs migration. UDP, alone, did not elicit any appreciable change in the number of LSK cells in the peripheral circulation (FIG. 15A). However, when UDP was simultaneously treated with UDP-Glc, it antagonized UDP-Glc-induced LSK cell mobilization. (FIG. 15A). Interestingly, UDP could chemoattract LSK cells in vitro in the presence or absence of CXCL12 (FIG. 15B). Conversely, UDP-Glc treatment led to a moderate inhibition of UDP-induced chemotaxis but this did not reach the statistical significance.

7.3 Discussion

Mobilized HSPCs could regenerate a complete hematopoietic system for cancer patients with hematolymphoid malignancies or solid tumors. Yet more than 20 percent of patients fail to mobilize sufficient stem cells for transplantation (43). These include patients who were previously treated with intensive radiation and chemotherapy; those who have genetic disorders such as Fanconi's anemia; and those who are over 60 years of age (10, 44). A combination of G-CSF with cytotoxic agents improves HSPC mobilization in the poor mobilizer patients, but often accompanies serious side effects (45). Such limitations necessitate the discovery of novel mobilizing regimens, so that it may be used to tailor therapy on an individual basis. Data presented in the current study establish a novel aspect of a nucleotide sugar, UDP-Glc, in the HSPC mobilization.

Functional characteristics of HSPCs, such as homing, engraftment, cell cycle status and self-renewal activity vary according to their tissue of origin (13, 46). For example, circulating blood stem cells can't compete effectively against bone marrow-derived stem cells for long-term multilineage repopulation (47). Therefore, when mobilized cells are assessed for their functional activity, it is more legitimate to compare cells from same tissue origin, i.e. G-CSF to compare cells from same tissue origin, i.e. G-CSF-mobilized peripheral blood vs. UDP-Glc-mobilized peripheral blood. To this end, we adapted a competitive repopulation assay in which a mixture of equal numbers of UDP-Glc- and G-CSF-mobilized blood cells are transplanted into conditioned recipients (FIG. 17), which allows a direct comparison of UDP-Glc-mobilized cells to G-CSF-mobilized cells under the same microenvironment.

While UDP-Glc-mobilized cells had a lower capacity to form in vitro colonies compared with G-CSF-mobilized cells, serial transplantation experiments showed that UDP-Glc-mobilized cells have greater capacity than G-CSF-mobilized cells to engraft lethally irradiated recipients, suggesting that UDP-Glc preferentially mobilizes long-term self-renewing HSPCs. UDP-Glc-mobilized peripheral blood contained a greater numbers of SLAM LSK cells than G-CSF-mobilized cells (FIG. 11F), which could provide a potential explanation for their superior long term repopulating ability. However, when sorted peripheral SLAM LSK cells from UDP-Glc mobilization were compared with equal number of counterpart cells from G-CSF mobilization in competitive serial transplantation models (FIG. 11F), SLAM LSK cells derived from UDP-Glc mobilization consistently displayed superior long-term repopulating ability, suggesting that the qualitative advantage of UDP-Glc-mobilized HSPCs can also account for the superior engraftment potential of UDP-Glc mobilized cells.

Cytokine-induced stem cell mobilization is often accompanied by profound changes in number and composition of accessory cells contained within the PBSC collection (48). In contrast, UDP-Glc did not cause any noticeable quantitative changes in the accessory cell compartment (FIG. 10H). Accessory cells, especially T cells, exert immune regulatory function and influence the development of graft versus host disease (GVHD) and graft-versus-leukemia (GVL) in the allogeneic setting (49). UDP-Glc appears to have minimal effects on peripheral T cell numbers, which may be beneficial in reducing the incidence and severity of GVHD in the setting of certain clinical situations. When transplanted, the skewing of the lymphoid/myeloid ratio toward the lymphoid lineage was pronounced in the UDP-Glc-mobilized HSPCs (FIGS. 11I and 11J). In addition, UDP-Glc did not disrupt cell cycle quiescence of HSPCs and this could contribute to the enhanced long-term engraftment potential of UDP-Glc-mobilized cells. All these properties taken together indicate that UDP-Glc is a previously unrecognized HSPC mobilizer that egresses a functionally distinct subset of the HSPCs.

The molecular mechanisms that are responsible for HSPC mobilization are complex and confounding. Redox signaling plays a central role in regulating HSPC mobilization (30), because many of the cytokines, chemokines and adhesion molecules associated with HSPC mobilization are regulated through a redox-regulated process (50). Mice treated with UDP-Glc expressed high levels of mitochondrial superoxide in their HSPCs. Lowering these mitochondrial superoxide levels by antioxidants significantly reduced the mobilizing effect of UDP-Glc and this coincided with the reduction in RANKL and osteoclastogenesis (FIG. 13). These results, therefore, suggest that ROS play a role in mediating the UDP-Glc-induced HSPC mobilization through an increase of RANKL expression and osteoclast activity.

It has been shown that osteoclasts mediate HSPC egress from the endosteal osteoblastic niche by degrading endosteal components (34, 35, 37). However, other lines of evidence indicate that osteoclasts are dispensable for HSC mobilization (36). UDP-Glc mobilization was not achievable in mouse models of osteopetrosis (Op/Op), suggesting that osteoclast formation is required for UDP-Glc-mediated HSPC mobilization. Meanwhile, P2X7 knockout mice, which display excessive osteoclast resorption activity at 6-8 weeks of age (39), showed higher number of circulating LSK cells than WT mice even under steady-state conditions. UDP-Glc does not seem to further increase osteoclast formation in P2X7 KO mice that were already osteoporotic, and no significant change was observed in the number of peripheral LSK cells in UDP-Glc-injected P2X7 KO mice. Taken together, it is conceivable that the extent of osteoclast formation in response to UDP-Glc is functionally associated with the ability of UDP-Glc to mobilize HSPCs.

The other mechanisms for UDP-Glc-induced mobilization would be an indirect effect involving activation of neutrophils with the subsequent release of proteases (51): increased levels of proteases can attack several target proteins, including CXCR4, CXCL12 (SDF-1α), or VCAM-1, leading to inactivation of CXCR4/CXCL12- or VCAM-1/VLA-4-dependent signals and thus cell migration out of bone marrow. Unlike G-CSF, however, UDP-Glc had no effect on granulocyte and monocyte mobilization (FIG. 10H). Meanwhile, UDP-Glc was also able to mobilize HSPCs in G-CSFR deficient (Csf3r−/−) mice, although to a lesser extent than in WT mice (FIG. 10I), suggesting that granulocyte and monocyte mobilization does not appear to be essential in UDP-Glc-mediated mobilization. Despite no noticeable impact on granulocytes and monocytes, there were trends toward modest increases in the levels of MMP-9 and NE (but not MMP-2 and CG) in the bone marrow of UDP-Glc-injected mice (FIG. 14D). However, this increase was substantially lower in magnitude compared to those of G-CSF treated mice. We could not rule out the possibility that proteolytic enzymes contribute, at least to some extent, to UDP-Glc-mediated mobilization, although proteolytic enzymes don't appear to be a major contributor.

UDP-Glc treatment increased CXCR4-cell surface expression in peripheral HSPCs but not in bone marrow HSPCs (FIG. 14E). It remains an open question as to whether or not the increased CXCR4 expression by UDP-Glc is associated with increased homing capacity. Intravenous injection of equal numbers of sorted peripheral LSK and SLAM LSK cells from UDP-Glc- and vehicle-injected mice (in the presence or absence of CXCR4 antagonist) may allow us to evaluate the homing capacity of UDP-Glc-mobilized HSPCs. However, because LSK and SLAM LSK cells are present in blood at a very low frequency (especially, in the blood of vehicle-injected mice), and because the majority of injected LSK or SLAM SLK cells will be trapped in the lung and/or the liver before reaching the bone marrow, the number of mice required to obtain a statistically reliable flow data is prohibitively high, so the experiment was not performed in this study.

UDP-Glc is known to bind the P2RY14 receptor. It is therefore of interest to investigate whether UDP-Glc triggers HSPC mobilization through P2RY14 receptor-dependent or -independent mechanisms (or both). While this area warrants further study using animal models such as conditional P2ry14 knockout animals, there are contradictory reports that UDP-Glc is not a functionally relevant ligand at P2RY14 receptor (52, 53). It is also noteworthy that HSPC mobilization is often mediated through multiple trans-acting signals rather than ligand-receptor interactions (54, 55). Recent studies established the biological significance of extracellular nucleotides in migration and engraftment of human HSPCs (18, 19): UTP has the capacity to chemoattract human CD34+ cells and enhances engraftment of human HSPCs. Because chemokine/chemokine receptor axes play critical role in HSPC mobilization, it draws attention that P2RY14 also encodes a 7-transmembrane G-protein coupled receptor (GPCR) with a chemokine receptor signature (e.g., DRY motif in the 3rd intracellular domain) (56). However, UDP-Glc doesn't appear to have chemoattractive properties on mouse LSK cells. Rather, UDP, which antagonizes the action of UDP-Glc (42), has chemotactic activity and attracts mouse LSK cells (FIG. 15).

Quiescent HSCs have higher long-term repopulating abilities than HSCs in active cell cycle (57). Since UDP-Glc does not affect cell cycle quiescence of bone marrow-resident HSPCs (FIG. 11I), this could contribute to the enhanced long-term engraftment potential of UDP-Glc-mobilized cells. How UDP-Glc mobilizes HSPCs without disrupting cell cycle quiescence remains unknown. Unlike cytotoxic drugs- and/or cytokines-based mobilizations that are often accompanied by marked changes in cell proliferation, cell death and bone marrow sinusoidal endothelium, UDP-Glc caused no notable changes in any of those. UDP-Glc also had no effects on cell proliferation (FIG. 16; Kook et al., unpublished results) that might conceivably be an underlying reason for the cell cycle quiescence of UDP-Glc-mobilized HSPCs. It is also conceivable, although still speculative, that UDP-Glc may regulate cell cycle progression through modulating cyclin-dependent kinase inhibitors.

Figure 19:
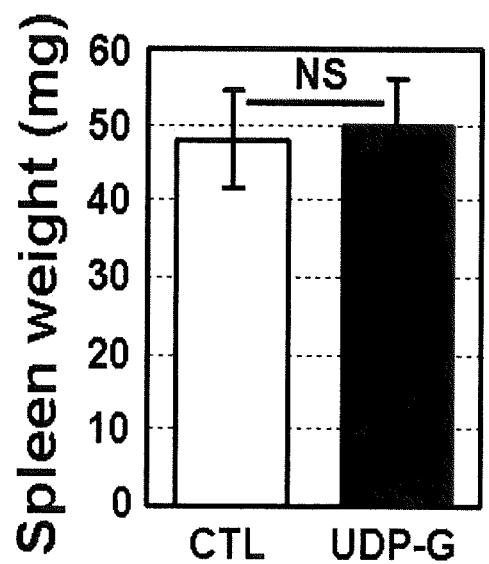

UDP-Glc is a naturally occurring metabolite in the human body, so that it may mitigate many of the side effects which are often associated with other synthetic mobilizers. Indeed, none of the UDP-Glc-treated animals showed signs of side effects such as spleen enlargement (FIG. 19). They appeared normal and healthy during the course of the study. Furthermore, UDP-Glc-induced osteoclastogenesis is only temporary (reversible) (FIG. 18). Nevertheless, when a new compound is considered for clinical development, it is generally recommended to initiate therapy at a low dose to minimize potential adverse effects. A high potency UDP-Glc, MRS 2690, was recently developed and displays approximately 7-fold higher potency than UDP-Glc. This may allow a reduction in the dose of UDP-Glc needed while maintaining the desired effects. Measurement of UDP-Glc levels in serum or blood following UDP-Glc administration would be useful for clinical pharmacokinetic studies, but a reliable assay system for measuring the levels of UDP-Glc in serum or plasma has not yet been firmly established (personal communication with Dr. Lazarowski). This is due to the fact that platelet activation during serum preparation can result in a release of high levels of extracellular nucleotides including UDP-Glc. While heparinized plasma samples may help avoid such potential artifacts, centrifugation steps during plasma preparation inevitably result in mechanical stimulation of blood cells, which is known to promote release of nucleotides such as UDP-Glc (21, 22).

Considering high cost, side effects and ineffectiveness of conventional mobilization regimens, there is a compelling need to seek alternative mobilization regimen. UDP-Glc mobilizes functionally distinct subsets of HSPCs compared to those mobilized by G-CSF, suggesting the possibility that the combination regimen can enhances both short- and long-term repopulating capacity of the mobilized cells. In this context, UDP-Glc can be utilized as a complement regimen that potentiates the long-term repopulating capacity of G-CSF mobilized HSPCs. Therefore, on the basis of our observations, UDP-Glc mobilization, either alone or combined to G-CSF, could potentially provide a scientific basis for improving transplantation outcomes. Moreover, UDP-Glc minimally affects the immune cell content of the mobilized cells and this may alter the likelihoods of graft failure, GVHD and GVL. The small size of UDP-Glc offers other tangible advantages over other protein-based mobilizers, including easy access to intracellular targets and low cost and ease of production as well as oral bioavailability. Administration of UDP-Glc appeared to be well tolerated at high levels, suggesting the potential suitability as a therapeutic agent in man.

7.4 References

1. Hartmann, O., Le Corroller, A. G., Blaise, D., Michon, J., Philip, I., Norol, F., Janvier, M., Pico, J. L., Baranzelli, M. C., Rubie, H., et al. 1997. Peripheral blood stem cell and bone marrow transplantation for solid tumors and lymphomas: hematologic recovery and costs. A randomized, controlled trial. Ann Intern Med 126:600-607.
2. Tricot, G., Jagannath, S., Vesole, D., Nelson, J., Tindle, S., Miller, L., Cheson, B., Crowley, J., and Barlogie, B. 1995. Peripheral blood stem cell transplants for multiple myeloma: identification of favorable variables for rapid engraftment in 225 patients. Blood 85:588-596.
3. Neben, S., Marcus, K., and Mauch, P. 1993. Mobilization of hematopoietic stem and progenitor cell subpopulations from the marrow to the blood of mice following cyclophosphamide and/or granulocyte colony-stimulating factor. Blood 81:1960-1967.
4. Majolino, I., Aversa, F., Bacigalupo, A., Bandini, G., Arcese, W., and Reali, G. 1995. Allogeneic transplants of rhG-CSF-mobilized peripheral blood stem cells (PBSC) from normal donors. GITMO. Gruppo Italiano Trapianto di Midollo Osseo. Haematologica 80:40-43.
5. Platzbecker, U., Prange-Krex, G., Bornhauser, M., Koch, R., Soucek, S., Aikele, P., Haack, A., Haag, C., Schuler, U., Berndt, A., et al. 2001. Spleen enlargement in healthy donors during G-CSF mobilization of PBPCs. Transfusion 41:184-189.
6. Yeoh, J. S., Ausema, A., Wierenga, P., de Haan, G., and van Os, R. 2007. Mobilized peripheral blood stem cells provide rapid reconstitution but impaired long-term engraftment in a mouse model. Bone Marrow Transplant 39:401-409.
7. Hill, G. R., Olver, S. D., Kuns, R. D., Varelias, A., Raffelt, N. C., Don, A. L., Markey, K. A., Wilson, Y. A., Smyth, M. J., Iwakura, Y., et al. 2010. Stem cell mobilization with G-CSF induces type 17 differentiation and promotes scleroderma. Blood 116:819-828.
8. Pulliam, A. C., Hobson, M. J., Ciccone, S. L., Li, Y., Chen, S., Srour, E. F., Yang, F. C., Broxmeyer, H. E., and Clapp, D. W. 2008. AMD3100 synergizes with G-CSF to mobilize repopulating stem cells in Fanconi anemia knockout mice. Exp Hematol 36:1084-1090.
9. D'Addio, A., Curti, A., Worel, N., Douglas, K., Motta, M. R., Rizzi, S., Dan, E., Taioli, S., Giudice, V., Agis, H., et al. 2011. The addition of plerixafor is safe and allows adequate PBSC collection in multiple myeloma and lymphoma patients poor mobilizers after chemotherapy and G-CSF. Bone Marrow Transplant 46:356-363.
10. Broxmeyer, H. E., Orschell, C. M., Clapp, D. W., Hangoc, G., Cooper, S., Plett, P. A., Liles, W. C., Li, X., Graham-Evans, B., Campbell, T. B., et al. 2005. Rapid mobilization of murine and human hematopoietic stem and progenitor cells with AMD3100, a CXCR4 antagonist. J Exp Med 201:1307-1318.
11. Wright, D. E., Cheshier, S. H., Wagers, A. J., Randall, T. D., Christensen, J. L., and Weissman, I. L. 2001. Cyclophosphamide/granulocyte colony-stimulating factor causes selective mobilization of bone marrow hematopoietic stem cells into the blood after M phase of the cell cycle. Blood 97:2278-2285.
12. Mollee, P., Pereira, D., Nagy, T., Song, K., Saragosa, R., Keating, A., and Crump, M. 2002. Cyclophosphamide, etoposide and G-CSF to mobilize peripheral blood stem cells for autologous stem cell transplantation in patients with lymphoma. Bone Marrow Transplant 30:273-278.
13. Lapid, K., Vagima, Y., Kollet, O., and Lapidot, T. 2008. Egress and mobilization of hematopoietic stem and progenitor cells.
14. Di Virgilio, F., Chiozzi, P., Ferrari, D., Falzoni, S., Sanz, J. M., Morelli, A., Torboli, M., Bolognesi, G., and Baricordi, O. R. 2001. Nucleotide receptors: an emerging family of regulatory molecules in blood cells. Blood 97:587-600.
15. Sak, K., Boeynaems, J. M., and Everaus, H. 2003. Involvement of P2Y receptors in the differentiation of haematopoietic cells. J Leukoc Biol 73:442-447.
16. Linden, J. 2006. Cell biology. Purinergic chemotaxis. Science 314:1689-1690.
17. Chen, Y., Corriden, R., Inoue, Y., Yip, L., Hashiguchi, N., Zinkernagel, A., Nizet, V., Insel, P. A., and Junger, W. G. 2006. ATP release guides neutrophil chemotaxis via P2Y2 and A3 receptors. Science 314:1792-1795.
18. Rossi, L., Manfredini, R., Bertolini, F., Ferrari, D., Fogli, M., Zini, R., Salati, S., Salvestrini, V., Gulinelli, S., Adinolfi, E., et al. 2007. The extracellular nucleotide UTP is a potent inducer of hematopoietic stem cell migration. Blood 109:533-542.
19. Lemoli, R. M., Ferrari, D., Fogli, M., Rossi, L., Pizzirani, C., Forchap, S., Chiozzi, P., Vaselli, D., Bertolini, F., Foutz, T., et al. 2004. Extracellular nucleotides are potent 20. Abbracchio, M. P., and Burnstock, G. 1998. Purinergic signalling: pathophysiological roles. Jpn J Pharmacol 78:113-145.
21. Lazarowski, E. R., Shea, D. A., Boucher, R. C., and Harden, T. K. 2003. Release of cellular UDP-glucose as a potential extracellular signaling molecule. Mol Pharmacol 63:1190-1197.
22. Arase, T., Uchida, H., Kajitani, T., Ono, M., Tamaki, K., Oda, H., Nishikawa, S., Kagami, M., Nagashima, T., Masuda, H., et al. 2009. The UDP-glucose receptor P2RY14 triggers innate mucosal immunity in the female reproductive tract by inducing IL-8. J Immunol 182:7074-7084.
23. Eigenbrodt, E., Reinacher, M., Scheefers-Borchel, U., Scheefers, H., and Friis, R. 1992. Double role for pyruvate kinase type M2 in the expansion of phosphometabolite pools found in tumor cells. Crit Rev Oncog 3:91-115.
24. He, S., Kim, I., Lim, M. S., and Morrison, S. J. 2011. Sox17 expression confers self-renewal potential and fetal stem cell characteristics upon adult hematopoietic progenitors. Genes Dev 25:1613-1627.
25. Roberts, A. W., Foote, S., Alexander, W. S., Scott, C., Robb, L., and Metcalf, D. 1997. Genetic influences determining progenitor cell mobilization and leukocytosis induced by granulocyte colony-stimulating factor. Blood 89:2736-2744.
26. Park, C. Y., Majeti, R., and Weissman, I. L. 2008. In vivo evaluation of human hematopoiesis through xenotransplantation of purified hematopoietic stem cells from umbilical cord blood. Nat Protoc 3:1932-1940.
27. Purton, L. E., and Scadden, D. T. 2006. Osteoclasts eat stem cells out of house and home. Nat Med 12:610-611.
28. Liu, F., Wu, H. Y., Wesselschmidt, R., Kornaga, T., and Link, D. C. 1996. Impaired production and increased apoptosis of neutrophils in granulocyte colony-stimulating factor receptor-deficient mice. Immunity 5:491-501.
29. Steinman, R. A. 2002. Cell cycle regulators and hematopoiesis. Oncogene 21:3403-3413.
30. Tesio, M., Golan, K., Corso, S., Giordano, S., Schajnovitz, A., Vagima, Y., Shivtiel, S., Kalinkovich, A., Caione, L., Gammaitoni, L., et al. 2011. Enhanced c-Met activity promotes G-CSF-induced mobilization of hematopoietic progenitor cells via ROS signaling. Blood 117:419-428.
31. Dar, A., Schajnovitz, A., Lapid, K., Kalinkovich, A., Itkin, T., Ludin, A., Kao, W. M., Battista, M., Tesio, M., Kollet, O., et al. 2011. Rapid mobilization of hematopoietic progenitors by AMD3100 and catecholamines is mediated by CXCR4-dependent SDF-1 release from bone marrow stromal cells. Leukemia.
32. Bai, X. C., Lu, D., Liu, A. L., Zhang, Z. M., Li, X. M., Zou, Z. P., Zeng, W. S., Cheng, B. L., and Luo, S. Q. 2005. Reactive oxygen species stimulates receptor activator of NF-kappaB ligand expression in osteoblast. J Biol Chem 280:17497-17506.
33. Barsony, J., Sugimura, Y., and Verbalis, J. G. 2011. Osteoclast response to low extracellular sodium and the mechanism of hyponatremia-induced bone loss. J Biol Chem 286:10864-10875.
34. Kollet, O., Dar, A., Shivtiel, S., Kalinkovich, A., Lapid, K., Sztainberg, Y., Tesio, M., Samstein, R. M., Goichberg, P., Spiegel, A., et al. 2006. Osteoclasts degrade endosteal components and promote mobilization of hematopoietic progenitor cells. Nat Med 12:657-664.
35. Calvi, L. M., Adams, G. B., Weibrecht, K. W., Weber, J. M., Olson, D. P., Knight, M. C., Martin, R. P., Schipani, E., Divieti, P., Bringhurst, F. R., et al. 2003. Osteoblastic cells regulate the haematopoietic stem cell niche. Nature 425:841-846.
36. Miyamoto, K., Yoshida, S., Kawasumi, M., Hashimoto, K., Kimura, T., Sato, Y., Kobayashi, T., Miyauchi, Y., Hoshi, H., Iwasaki, R., et al. 2011. Osteoclasts are dispensable for hematopoietic stem cell maintenance and mobilization. J Exp Med 208:2175-2181.
37. Takamatsu, Y., Simmons, P. J., Moore, R. J., Morris, H. A., To, L. B., and Levesque, J. P. 1998. Osteoclast-mediated bone resorption is stimulated during short-term administration of granulocyte colony-stimulating factor but is not responsible for hematopoietic progenitor cell mobilization. Blood 92:3465-3473.
38. Yoshida, H., Hayashi, S., Kunisada, T., Ogawa, M., Nishikawa, S., Okamura, H., Sudo, T., Shultz, L. D., and Nishikawa, S. 1990. The murine mutation osteopetrosis is in the coding region of the macrophage colony stimulating factor gene. Nature 345:442-444.
39. Ke, H. Z., Qi, H., Weidema, A. F., Zhang, Q., Panupinthu, N., Crawford, D. T., Grasser, W. A., Paralkar, V. M., Li, M., Audoly, L. P., et al. 2003. Deletion of the P2X7 nucleotide receptor reveals its regulatory roles in bone formation and resorption. Mol Endocrinol 17:1356-1367.
40. Levesque, J. P., Hendy, J., Takamatsu, Y., Williams, B., Winkler, I. G., and Simmons, P. J. 2002. Mobilization by either cyclophosphamide or granulocyte colony-stimulating factor transforms the bone marrow into a highly proteolytic environment. Exp Hematol 30:440-449.
41. Peled, A., Petit, I., Kollet, O., Magid, M., Ponomaryov, T., Byk, T., Nagler, A., Ben-Hur, H., Many, A., Shultz, L., et al. 1999. Dependence of human stem cell engraftment and repopulation of NOD/SCID mice on CXCR4. Science 283:845-848.
42. Fricks, I. P., Maddileti, S., Carter, R. L., Lazarowski, E. R., Nicholas, R. A., Jacobson, K. A., and Harden, T. K. 2008. UDP is a competitive antagonist at the human P2Y14 receptor. J Pharmacol Exp Ther 325:588-594.
43. Schmitz, N., Linch, D. C., Dreger, P., Goldstone, A. H., Boogaerts, M. A., Ferrant, A., Demuynck, H. M., Link, H., Zander, A., and Barge, A. 1996. Randomised trial of filgrastim-mobilised peripheral blood progenitor cell transplantation versus autologous bone-marrow transplantation in lymphoma patients. Lancet 347:353-357.
44. Cottler-Fox, M. H., Lapidot, T., Petit, I., Kollet, O., DiPersio, J. F., Link, D., and Devine, S. 2003. Stem cell mobilization. Hematology Am Soc Hematol Educ Program:419-437.
45. Hornung, R. L., and Longo, D. L. 1992. Hematopoietic stem cell depletion by restorative growth factor regimens during repeated high-dose cyclophosphamide therapy. Blood 80:77-83.
46. Chitteti, B. R., Liu, Y., and Srour, E. F. 2011. Genomic and proteomic analysis of the impact of mitotic quiescence on the engraftment of human CD34+ cells. PLoS One 6:e17498.
47. Micklem, H. S., Anderson, N., and Ross, E. 1975. Limited potential of circulating haemopoietic stem cells. Nature 256:41-43.
48. Schwarzenberger, P., Huang, W., Oliver, P., Byrne, P., La Russa, V., Zhang, Z., and Kolls, J. K. 2001. IL-17 mobilizes peripheral blood stem cells with short- and long-term repopulating ability in mice. J Immunol 167: 2081-2086.
49. Li, J. M., Giver, C. R., Lu, Y., Hossain, M. S., Akhtari, M., and Waller, E. K. 2009. Separating graft-versusleukemia from graft-versus-host disease in allogeneic hematopoietic stem cell transplantation. Immunotherapy 1:599-621.
50. Lekli, I., Gurusamy, N., Ray, D., Tosaki, A., and Das, D. K. 2009. Redox regulation of stem cell mobilization. Can J Physiol Pharmacol 87:989-995.
51. Pruijt, J. F., Verzaal, P., van Os, R., de Kruijf, E. J., van Schie, M. L., Mantovani, A., Vecchi, A., Lindley, I. J., Willemze, R., Starckx, S., et al. 2002. Neutrophils are indispensable for hematopoietic stem cell mobilization induced by interleukin-8 in mice. Proc Natl Acad Sci USA 99:6228-6233.
52. Brautigam, V. M., Dubyak, G. R., Crain, J. M., and Watters, J. J. 2008. The inflammatory effects of UDP-glucose in N9 microglia are not mediated by P2Y14 receptor activation. Purinergic Signal 4:73-78.
53. Scrivens, M., and Dickenson, J. M. 2005. Pharmacological effects mediated by UDP-glucose that are independent of P2Y14 receptor expression. Pharmacol Res 51:533-538.
54. Liu, F., Poursine-Laurent, J., and Link, D. C. 2000. Expression of the G-CSF receptor on hematopoietic progenitor cells is not required for their mobilization by G-CSF. Blood 95:3025-3031.
55. Greenbaum, A. M., and Link, D. C. 2011. Mechanisms of G-CSF-mediated hematopoietic stem and progenitor mobilization. Leukemia 25:211-217.
56. Lee, B. C., Cheng, T., Adams, G. B., Attar, E. C., Miura, N., Lee, S. B., Saito, Y., Olszak, I., Dombkowski, D., Olson, D. P., et al. 2003. P2Y-like receptor, GPR105 (P2Y14), identifies and mediates chemotaxis of bone-marrow hematopoietic stem cells. Genes Dev 17:1592-1604.
57. Passegue, E., Wagers, A. J., Giuriato, S., Anderson, W. C., and Weissman, I. L. 2005. Global analysis of proliferation and cell cycle gene expression in the regulation of hematopoietic stem and progenitor cell fates. J Exp Med 202:1599-1611.
58. Ploemacher, R. E., van der Sluijs, J. P., Voerman, J. S., and Brons, N. H. 1989. An in vitro limiting-dilution assay of long-term repopulating hematopoietic stem cells in the mouse. Blood 74:2755-2763.
59. Cho, J., Shen, H., Yu, H., Li, H., Cheng, T., Lee, S. B., and Lee, B. C. 2011. Ewing sarcoma gene Ews regulates hematopoietic stem cell senescence. Blood 117:1156-1166.

Various publications are cited herein, the contents of which are hereby incorporated by reference in their entireties.

I claim:

1. A pharmaceutical combination comprising: (a) a uridine diphosphate glucose (UDP-glucose) compound at a dosage of 200 to 500 mg/kg and (b) granulocyte colony stimulating factor (G-CSF) at a dosage of 250 to 300 µg/kg, wherein the combination of the UDP-glucose compound and the G-CSF exhibit synergistic enhancement of hematopoietic stem progenitor cells mobilization.

2. The pharmaceutical combination of claim 1, further comprising one or more pharmaceutically acceptable carriers.

3. The pharmaceutical combination of claim 1, further comprising one or more pharmaceutically acceptable excipients.

4. The pharmaceutical combination of claim 1, wherein the composition is formulated for subcutaneous administration.

5. The pharmaceutical combination of claim 1, wherein the composition is formulated for intramuscular, intravenous, intraperitoneal, oral, or rectal administration.

6. The pharmaceutical combination of claim 1, wherein the composition is formulated as a solid formulation.

7. The pharmaceutical combination of claim 1, wherein the composition is formulated as a liquid formulation.

* * * * *